United States Patent
Thorne et al.

[19]

[11] Patent Number: 5,928,200
[45] Date of Patent: Jul. 27, 1999

[54] SELF RETRACTING MEDICAL NEEDLE APPARATUS AND METHODS

[75] Inventors: Gale H. Thorne, Bountiful; David L. Thorne, Kaysville; Mark Nelson, Sandy; Charles V. Owen, Highland; Sandra A. Thorne, Bountiful, all of Utah

[73] Assignee: Specialized Health Products, Inc., Bountiful, Utah

[21] Appl. No.: 09/105,078

[22] Filed: Jun. 25, 1998

Related U.S. Application Data

[60] Division of application No. 08/882,644, Jun. 25, 1997, which is a continuation-in-part of application No. 08/744,108, Nov. 5, 1996, which is a continuation of application No. 08/595,802, Feb. 2, 1996, which is a continuation of application No. 08/565,881, Dec. 1, 1995, Pat. No. 5,616,135, which is a continuation of application No. 08/436,976, May 8, 1995, Pat. No. 5,487,734, application No. 08/484,533, Jun. 7, 1995, Pat. No. 5,542,927, and application No. 08/455,514, May 31, 1995, Pat. No. 5,549,708, which is a continuation of application No. 08/370,728, Jan. 10, 1995, Pat. No. 5,480,385, said application No. 08/436,976, and application No. 08/484,533, each is a continuation-in-part of application No.08/370,728.

[51] Int. Cl.⁶ .................................................. A61M 5/00
[52] U.S. Cl. ........................... 604/195; 604/263; 128/763
[58] Field of Search .................................... 604/195, 198, 604/263, 110, 187; 128/763, 764, 765, 919, 766

[56] References Cited

U.S. PATENT DOCUMENTS

| | | | |
|---|---|---|---|
| 3,587,575 | 6/1971 | Lichenstein | 128/128 |
| 4,676,783 | 6/1987 | Jagger | 604/171 |
| 4,747,831 | 5/1988 | Kulli | 604/110 |
| 4,813,936 | 3/1989 | Schroeder | 604/195 |
| 4,828,548 | 5/1989 | Walter | 604/164 |
| 4,850,374 | 7/1989 | Diaz-Ramos | 128/763 |
| 4,892,525 | 1/1990 | Hermann, Jr. | 604/263 |
| 4,900,307 | 2/1990 | Kulli | 604/110 |
| 4,904,242 | 2/1990 | Kulli | 604/110 |
| 4,909,794 | 3/1990 | Haber | 604/195 |
| 4,927,414 | 5/1990 | Kulli | 604/110 |
| 4,929,241 | 5/1990 | Kulli | 604/263 |
| 4,936,830 | 6/1990 | Verlier | 604/110 |
| 4,946,446 | 8/1990 | Vadher | 604/198 |

(List continued on next page.)

FOREIGN PATENT DOCUMENTS 9-28811   2/1997   Japan .

OTHER PUBLICATIONS

Patricia Seremet, "Small Tolland Company Takes Jab at Safety Needle Market," *The Hartford Courant*, Sep. 13, 1995, pp. F1 and F3.

*Primary Examiner*—John D. Yasko
*Attorney, Agent, or Firm*—Gale H. Thorne; Paul S. Evans

[57] ABSTRACT

Method and apparatus associated with safe retraction of medical needles after use. Embodiments are disclosed for self-retracting needle systems for both blood draw, syringe and catheter insertion systems. Invention manufacture requires only a minimal number and complexity of parts such that a projected manufacturing cost is potentially low enough to permit the apparatus to be cost competitive with contemporary non-self retracting needle systems. Methods for making and assembling each of the disclosed the embodiments is also disclosed. One blood draw embodiment can be made with as few as three molded parts. Energy-storing, needle-retracting mechanisms comprise elastic tubing and vacuum generating piston parts. In an elastic tubing embodiment, selective, constrictive control of stretched tubing volumes effectively inhibits regurgitant flow from the needle. In all embodiments, needle retraction is a single handed operation permitting a technician's other hand to be used in wound care. A combination of parts, comprising the apparatus housing and a needle cover, are used as a transport container which protects a medical needle from inadvertent contamination with requiring special packaging, thereby, further reducing apparatus costs.

25 Claims, 77 Drawing Sheets

U.S. PATENT DOCUMENTS

| | | | |
|---|---|---|---|
| 4,955,870 | 9/1990 | Ridderheim | 604/195 |
| 4,966,593 | 10/1990 | Lennox | 604/198 |
| 4,978,340 | 12/1990 | Terrill | 604/195 |
| 4,985,021 | 1/1991 | Straw | 604/198 |
| 4,986,816 | 1/1991 | Steiner | 604/192 |
| 4,988,339 | 1/1991 | Vadher | 604/197 |
| 4,994,034 | 2/1991 | Botich | 604/110 |
| 4,995,870 | 2/1991 | Baskas | 604/110 |
| 5,092,853 | 3/1992 | Couvertier | 604/195 |
| 5,098,402 | 3/1992 | Davis | 604/195 |
| 5,114,404 | 5/1992 | Paxton | 604/110 |
| 5,139,489 | 8/1992 | Hollister | 604/192 |
| 5,147,303 | 9/1992 | Martin | 604/110 |
| 5,154,285 | 10/1992 | Hollister | 206/365 |
| 5,180,370 | 1/1993 | Gillespie | 604/110 |
| 5,188,599 | 2/1993 | Botich | 604/110 |
| 5,193,552 | 3/1993 | Columbus et al. | 128/760 |
| 5,195,983 | 3/1993 | Boese | 604/192 |
| 5,195,985 | 3/1993 | Hall | 604/195 |
| 5,205,823 | 4/1993 | Zdeb | 604/110 |
| 5,205,824 | 4/1993 | Mazur | 604/110 |
| 5,209,739 | 5/1993 | Talslay | 604/195 |
| 5,215,533 | 6/1993 | Robb | 604/195 |
| 5,246,428 | 9/1993 | Falknor | 604/198 |
| 5,254,099 | 10/1993 | Kuracina | 604/198 |
| 5,256,153 | 10/1993 | Hake | 604/198 |
| 5,267,976 | 12/1993 | Guerineau | 604/198 |
| 5,320,606 | 6/1994 | Jore | 604/110 |
| 5,356,392 | 10/1994 | Firth et al. | 604/198 |
| 5,374,250 | 12/1994 | Dixon | 604/110 |
| 5,403,283 | 4/1995 | Luther | 604/164 |
| 5,403,286 | 4/1995 | Lockwood, Jr. | 604/158 |
| 5,573,510 | 11/1996 | Isaacson | 640/158 |

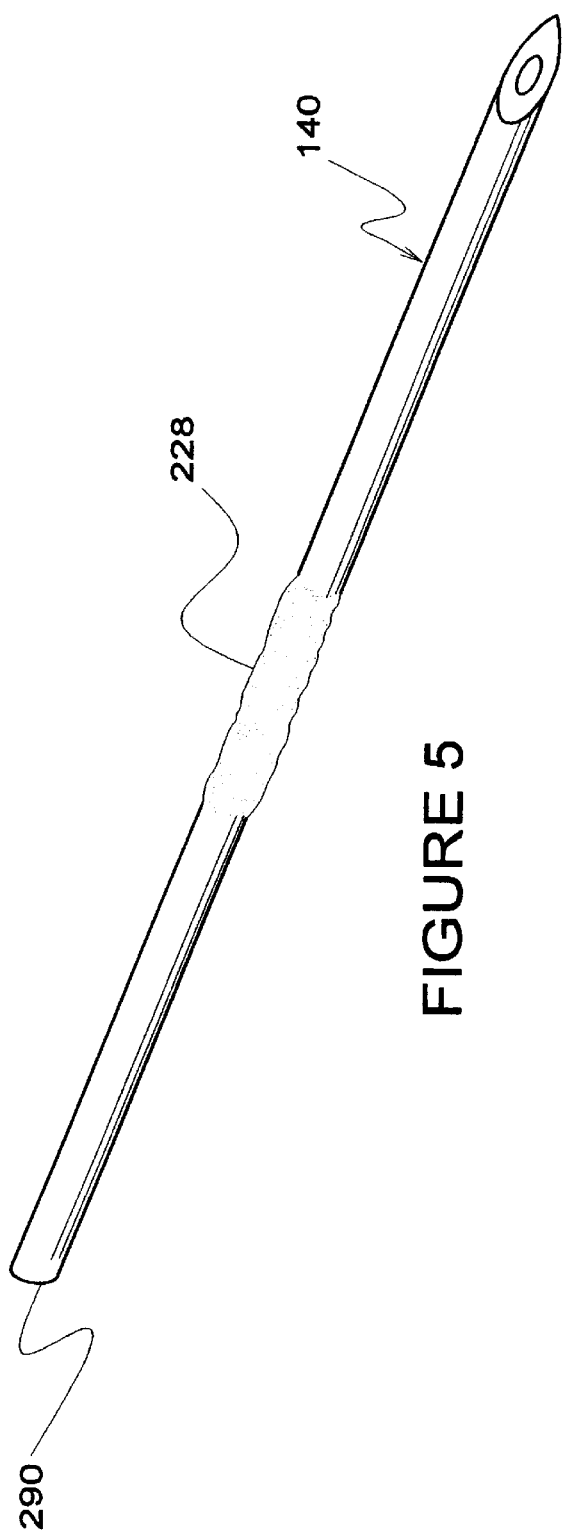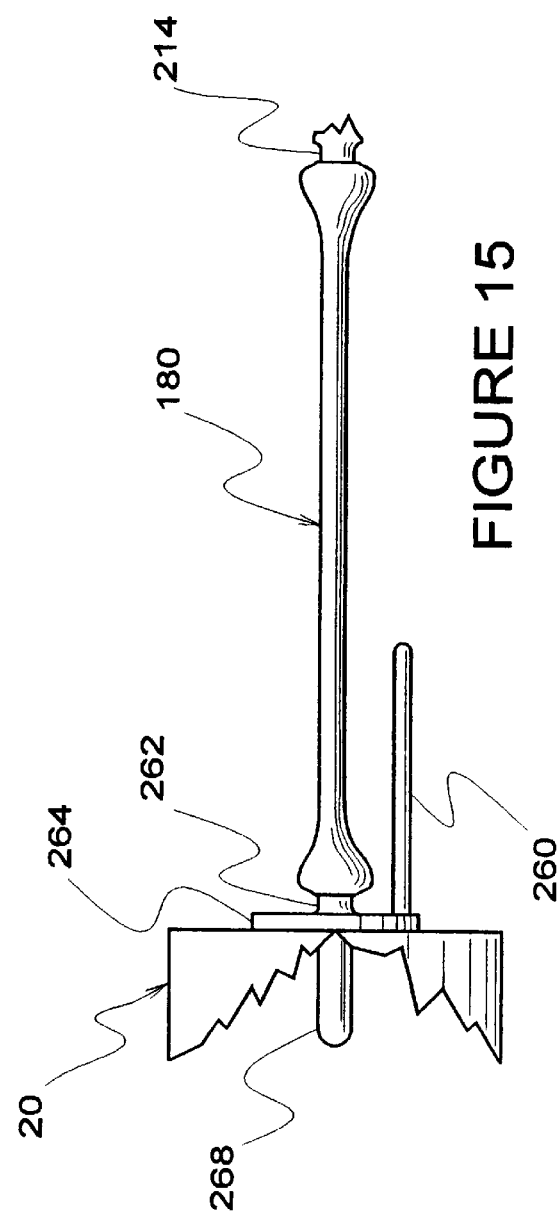

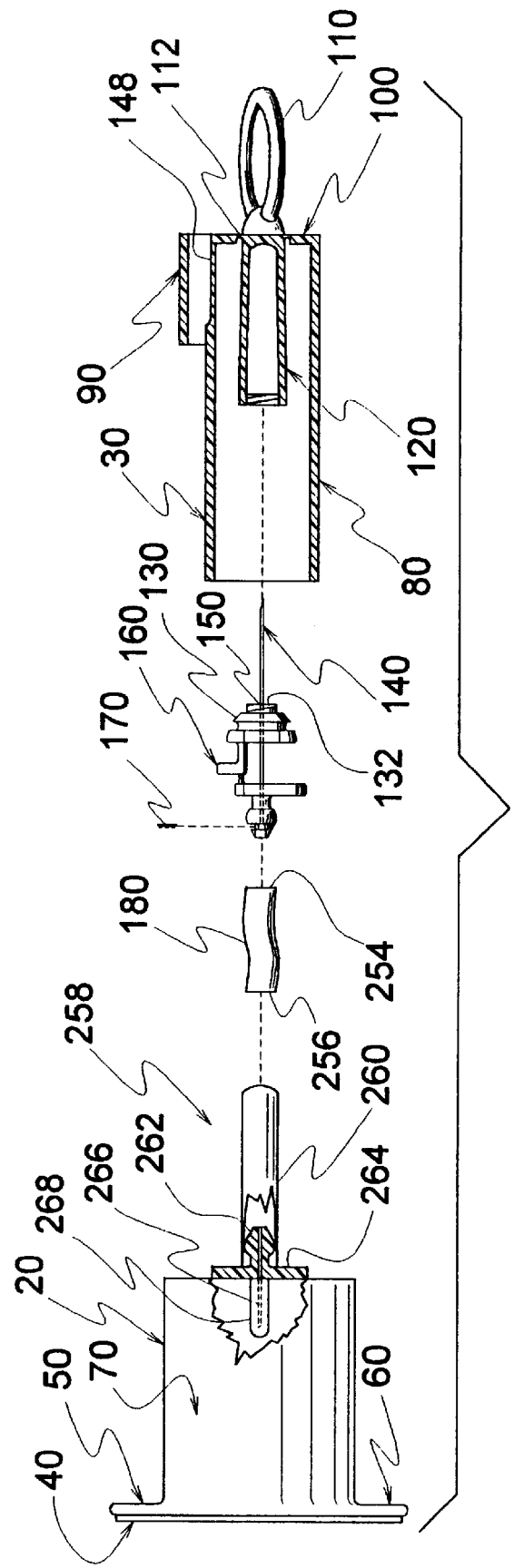

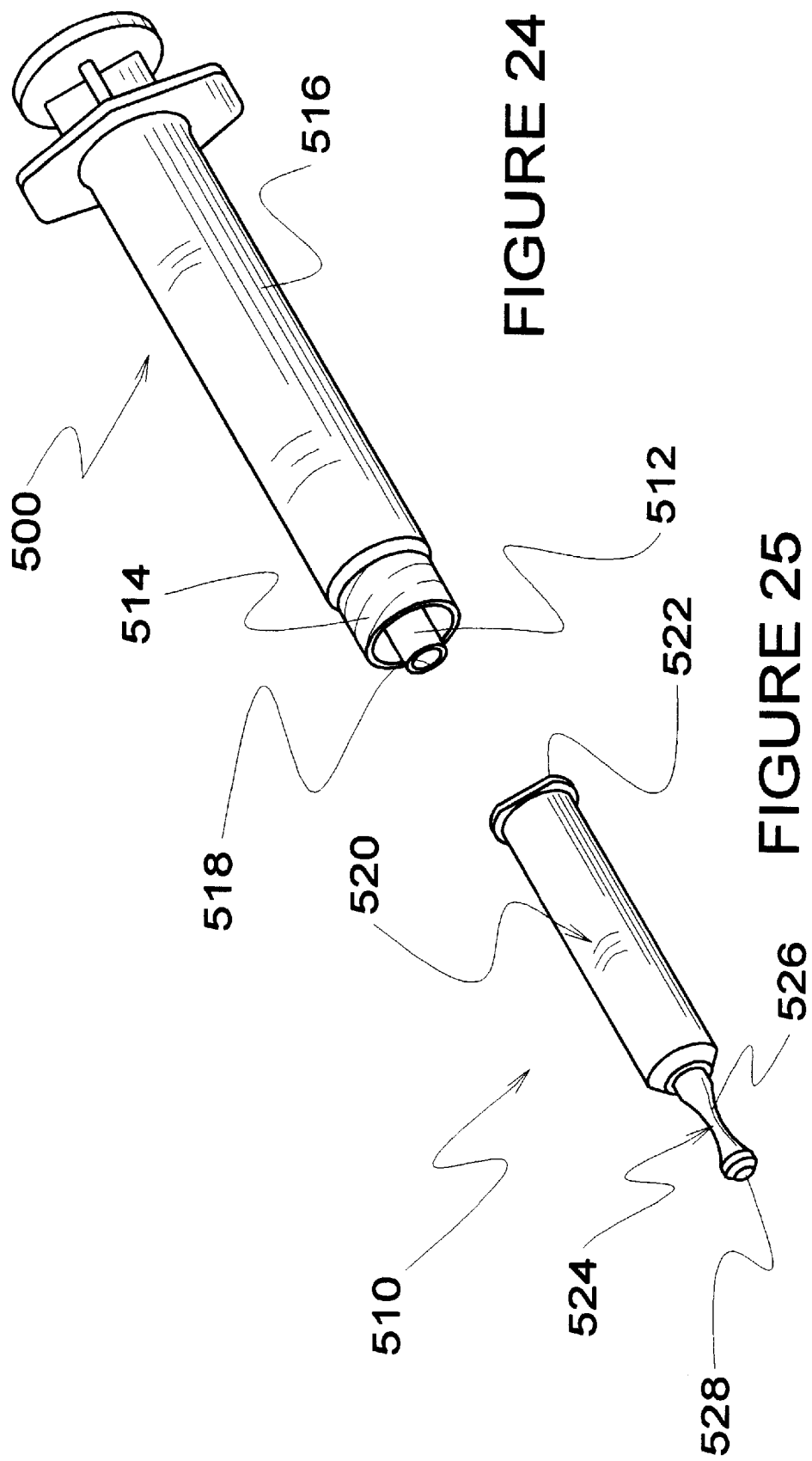

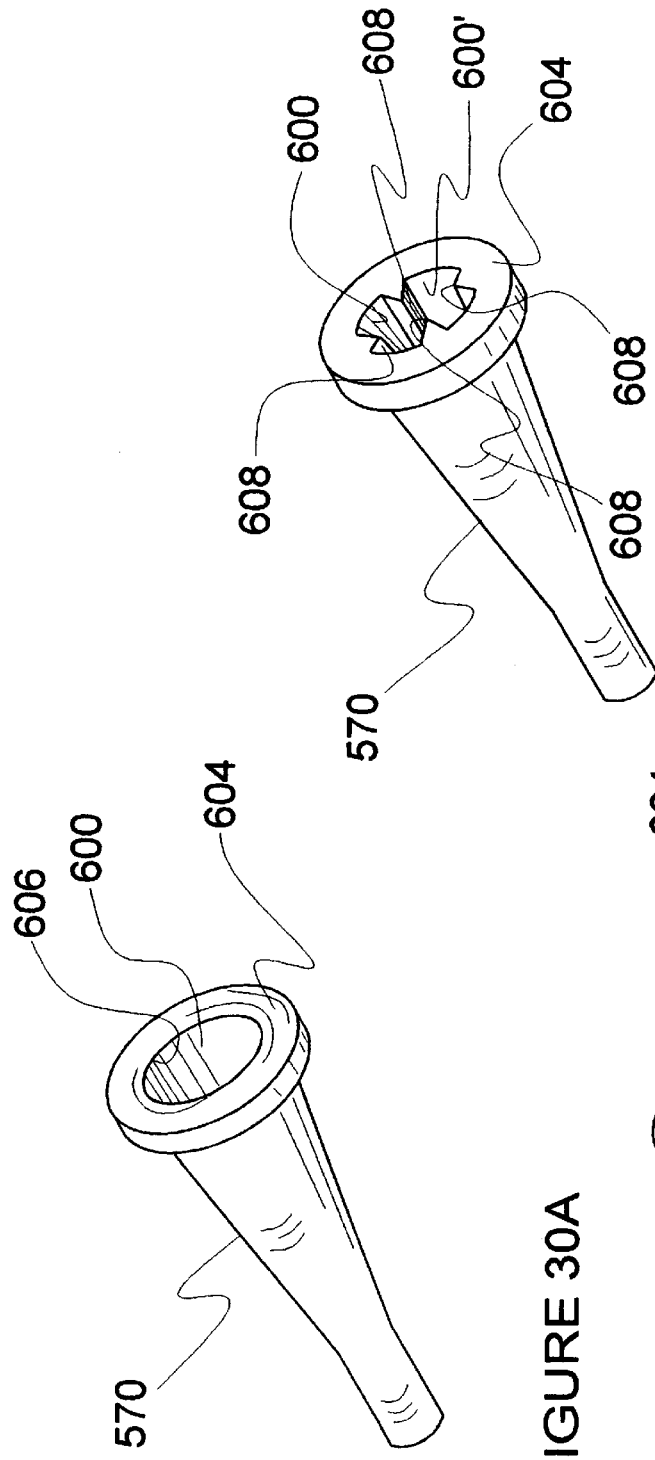
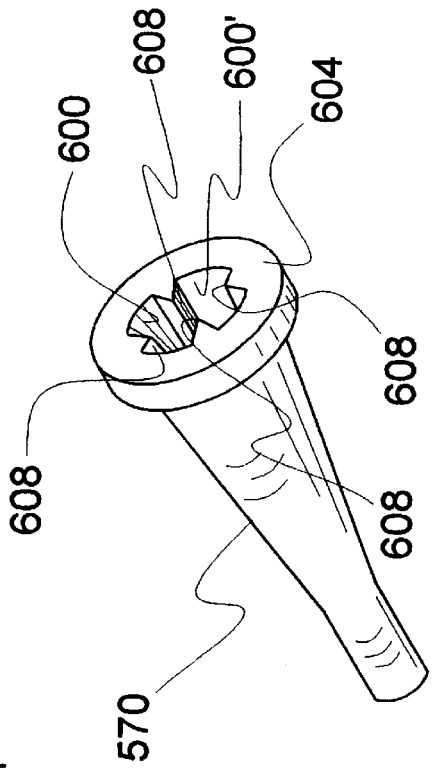
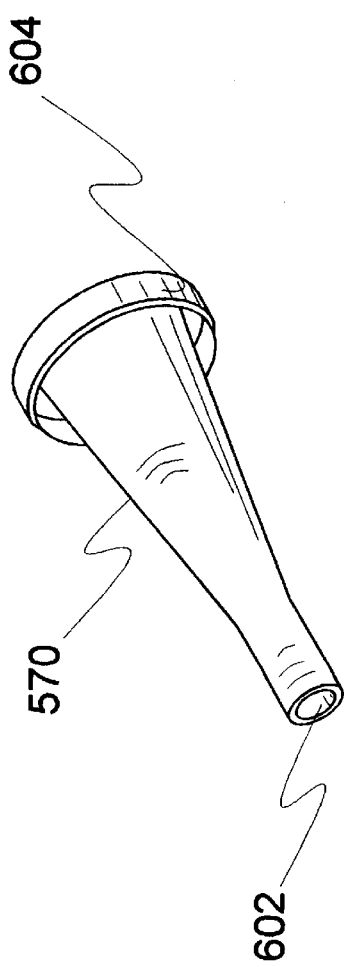
FIGURE 30A
FIGURE 30B
FIGURE 30C

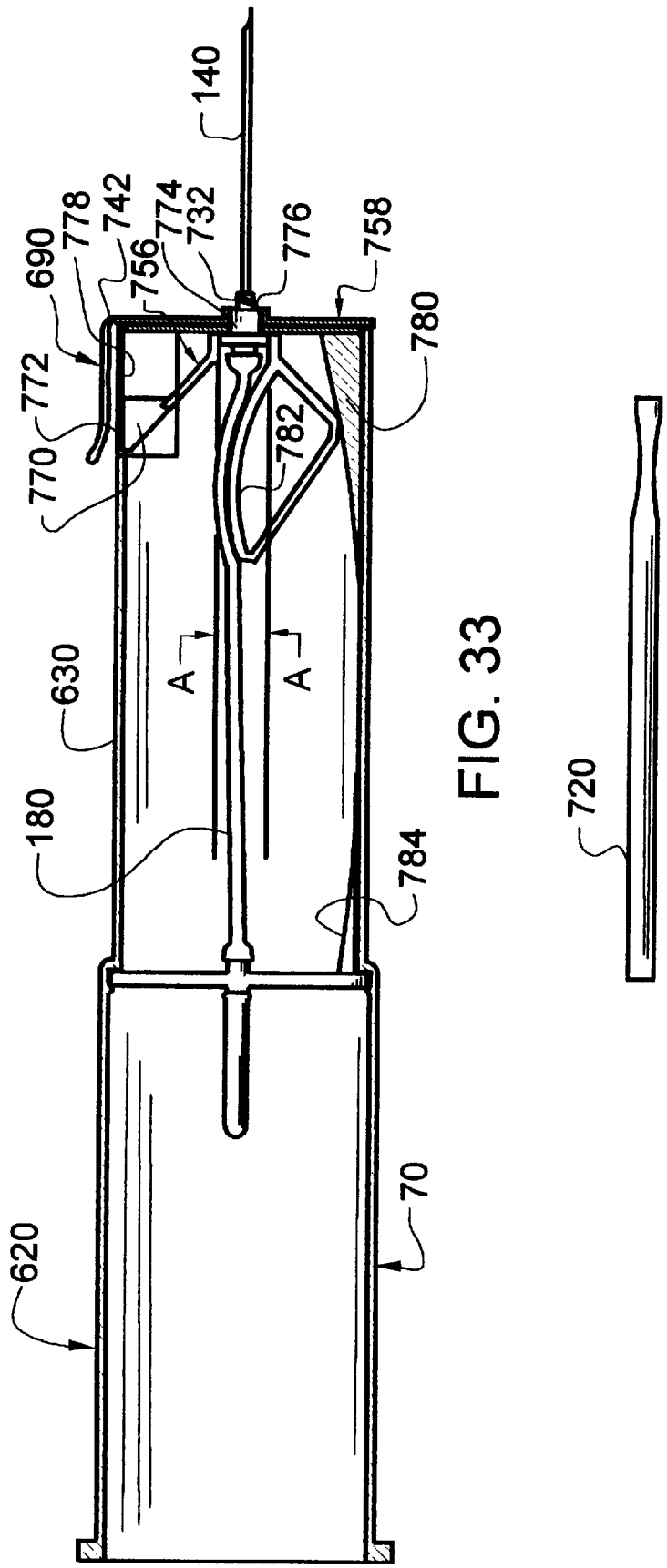

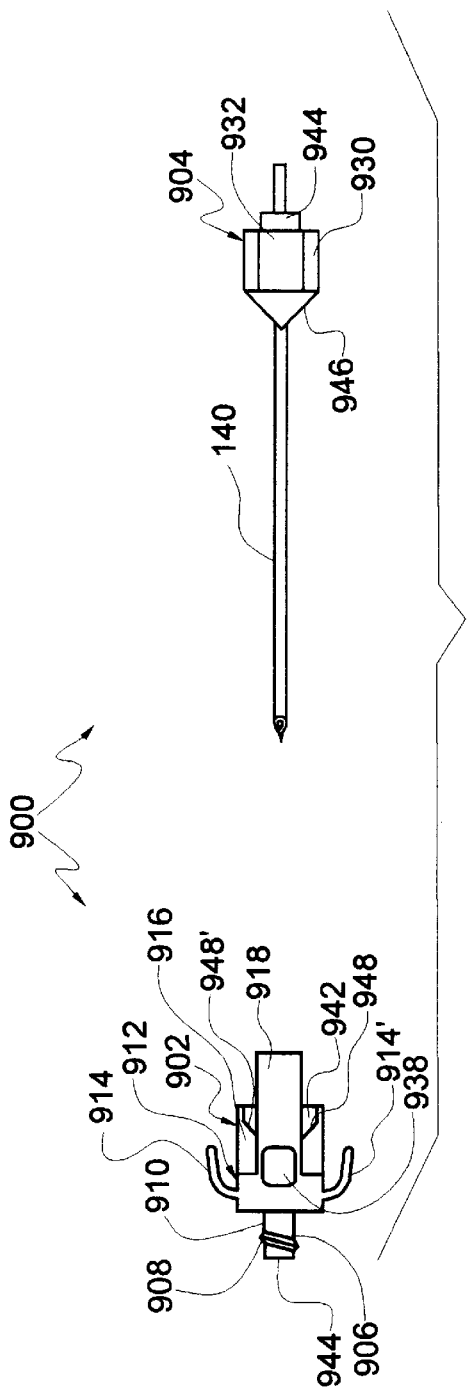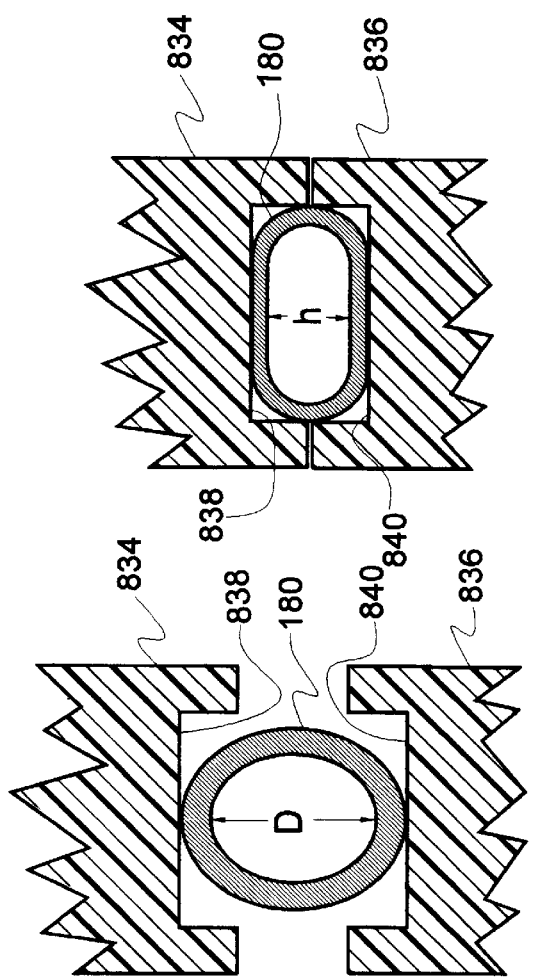
FIGURE 48
FIGURE 42
FIGURE 41

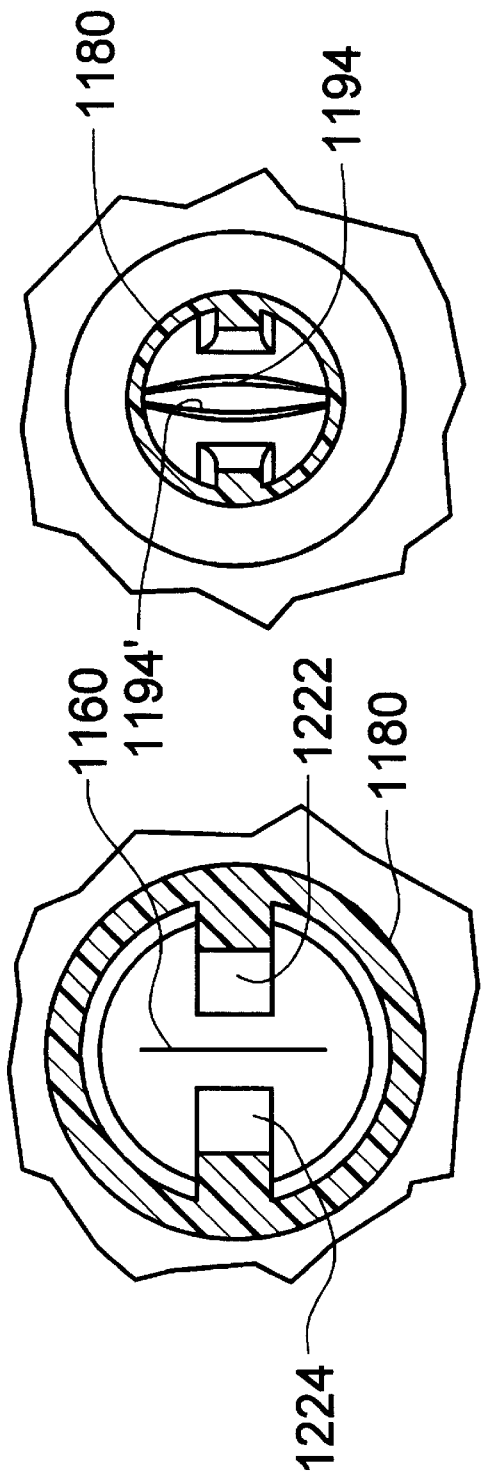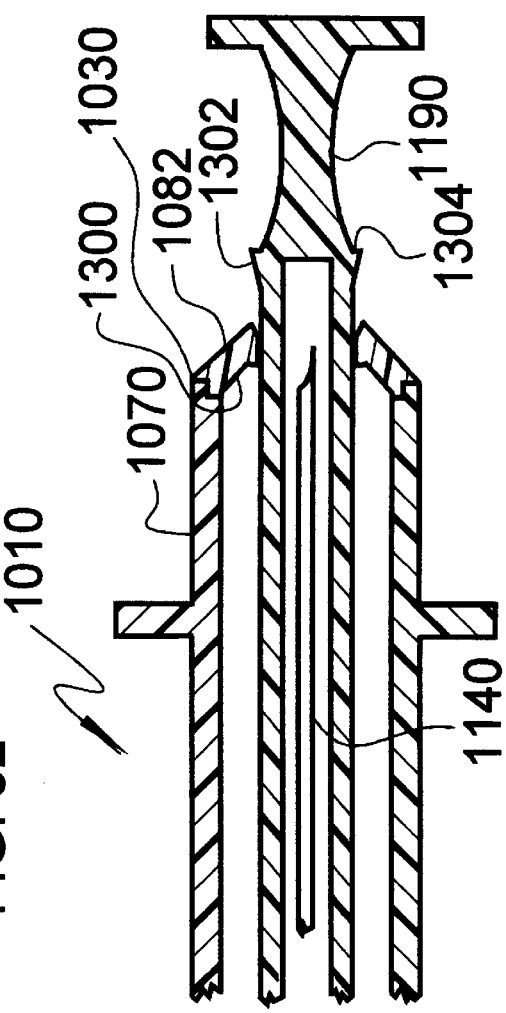

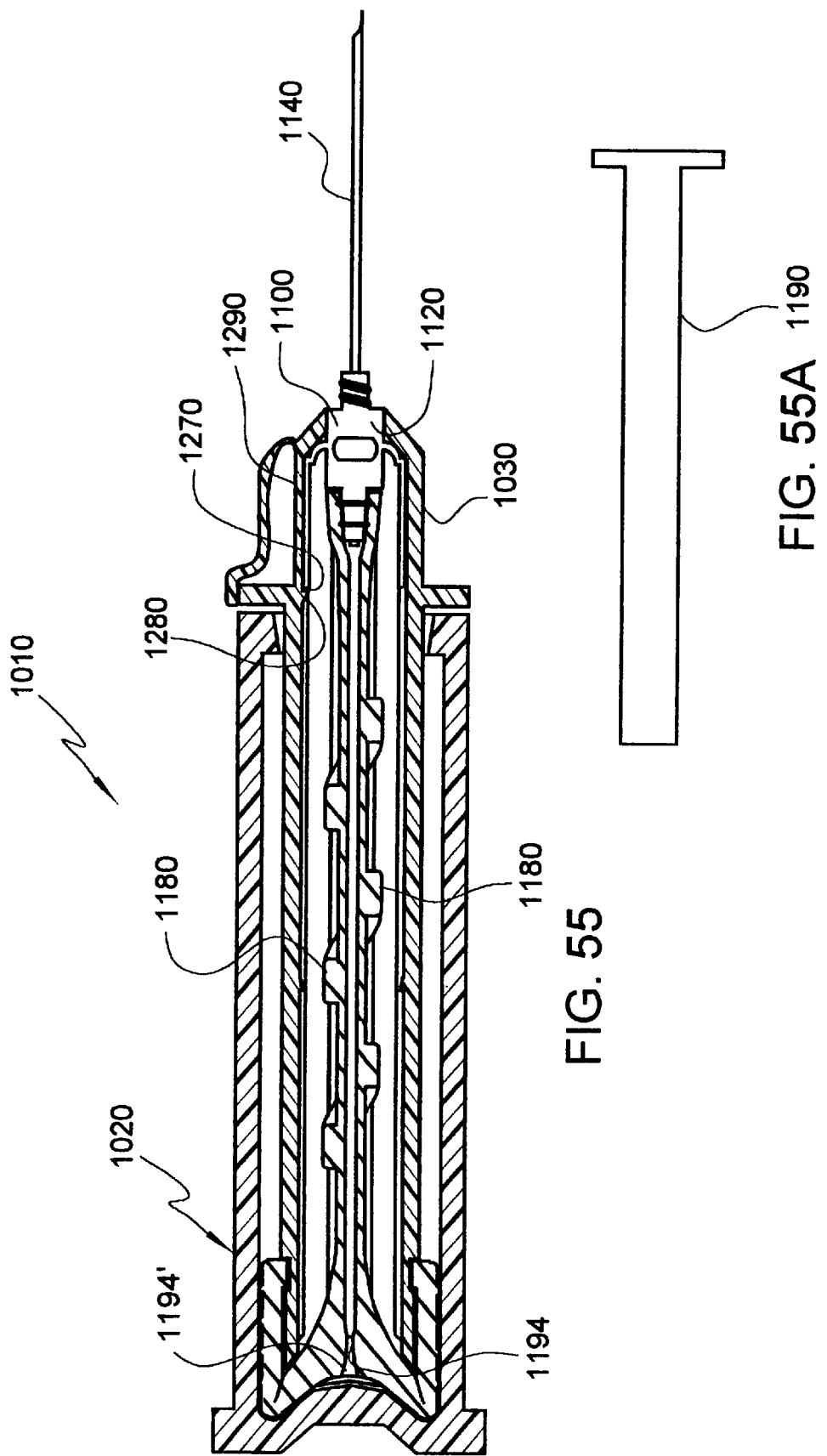

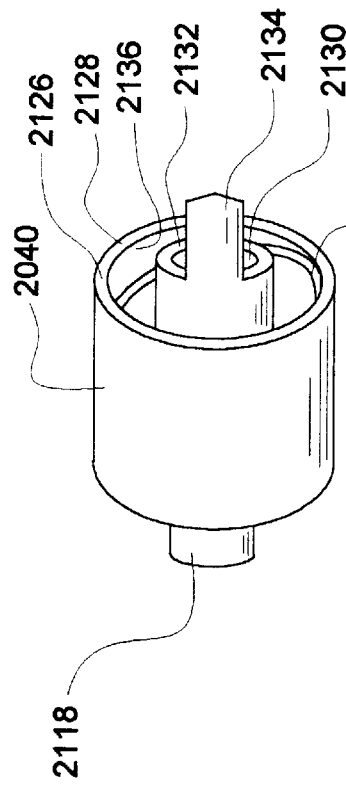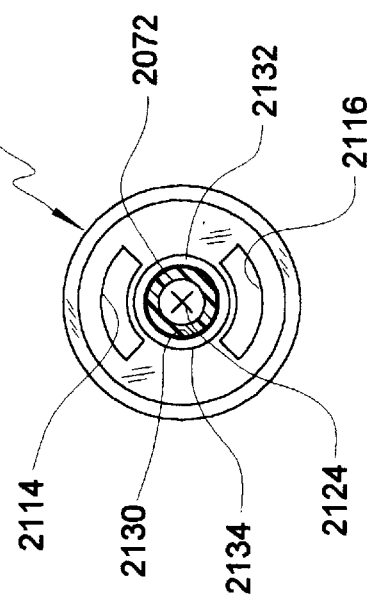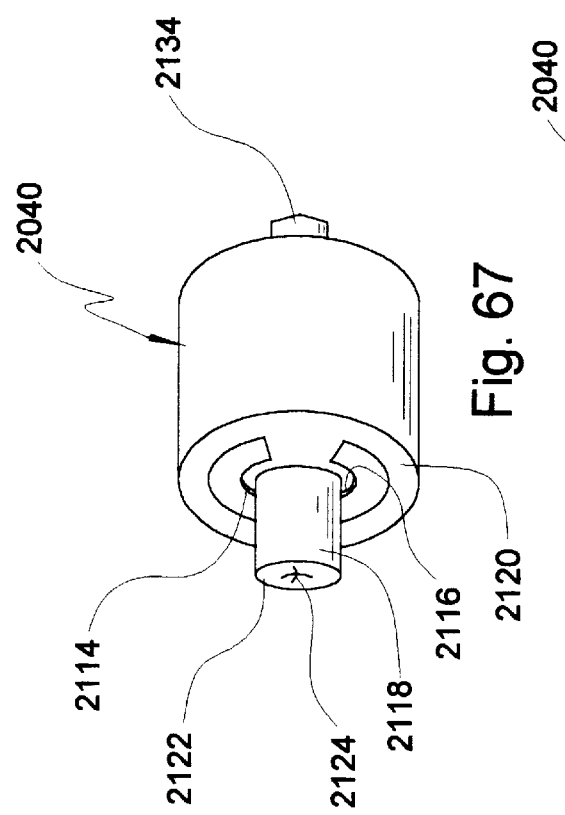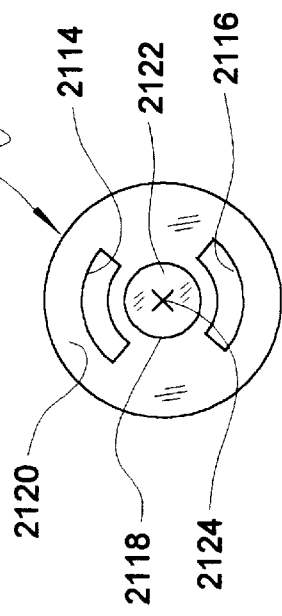

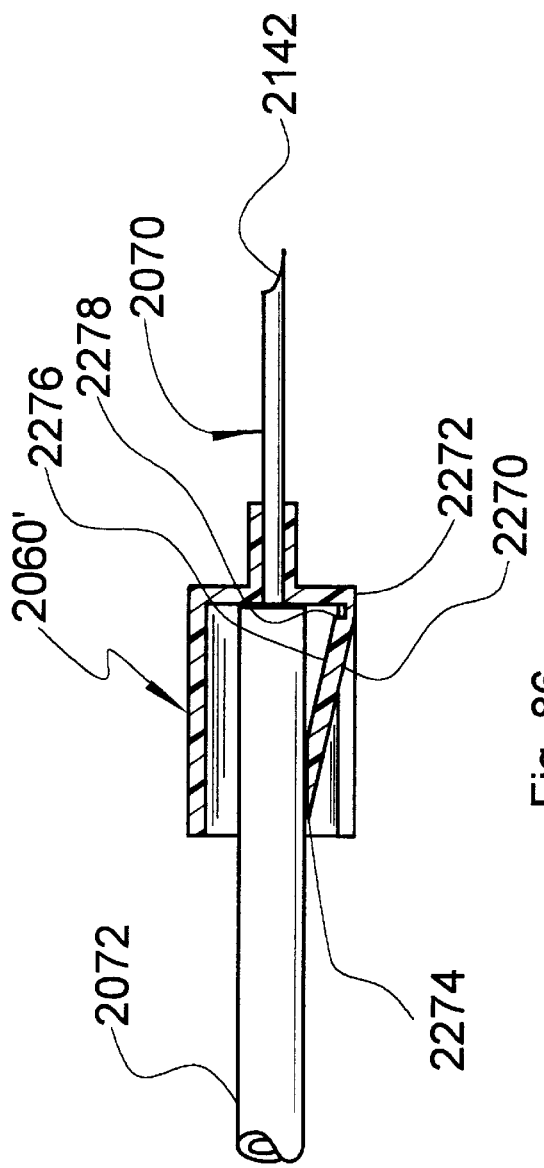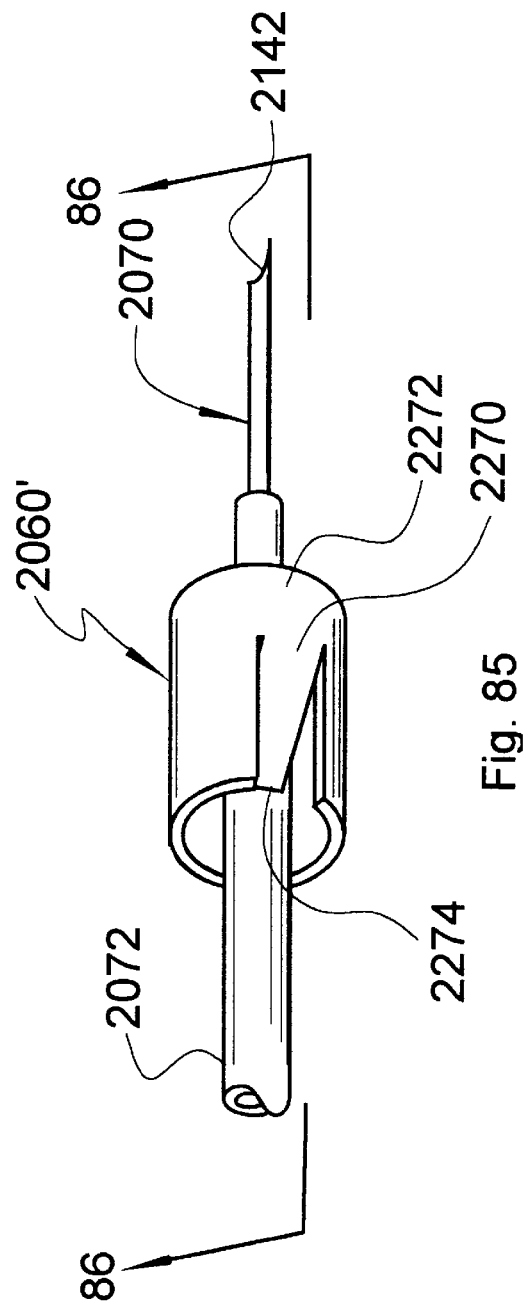
Fig. 86
Fig. 85

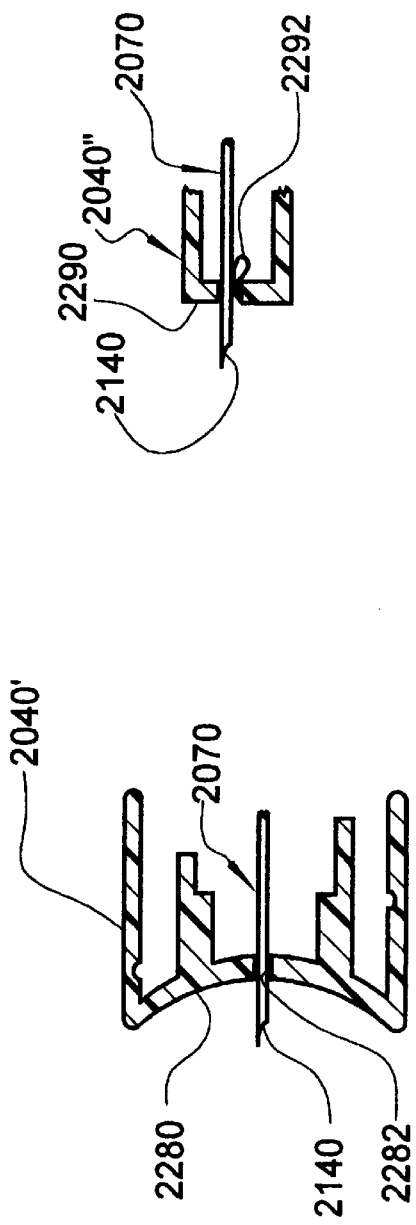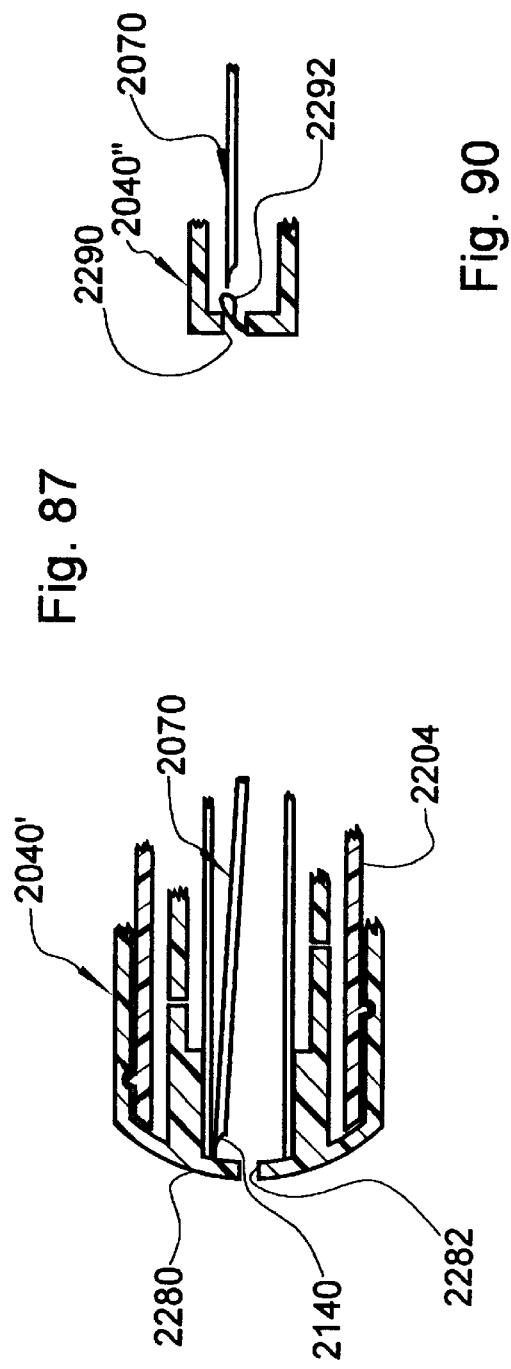

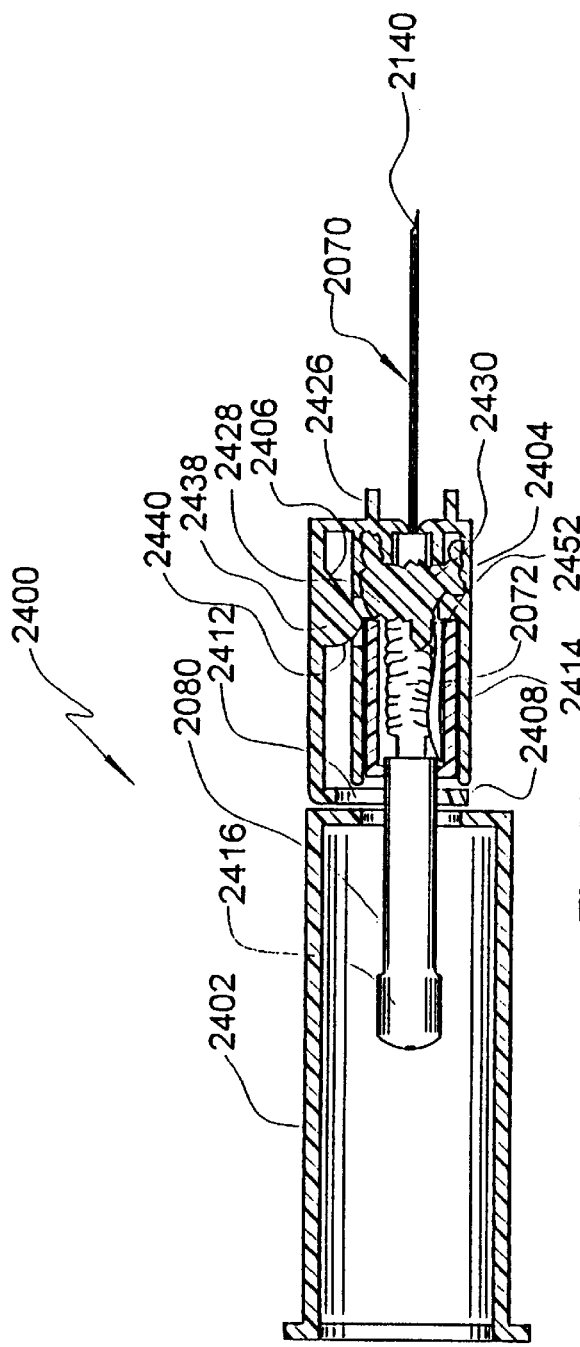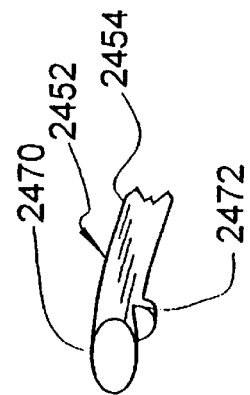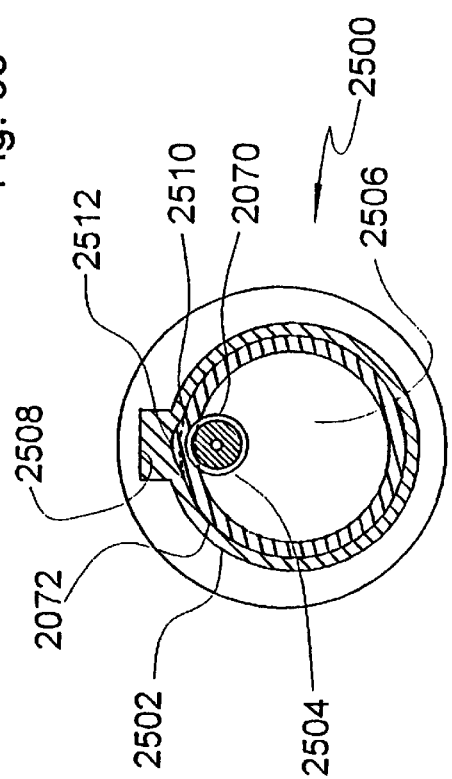
Fig. 99
Fig. 100
Fig. 101

SELF RETRACTING MEDICAL NEEDLE APPARATUS AND METHODS

This application is a divisional of application Ser. No. 08/882,644, filed Jun. 25, 1997, which is a continuation-in-part of U.S. patent application Ser. No. 08/744,108 filed Nov. 5, 1996 entitled Self Retracting Medical Needle Apparatus and Methods, which is a continuation of co-pending U.S. patent application Ser. No. 08/595,802 filed Feb. 2, 1996 entitled Medical Syringe and Self Retracting Needle Apparatus, which is a continuation of U.S. patent application Ser. No. 08/565,881 filed Dec. 1, 1995, now U.S. Pat. No. 5,616,135 issued Apr. 1, 1997 entitled Self Retracting Medical Needle Apparatus and Methods, which is a continuation of U.S. patent application Ser. No. 08/455,514 filed May 31, 1995, now U.S. Pat. No. 5,549,708 issued Aug. 27, 1996 entitled Self Retracting Medical Needle Apparatus and Methods, which is a continuation of U.S. patent application Ser. No. 08/370,728 filed Jan. 10, 1995, now U.S. Pat. No. 5,480,385 issued Jan. 2, 1996 entitled Self Retracting Catheter Needle Apparatus and Methods, U.S. patent application Ser. No. 08/436,976 filed May 8, 1995, now U.S. Pat. No. 5,487,734 issued Jan. 30, 1996 entitled Self Retracting Catheter Needle Apparatus and Methods, U.S. patent application Ser. No. 08/484,533 filed Jun. 7, 1995, now U.S. Pat. No. 5,542,927 issued Aug. 6, 1996 entitled Self Retracting Syringe Needle Apparatus and Methods, each is a continuation-in-part of Ser. No. 08/370,728 filed Jan. 10, 1995, now U.S. Pat. No. 5,480,385, all disclosures of which are specifically incorporated herein by reference.

FIELD OF THE INVENTION

This invention relates generally to medical needle apparatus and methods and particularly to an apparatus comprising medical needles which are self-retracting from a fully extended position during use to a retracted position wherein the needle is fully withdrawn and encased within a housing for safe disposal. Moreover, the invention is related to medical products which may only be used once to eliminate cross contamination from one patient to another and to those medical products which have sterile parts inherently protected from contamination without the need of additional packaging.

BACKGROUND OF THE INVENTION

Problems associated with inadvertent needle sticks are well known in the art of blood withdrawal, transdermal medication injection, catheter emplacement and other medical procedures utilizing medical needles. Significant attention is placed on needle stick problems due to the contemporary likelihood of being exposed to AIDS and Hepatitis.

Procedures involving needle withdrawal typically require a technician to use one hand to place pressure at the wound site where a needle is being withdrawn, while removing the needle apparatus with the other hand. Tending technicians typically give higher priority to care for the wound than is given to disposal of a needle. This priority either requires an available sharps container within ready reach or another means for safe disposal without leaving the patient's side. Providing adequate care is often compounded by the patient's condition and mental state, for example, in burn units and psychiatric wards. Proper disposal of a used, exposed needle, while caring for a patient, is often difficult, if not impossible, under these conditions.

The widespread knowledge and history associated with needle care and their disposal problems have resulted in the conception and disclosure of a large number of devices. Though some devices describe application in the area of blood withdrawal, most contemporary related art is directed toward syringes and like devices. Related art may be broadly classified into two categories, devices which operate manually and devices which comprise self-contained needle retraction. Manual withdrawal is generally a two-handed procedure, making wound care a secondary step or requiring an added medical technician. One known self-retracting syringe results from a vacuum force, while others generally involve self-retraction resulting from the release of a cocked or biased spring.

There remains a need to provide a more satisfactory solution to the art of self-retracting needle devices.

SUMMARY OF THE INVENTION

The present invention dramatically diminishes the hazards resulting from injury-related needle sticks that occur after needle insertion procedures on patients. More specifically, the apparatus and method of this invention constitute an important advance in the art of self-retracting needle devices, as evidenced by the following objects and advantages realized by the invention over the background art.

One object of the present invention is to provide a novel and improved medical needle retracting device which protects the tip integrity and sterility of a medical needle and other internal parts of the device until use and which automatically fully retracts the needle into the housing after use.

A further object of the present invention is to provide a medical needle retracting device which is self-contained and does not require an additional container for transport Additionally, it is an object of the present invention to provide a medical needle retracting device wherein the needle retraction portion is in a relaxed state prior to use, thereby extending the useful life of the product.

Yet another object of the present invention is to provide a blood withdrawal needle safety device with an attached barrel for a blood acquisition vacuum tube, such as a VACUTAINER® blood collection tube manufactured by Becton, Dickinson and Company.

A further object of the present invention is to provide a needle cover for the device which is releasibly affixed to the housing during transport and storage of the device, but which may be frangibly separable from the housing.

Another object of the present invention is to provide a means for releasing a cocked needle assembly by distorting a portion of the housing rather than requiring a button or other mechanical device to project through the housing wall.

An additional object of the present invention is to provide protection or the portion which is distorted from being inadvertently deformed during insertion and use of the needle and to remove the protection with a single digit motion immediately prior to retracting the needle.

A further object of the present invention is to be single use only and to ensure that the needle is safely enclosed when retracted.

Yet another object of the present invention is to limit the number of injection molded parts for manufacturing ease.

Additionally, it is an object of the present invention to provide a force storing memory element which stores energy as a needle assembly of the apparatus is extended for use and which provides needle retracting force upon release of the needle assembly.

A further object of the present invention is to provide a memory element which comprises an enclosed fluid flow pathway for withdrawn blood.

Also, it is an object of the present invention to nullify forces within the apparatus which cause regurgitant flow when the needle is retracted.

It is yet another object of the present invention to provide a novel and improved IV catheter insertion apparatus comprising a housing which maintains sterility of a medical needle, a catheter and other internal parts of the apparatus until use and which automatically fully retracts the needle into the housing after use.

Another object of the present invention is to provide a means for viewing a blood "flashback" within the IV catheter device as influent blood courses into the device from a pierced blood vessel.

Additionally, it is an object of the present invention to provide a method for using a prefilled syringe wherein the trigger force for needle retraction is applied transverse to the axis of the medical needle.

A further object of the present invention is to provide a syringe and medical needle apparatus combination, wherein the syringe is prefilled prior to transport to a user and the medical needle assembly is extendable for use of the medical needle and is retractable for safe storage of the needle after use.

Another object of the present invention is to provide a powered needle withdrawal device wherein a power providing element is a compressible elastic tube.

Yet another object of the present invention is to provide a needle withdrawal device wherein a needle tip used for percutaneous skin puncture passes but once through an orifice associated with safe needle containment after use, the passage occurring only upon needle retraction.

Still another object is to provide a quick release needle-extending mechanism.

Additional objects and advantages of the invention will be apparent from the description which follows, or may be learned by the practice of the invention.

Briefly summarized, the foregoing objects are achieved by an apparatus which comprises an extendable and retractable medical needle device adapted for use in fluid collection and dispensing procedures, the device comprising a housing a medical needle at least partially disposed within the housing, an extension assembly for extending the needle from the housing to an extended state for use in a medical procedure and a release mechanism disposed on the housing for releasing the latching mechanism from the latched state, thereby, causing the energy storing member to retract the needle into the housing. The extension assembly comprises a cover for protection of the needle, an energy storing member disposed between the container and the needle such that the energy storing member stores energy as the needle is disposed for use and a latching mechanism by which the needle is latched to the housing in the extended state for use in a medical procedure. It is notable that both the energy storing member and latching mechanism are disposed in a non-stressed state prior to extending the needle and setting the device into the latched state.

The method for using the extendable and retractable medical needle device comprises the steps of storing the energy storing member and latching mechanism in a non-stressed state during a period prior to readying the needle for use, by extending the needle from the housing, and releasing the latching mechanism and retracting the needle by force of the energy stored in the energy storing member, after using the medical needle in a medical procedure. It should be noted that direction of force to release the latching mechanism is generally normal to the long axis of the needle.

BRIEF DESCRIPTION OF THE DRAWINGS

In order to more fully understand the manner in which the above-recited advantages and objects of the invention are obtained, a more particular description of the invention will be rendered by reference to specific embodiments thereof which are illustrated in the appended drawings. Understanding that these drawings depict only typical embodiments of the invention and are therefore not to be considered limiting of its scope, the presently preferred embodiments and the presently understood best mode of the invention will be described with additional detail through the use of the accompanying drawings in which:

FIG. 5 is a greatly magnified perspective view of a medical needle having a portion of the needle treated with a mold release.

FIG. 6 is an exploded side view of a blood draw device with some portions segmented and other portions removed for better presentation.

FIG. 15 is a lateral elevation of an elastic tube stretched between hubs of the barrel and needle/hub assembly parts.

FIG. 24 is a perspective view of a 3 cc syringe which is currently commercially available.

FIG. 25 is a perspective view of a retractable medical needle with a back cover removed for ready connection to a medical syringe, such as the syringe seen in FIG. 24.

FIGS. 30A–C are perspective views of molded elastic tube parts.

FIG. 33 is a cross section of the blood draw device of FIG. 31 in a cocked state and ready for use in a medical procedure.

FIG. 33A is a side elevation of a needle cover which has been removed in FIG. 33.

FIG. 41 is a magnified cross section along lines 41—41 of FIG. 38, wherein an unstretched elastic tube is disposed between a pair of tube distorting clamps.

FIG. 42 is a magnified cross section taken along lines 42—42 of FIG. 40 of the elastic tube and clamps seen in FIG. 38, the tube having been stretched and the clamps disposed about the tube to distort it from a round geometry.

FIG. 48 is a top elevation of the two part medical hub apparatus seen in FIG. 47, with one part separated from the other part.

FIG. 52 is a transverse cross section of an elastic tube and slit valve seen in cross section in FIGS. 50 and 51.

FIG. 53 is a transverse cross section of the elastic tube and slit valve seen in FIG. 52 with the elastic tube elongated to open the slit valve.

FIG. 55 is a cross section of a lateral elevation of the combination in the orientation seen in FIG. 50, but with the medical needle apparatus extended to dispose the needle for use and with a needle cover removed.

FIG. 55A is a lateral elevation of the needle cover removed from the combination seen in FIG. 55.

FIG. 62 is a cross section of a ventral portion of a combination, similar to the combination seen in FIG. 49, showing latches and catches used to limit use of the combination by forcing the needle cover deeply into the plunger part.

FIG. 67 is a front perspective of a forward needle hub seen in cross section in FIG. 64.

FIG. 67A is a rear perspective of the forward needle hub seen in FIG. 67.

FIG. 67B is a front elevation of the forward needle hub seen in FIG. 67.

FIG. 67C is a rear elevation of the forward needle hub seen in FIG. 67.

FIG. 85 is a perspective comprising an embodiment of a rear needle hub which includes a locking feature which impedes forward movement of a sheath (not shown).

FIG. 86 is a cross section of the rear needle hub seen in FIG. 85.

FIG. 87 is a cross section of an oil canning embodiment of a forward hub with oil canning disposed such that a portion of the needle extends forward from the hub.

FIG. 88 is a cross section of the forward hub embodiment of FIG. 87 but with oil canning disposed in a convex mode such that the needle is disposed rearward of the hub.

FIG. 89 is a cross section of a segment of front hub comprising an orifice filling plug for impeding forwardly directed needle travel after needle retraction.

FIG. 90 is a cross section of the segment of FIG. 89 after needle retraction.

FIG. 99 is a cross section of the device of FIG. 97 with medical needle extended and cover removed and ready for use.

FIG. 100 is a section of a rear needle hub of the device seen in FIG. 97.

FIG. 101 is a section of a central portion of the forward hub showing an asymmetric tubing connection embodiment which retards a retracted needle from reentering a needle pathway orifice in the forward hub.

DETAILED DESCRIPTION OF THE INVENTION

In this description, unless a specific object is referenced, the term proximal is used to indicate the segment of a device normally closest to the patient when it is being used. In like manner, the term distal refers to the other (away from the patient) end. Reference is now made to the embodiments illustrated in the figures numbered above wherein like numerals are used to designate like parts throughout. In some cases, parts having similar form and function to parts earlier cited are enumerated with prime numerals of the earlier cited parts. Different embodiments of the invention may be applied across the general fields of phlebotomy (blood sampling), syringes, catheters and butterfly devices.

Phlebotomy (blood sampling) Embodiments

Figure 1:
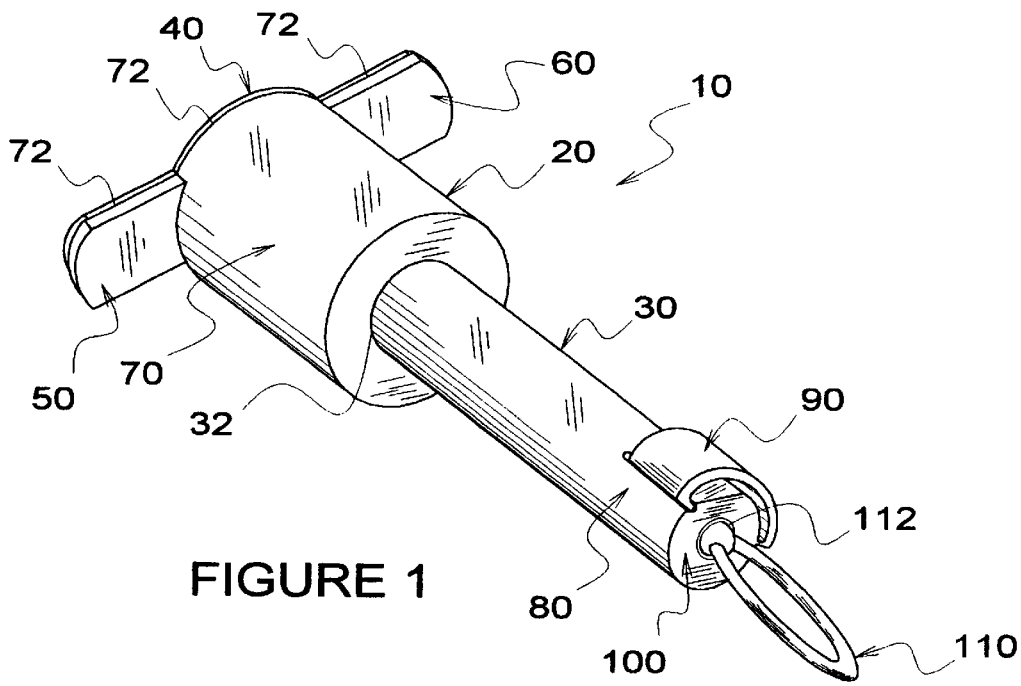
FIG. 1 is a perspective view of a sealed blood draw device, showing the exterior of the device housing.

Reference is now made to FIG. 1 wherein an embodiment according to the invention of a blood draw device 10 is seen. As seen in FIG. 1, device 10 comprises a barrel section 20 and a needle containment section 30. In a completely assembled device, section 20 is securely affixed to section 30 along circular line 32 to provide protection for contents of the device from environmental damage and contamination.

Barrel section 20 comprises a planar seal 40 and a pair of left and right ear or handle parts, designated 50 and 60, respectively, and a hollow barrel 70. Planar seal 40 is adhesively attached to barrel section 20 within a plane area defined by continuous line 72 such that the hollow of barrel 70 is maintained in a sterile condition prior to use. To use device 10, seal 40 is manually removed. Of course, a different kind of seal may be used, such as a snap-on part which may be molded as a tether-attached part of section 20. No snap-on part is shown, but production of such parts is well known in the art. A more detailed description of the internal parts of barrel 70 is provided hereafter.

Needle containment section 30 comprises an elongated tube 80, a flap 90, a proximally facing front face plate 100 and a pull-ring 110. Pull-ring 110 is separable from front face plate 100 at a frangibly detachable segment 112, which is described in more detail hereafter.

Figure 2:
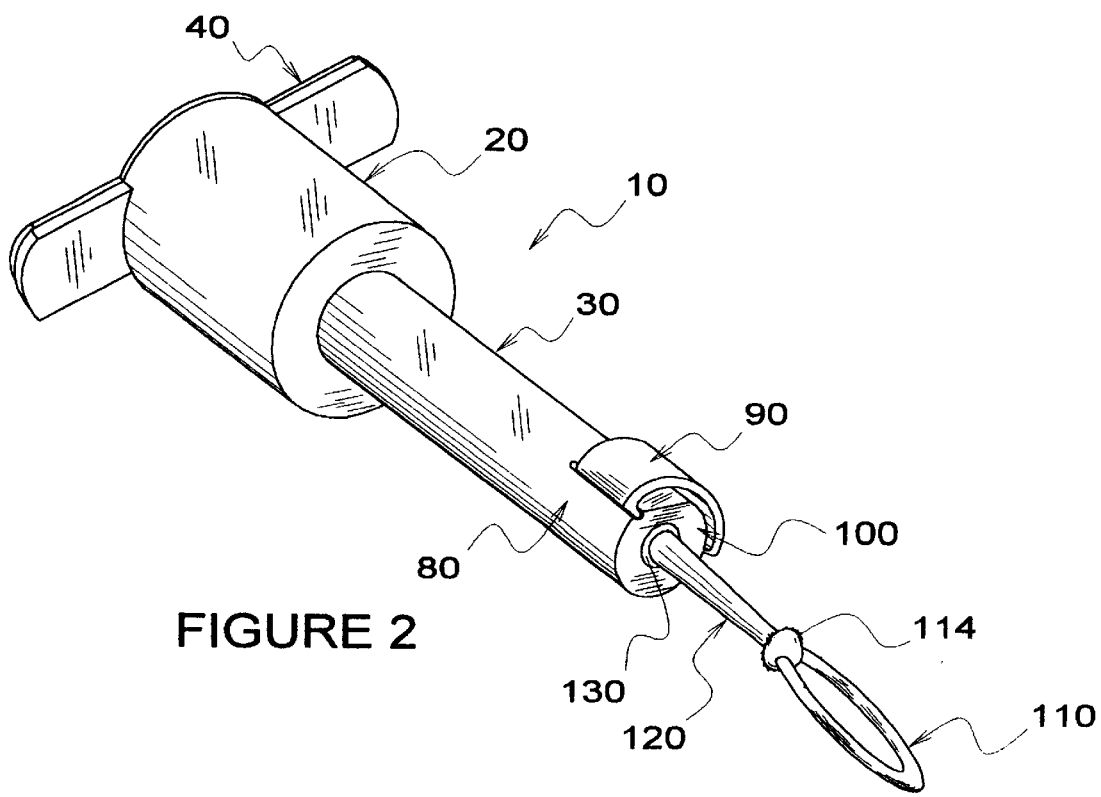
FIG. 2 is a perspective view of the blood draw device seen in FIG. 1 from which a needle cover and associated needle (not shown) have been pulled by first frangibly breaking away the needle cover from a portion of the housing.
Figure 3:
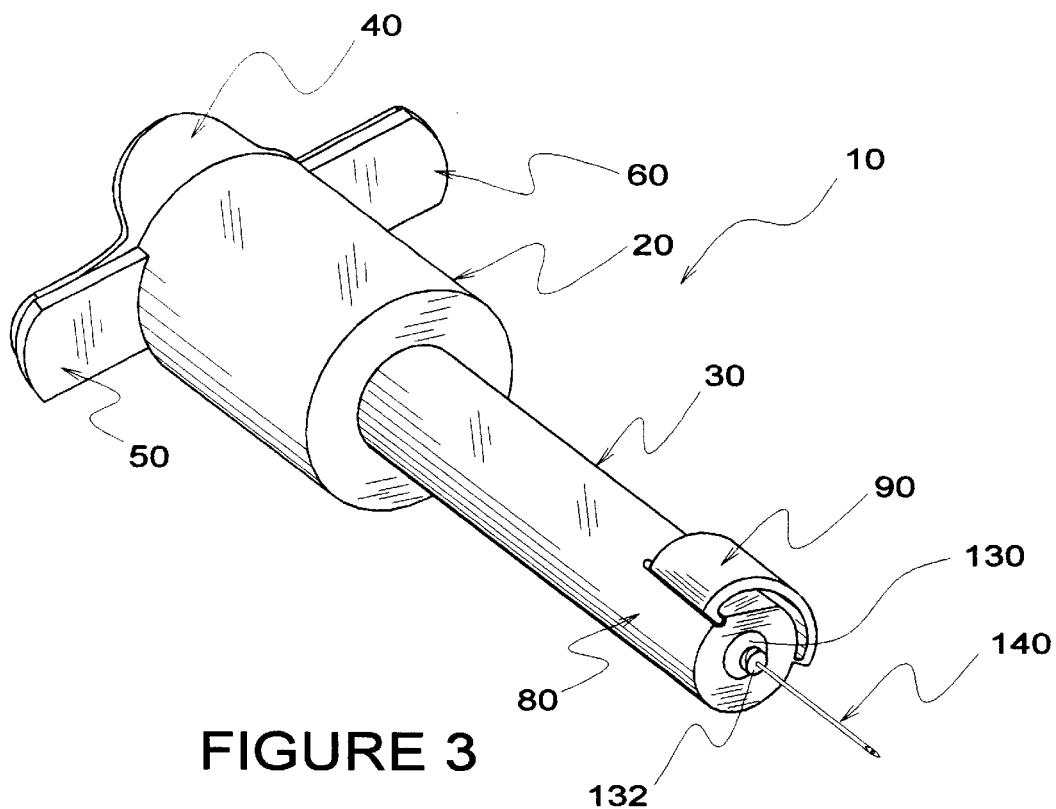
FIG. 3 is a perspective view of the blood draw device seen in FIG. 2 showing a needle bared by cover removal and a partially removed seal which covered and protected the internal portion of a blood draw vacuum tube barrel, relative to the needle.
Figure 4:
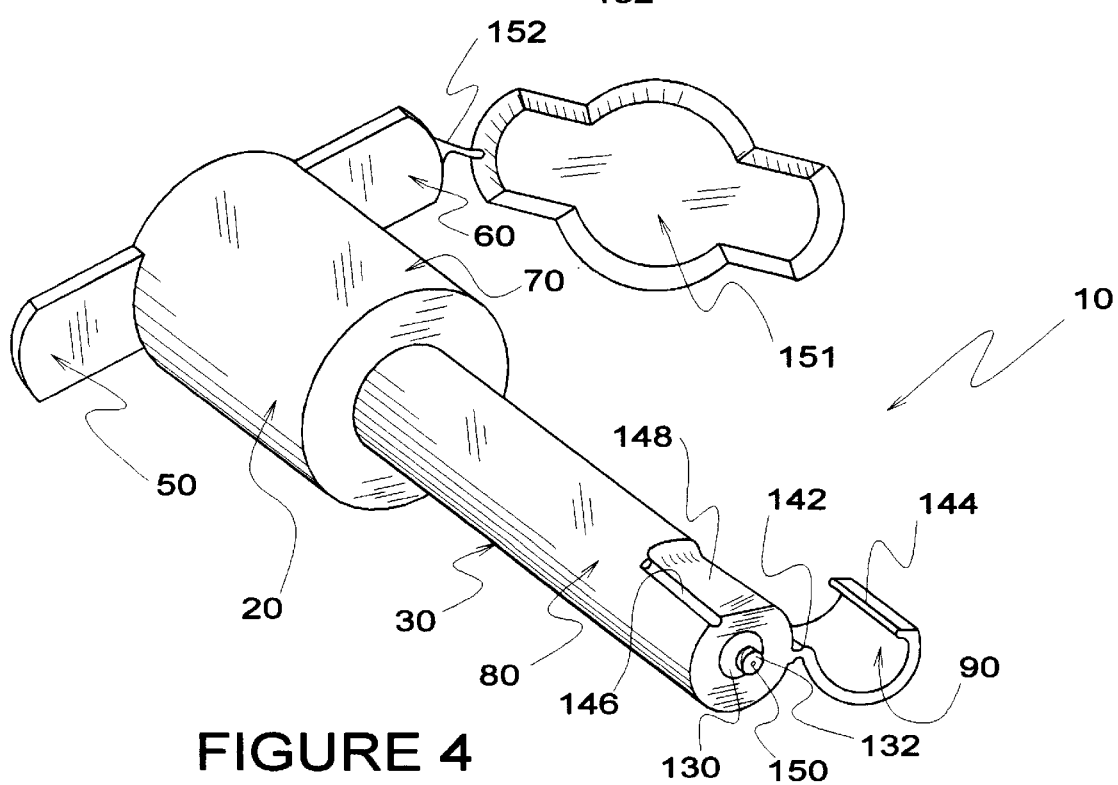
FIG. 4 is a perspective view of the blood draw device showing displacement of a flap, seen in place in FIG. 3, the displacement permitting an area of the housing previously under the flap to be distorted, the distortion resulting in retraction of the needle into the housing.

Steps related to the use of device 10 are seen in FIGS. 2–4. In FIG. 2, pull-ring 110 has been detached from front face plate 100. Detachment of segment 112 produces a ragged collar 114. As pull-ring 110 is advanced from face plate 100, a needle cover 120, which is firmly affixed and integrally molded with pull-ring 110, appears through a hole created by removal of collar 114. Once pull-ring 110 is fully extended, a yoke 130 snaps into place about the hole produced by removal of collar 114. The structure of yoke 130 and its related parts are disclosed in more detail hereafter.

A next step is to remove seal 40 from barrel section 20. FIG. 3 illustrates seal 40 in the process of being removed. In a next step, pull-ring and needle cover 120 are removed from device 10. Needle cover 120 is preferably attached to a hub 132 by a rotatably detachable coupler, such as by a threaded or bayonet type connector. In any event, the coupling attachment between hub 132 and cover 120 must be able to support a pull force of at least as great as a retarding force imposed in the opposite direction by a retracting mechanism which is energized by the pull extending cover 120 until engagement of yoke 130. As seen in FIG. 3, a hollow medical needle 140 is bared upon removal of cover 120.

As seen in FIG. 4, flap 90 comprises a living hinge attachment 142 to elongated tube 80. Flap 90 also comprises a hook latch 144 which is normally engaged in a groove 146 proximally disposed in tube 80. Located in flap 90, when disposed in groove 146, is a deformable area 148 of tube 80. While flap 90 is disposed and latched into groove 146, area 148 is fully protected from any deformation. Thus, during a medical blood draw procedure, flap 90 is latched into groove 146. Once blood acquisition has been completed, flap 90 is rotated by action of a single digit after which needle 140 may be retracted by depressing area 148. Retraction places needle 140 safely inside tube 80. The only access inside tube 80 and needle 140 is a hole 150 in hub 132 which is the essentially the same diameter as the cross sectional diameter of needle 140. Further, as is explained later, needle 140 is securely held well away from hole 150. Retraction mechanisms for needle 140 are described in detail hereafter.

Also seen in FIG. 4 is a snap-on cover 151 affixed by a tether 152 to handle 60. Cover 151 is an alternative embodiment to seal 40. Cover 151 has the advantage of not requiring a cover part to be made separately from barrel section 20. However, to provide assurance that cover 151 has not been opened previous to a procedure to which device 10 is uniquely dedicated, an additional seal, such as a shrink wrap about exterior edges of cover 151 and related parts of handles 50 and 60 and tube 80 should be used. The making of parts attached by tether is well known in the art.

Reference is now made to FIG. 6 wherein an exploded view of one embodiment of device 10 comprises a needle containment section 30, a needle-hub part 160, a valve disk 170, an elastic tube 180 and barrel section 20. Attention is first drawn to needle/hub part 160, which is shown magnified for more clarity of details in FIGS. 7–9.

Part 160 comprises medical needle 140, a fore part 190 proximal to the sharp end of needle 140, a central part 192, and an aft part 194. Normally, unseen extensions of needle 140 through part 160 is indicated by double dashed lines 196 and 198 for clarity of the extent of needle 140 passage through part 160. Fore part 190 comprises yoke 130, hub 132, annular groove 200, annular stop 202, and elbow shaped extension 204 which comprises an outwardly extending part 206. Central part 192 comprises a frangible bridge 208 and a support 210. Aft part 194 comprises a short shaft 212 and a tube hub 214. Part 160 is preferably molded as a single part with end-to-end continuity between parts 190, 192 and 194. Aft part 160 is firmly and securely affixed to needle 140, while fore part 190 is only slidably affixed and otherwise free to move along needle 140 when bridge 208 is franged. Aft part 160 may be affixed adhesively by methods which are well known in the art.

Figure 7:
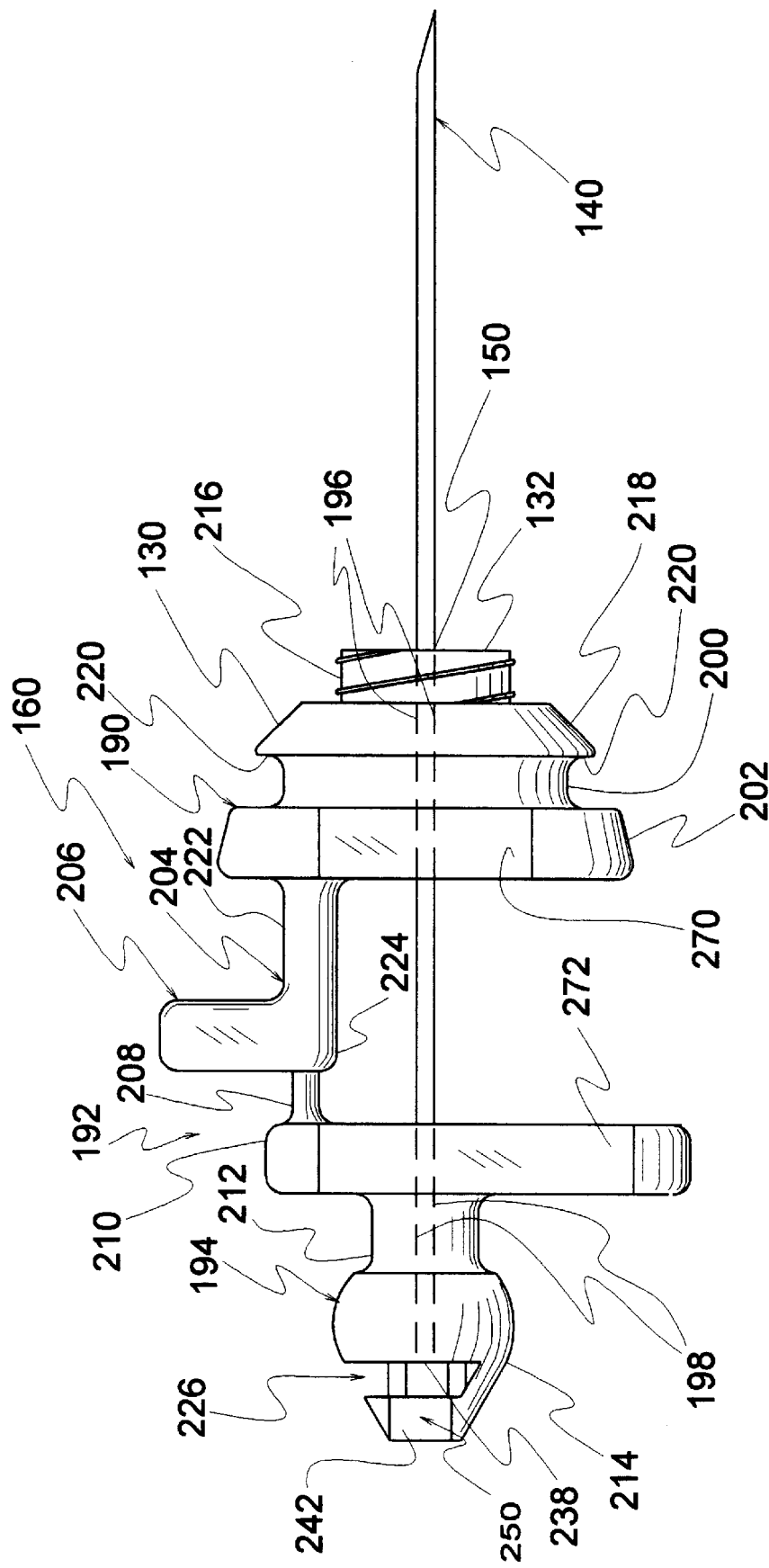
FIG. 7 is a lateral elevation of a needle/hub assembly which initially resides within the housing and is separably affixed to the cover.
Figure 8:
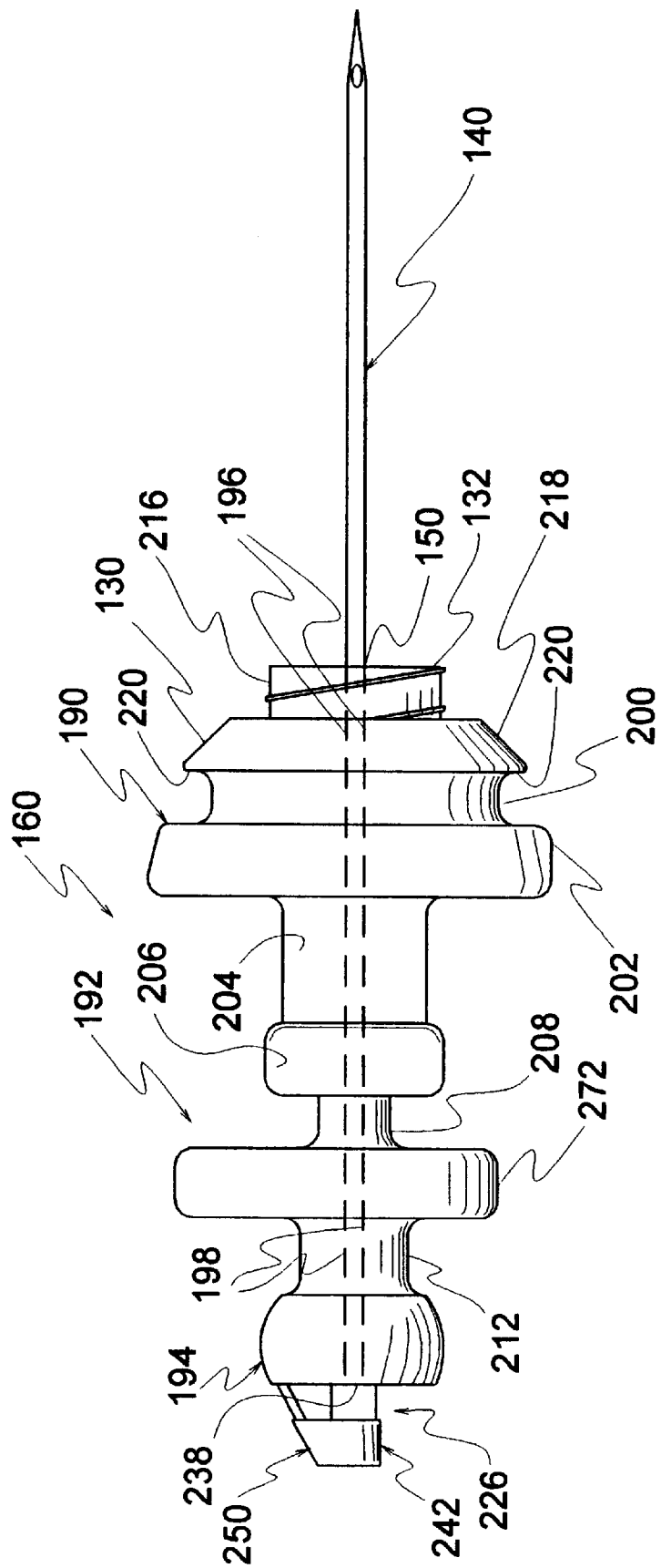
FIG. 8 is a top elevation of the needle/hub assembly seen in FIG. 7.
Figure 9:
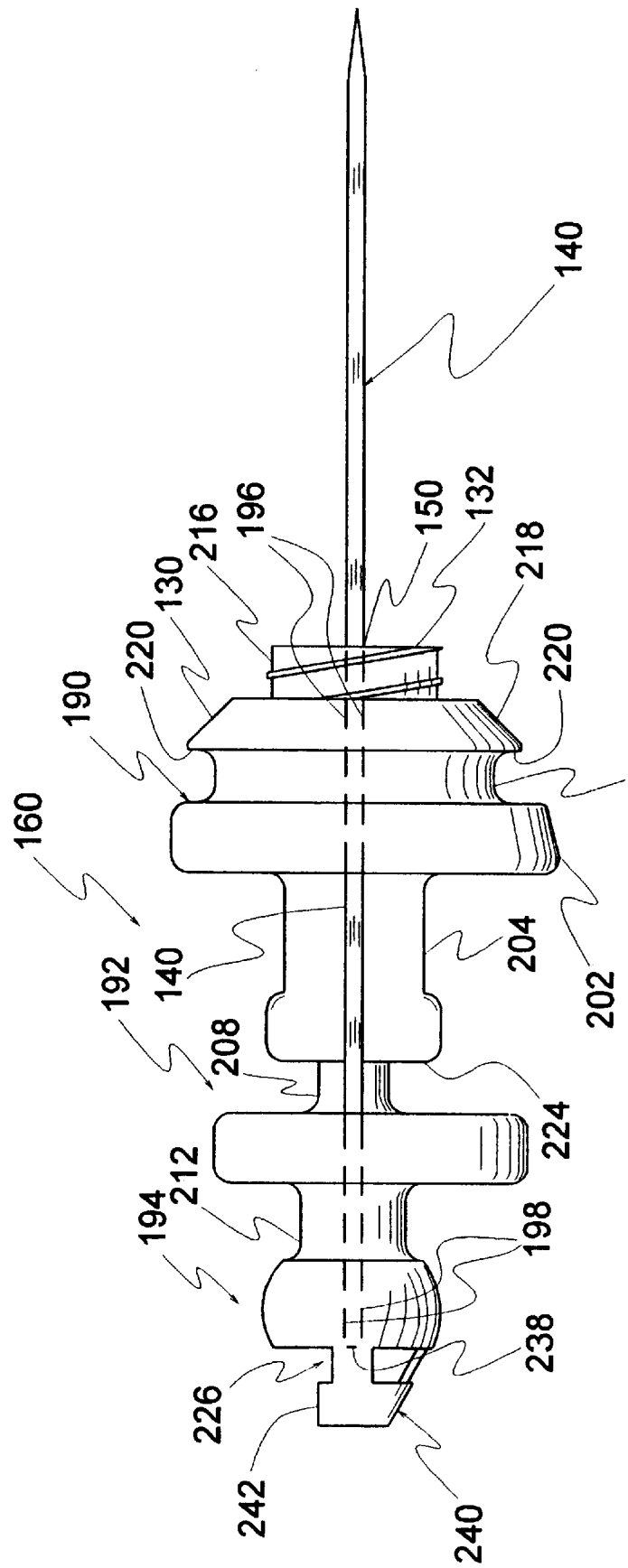
FIG. 9 is a bottom elevation of the needle/hub assembly seen in FIG. 7.

Hub 132 comprises a releasable connector component which may be in the form of a threaded surface 216 as seen in FIGS. 7–9. Yoke 130 comprises a sloped annular face 218 and a trasverse latching surface ring 220 distal to and juxtaposed to face 218. Groove 200 is interposed between and contiguous with ring 220 and stop 202. The function and use of yoke 130, groove 200 and stop 202 are described in detail hereafter.

As best seen in FIG. 7, an extension 204 protrudes distally from stop 202 via a lateral bar 222 to an elbow 224 where extension 204 makes an orthogonal bend to form upward and outwardly extending part 206. Bridge 208 is a part which is narrow in both transverse dimensions to govern the degree of pressure required to frange bridge 208 from extending part 204. One of the surprising aspects of the instant invention is the force which may be placed upon bridge 208 when pulling against a force retaining memory element used in retracting needle 140 without breaking bridge 208 away from extension 204. Clearly, if even a nominal torque is place upon bridge 208 during a pull, bridge 208 might break. Close tolerances should be maintained between needle 140 and fore part 190 to reduce and keep such torque at a level which does not cause bridge 208 to break while needle 140 is being pulled forward. The method for achieving close tolerances between needle 140 and fore part 190 is disclosed hereafter.

Bridge 208 is contiguous with a support 210. Shaft 212 is medially disposed about needle 140 and distally connected to support 210. Tube hub 214, connected to shaft 212, provides a valve leaflet containment basket 226, wherein a one-way valve leaflet may be placed and trapped by a tube mounted on hub 214. Basket 226 is better seen in FIG. 10. Basket 226 comprises a slot formed by a distal facing side 228 and a proximal facing side 230, the two sides being connected by a bottom plate 232 and two side members 234 and 236.

Side 228 is a smooth planar face comprising a non-protruding blunt end 238 of needle 140. Also shown in FIG. 10 is a valve leaflet disk 240. Disk 240 is made of compliant synthetic resinous material which, under pressure, deforms to seal end 238 of needle 140 against regurgitant flow when pressure downstream from needle 140 is greater than upstream pressure. This seal is very important to contain blood within needle 140 upon retraction of needle 140. To assure a low resistance to flow from needle 140, disk 240 comprises a plurality of raised feet which space the distal side of valve disk 240 away from side 230. That spacing and various cuts, designated 242, 244, 246 and 248 in distal end 250 of aft part 194 provide a low resistance pathway for effluent flow from a patient.

Care should be taken such that the diameter, designated by A arrows, of disk 240 is less than the sum of distances indicated by arrows B and C, but greater than B plus the diameter of needle end 238 to assure that regurgitant flow is always stopped. However, disk 240 should not be inadvertently held in an open condition by a tube stretched over hub 214.

Figure 10A:
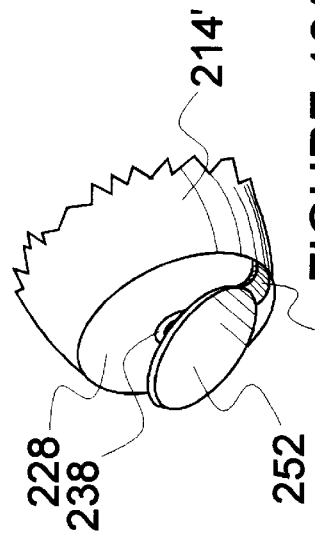
FIG. 10A is a perspective view of a section of a needle/hub assembly showing a valve leaflet affixed by molding to the needle/hub assembly through a living hinge.
Figure 10:
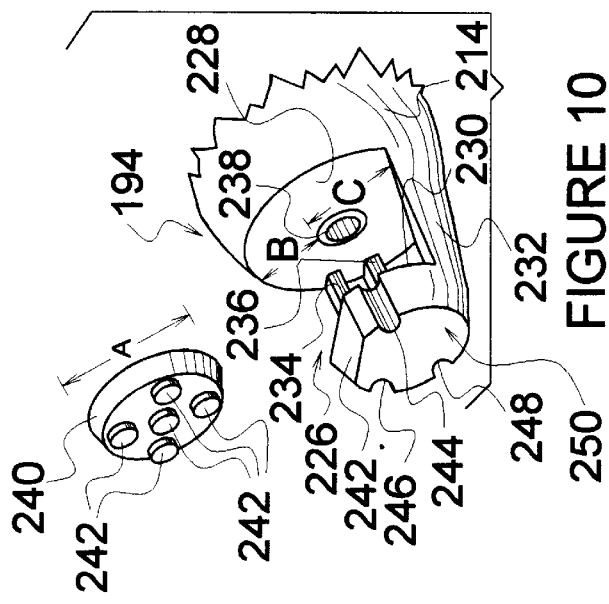
FIG. 10 is an exploded perspective of a section of the needle/hub assembly seen in FIGS. 7–9 and a valve leaflet which is used to restrict regurgitant flow from the device.

Another embodiment of a one-way valve is seen in FIG. 10A. If hub 214 is made of sufficiently resilient and compliant material, a leaflet valve may be integrally molded on the distal end of the hub. In the embodiment of FIG. 10A, a thin planar wafer 252 is integrally connected to a hub 214' (which is otherwise similar to hub 214) by a living hinge to curtail proximal flow through needle 140 at end 238 while being permissive to distal effluent flow.

In the embodiment seen in FIG. 6, retractive force is provided by a stretched tube. For this purpose, tube 180 is cut to a predetermined length allowing for displacement about a proximal and a distal hub and for a length of the tube which stretches when device 10 is cocked as needle 140 is pulled outward for use. Tube 180 comprises a proximal end 254 and a distal end 256. Tube 180 may be made from any elastic material which is effectively inert to blood and which can provide a return force sufficient to retract a needle directly from a patient into safe containment. (An elastic force in the range of two to four pounds is recommended although it has been found that a return force in the range of one pound is adequate to remove needle 140 from a patient and retract it into a housing.)

The tube should preferably be capable of being stretched at least a length of four times its resting length. However, the currently preferred material is Krayton, a proprietary material from Shell Chemical Co., available from GLS Corp., Thermoplastic Elastomers Division, 740 Industrial Drive, Cary, Ill. 60013-1962. Note that a needle of one inch in length should require a tube not greater in length than about one-half inch.

Barrel section 20 comprises a plurality of internally disposed parts, generally designated 258. Parts 258 comprise an elongated stabilizing key 260, a distal tube hub 262, an assembly plate 264, a rear delivery needle 266, and a needle cover 268.

Stabilizing key 260 is an elongated rod which stretches from assembly plate 264 to beyond stop 202 when device 10 is assembled and tube 180 is relaxed. Hub 262 is formed about needle 266 to provide a piercing entry to a low pressure collection tube (not shown) such as a VACU-TAINER® blood collection tubes (Manufactured and distributed by Becton, Dickinson and Company of Franklin Lakes, N.J.) As is standard practice in an apparatus which is used to provide entry to low pressure collection tubes, a pierceable needle cover 268 is provided to deter leakage as collection tubes are replaced.

Figure 11:
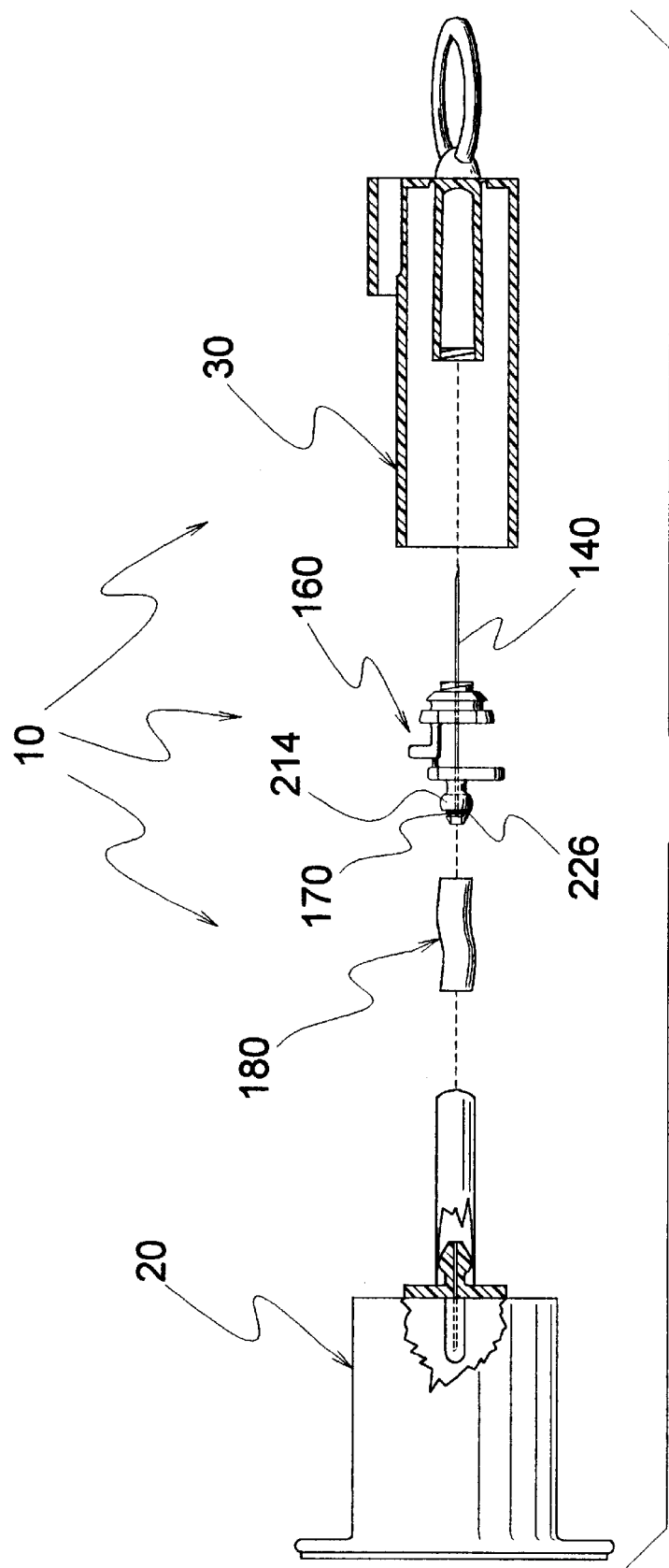
FIG. 11 is an exploded view of the device of FIG. 6 with a first assembly step completed.

FIGS. 6, 11, 12, 13 and 14 demonstrate the simplicity of assembly of device 10. FIG. 6 is representative of parts in a preassembled configuration. Step one in assembly comprises insertion of valve disk 170 into valve containment basket 226 as seen in FIG. 11. Step one is not required when a valve leaflet such as a valve formed by wafer 252 is an integral part of tube hub 214'.

Figure 12:
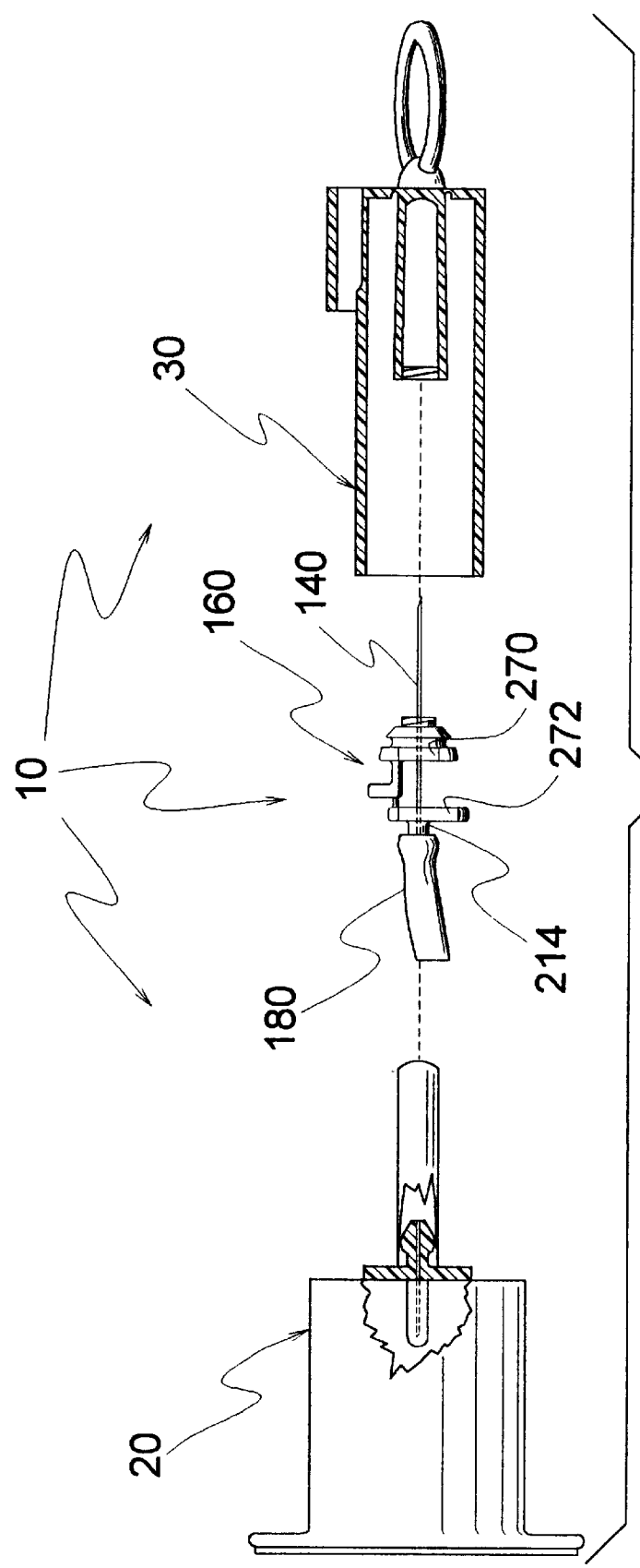
FIG. 12 is an exploded view of the device of FIG. 7 with a second assembly step, comprising attaching an elastic tube, completed.

Attachment of tube 180 to hub 214 (or hub 214' in the case of the embodiment seen in FIG. 10A) is seen in FIG. 12. To assure that tube 180 is securely affixed to hub 214 (or 214'), it is recommended that an adhesive be applied to a proximal portion of hub 214 (or 214') immediately before tube 180 attachment. A suitable adhesive material should be used and care should be taken to assure that no inappropriate blood reactive material is allowed to contact areas where blood may flow. One adhesive which has provided satisfactory adhesion in models of the invention which have been reduced to practice is Duro Super Glue, manufactured and distributed by Loctite Corporation, Cleveland, Ohio 44128, commonly known as Super Glue, although other adhesive materials known in the art may also be used within the scope of the invention. All such adhesives should be qualified to be compatible with use in a medical application.

Figure 14A:
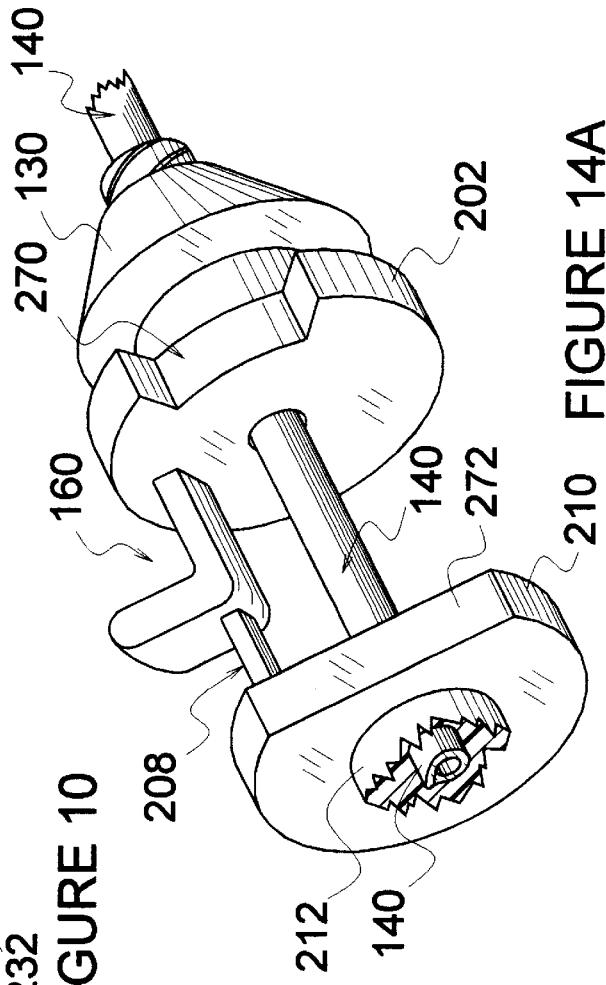
FIG. 14A is a perspective view of a needle/hub assembly with portions removed for clarity of presentation.
Figure 13:
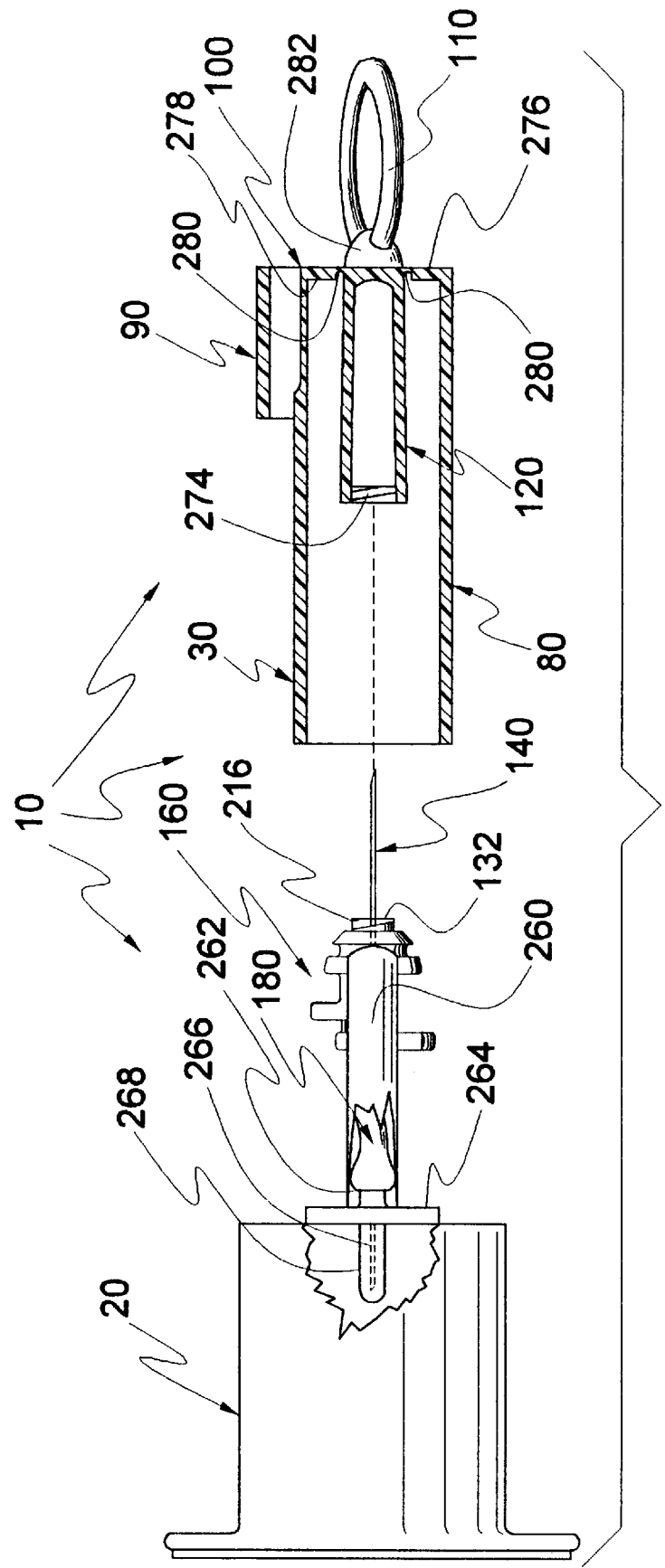
FIG. 13 is an exploded view of the device of FIG. 7 with a third assembly step of attaching the elastic tube to the barrel part. (Note that a perspective of a completely assembled device is seen in FIG. 1.)

Completion of a fluid flow path from needle 140 is seen in FIG. 13. Tube 180 is connected on distal end 256 to hub 262. At the same time stabilizing key 260 is engaged in a locking slot 270 (See FIG. 14A) disposed in annular stop 202. Key 260 is formed to slide laterally into and out of slot 270 and fit snugly therein when tube 180 is relaxed (i.e. during assembly). In this manner, no undue torque or rotational stress is placed upon frangible bridge 208 during assembly. To provide a pathway for key 260 past support 210, a material relieving flat 272 is formed along the plane of travel of key 260 in support 210.

As a next step, needle containment section 30 is disposed about the assembled parts. Needle cover 120 comprises a female connecting segment 274 which is complementary to the male connector provided by hub 216. Cover 120 is preferably affixed by rotating section 30 relative to hub 216 although press-on connections which can withstand pull forces exerted by an elongating tube or spring or the like may also be used. As needle cover 120 is connected to hub 216, tube 80 of section 30 engages assembly plate 264. Tube 80 is securely affixed to assembly plate 264 by adhesive or ultrasonic welding processes which are well known in the art of plastics assembly. In this manner, a union is provided to protect needle 140. As such, sections 20 and 30 in combination provide a housing for needle 140 which may be used without additional packaging for transport.

Attention is now drawn to front face plate 100 of section 30. Face plate 100 comprises a proximal surface 276 and a substantially distal planar surface 278. Disposed in surface 278 is an annular groove 280. Groove 280 completely encircles the area where cover 120 integrally connects to plate 100 and a ring hub 282 which is integral with the proximal end of cover 120. Hub 282 also integrally connects ring 110 to section 130. Groove 280 is of sufficient depth in plate 100 to permit facile frangible separation by a positive tug, twist or pull on ring 110 while retaining sufficient material to provide a sealed container and a sturdy and safe transport container. Products having such seals are available in commerce.

Frangibly separating ring 110 and cover 120 from section 30, as seen in FIG. 2, causes tube 180 to be stretched between separating hubs 214 and 262 as seen in FIG. 15. Needle hub part 160 and, in particular, locking slot 270 are pulled away from key 260 by the same action. For this reason, it is advisable to make groove 280 and cover 120 somewhat asymmetric to minimize rotation during tube extension. One of the material attributes which permits tube 180 to be used to store energy to retract needle 140 and to act as a pathway for fluid communication between needle 140 and needle 266, is that the internal lumen of a tube remains patent when stretched. The diameter of the lumen is reduced but not closed as the tube elongates.

Figure 14:
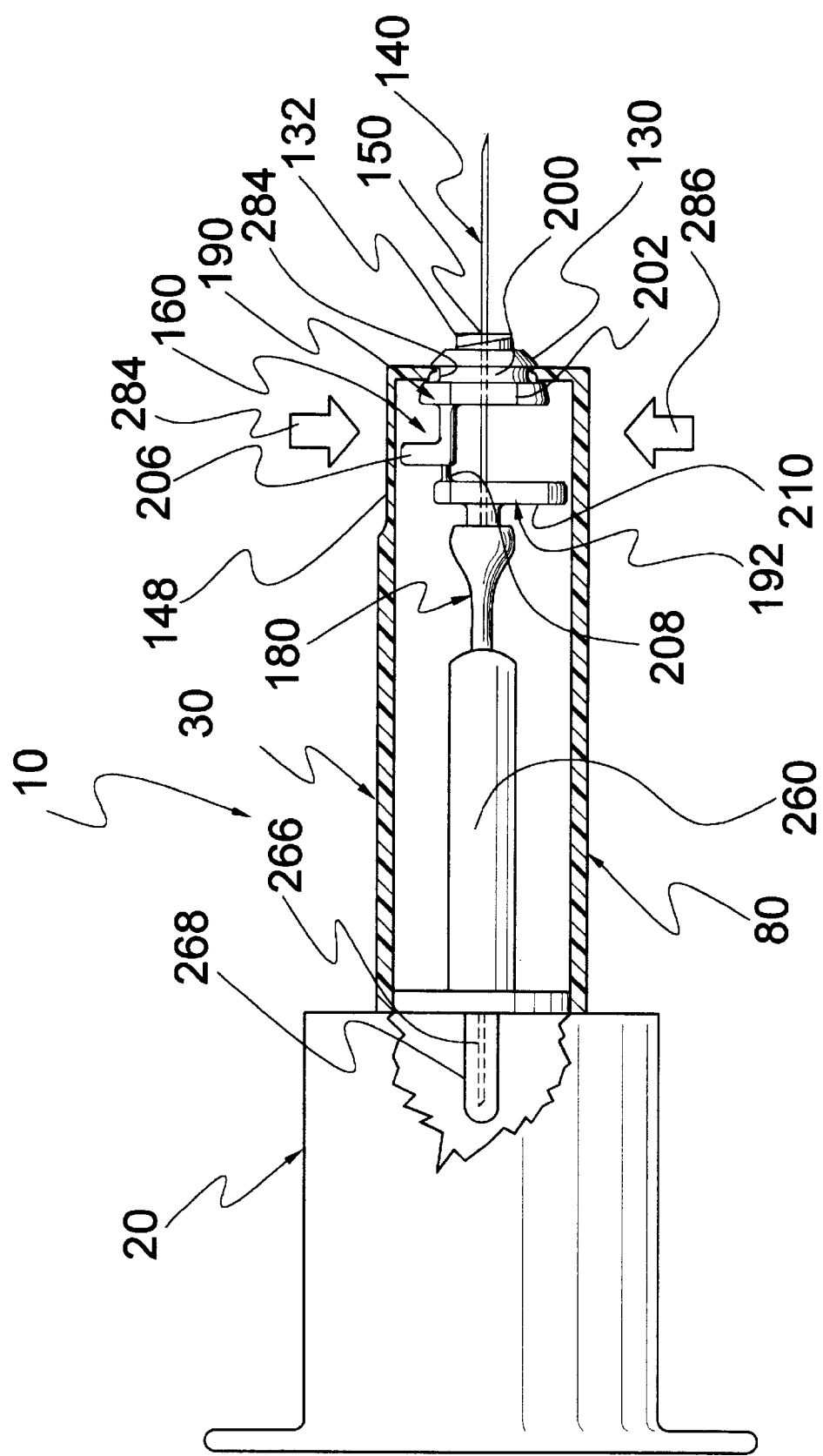
FIG. 14 is a section of a used device prior to retracting the needle.

When ring 110 and cover 120 are separated from section 30 by franging plate 100 at groove 280, an annular hole 284 is created in plate 100. As seen in FIG. 14, when needle/hub part 160 is pulled proximally, cover 120 and then yoke 130 are pulled through hole 284. The slanting annular surface 218 of yoke 130 as best seen in FIGS. 7–9, comprises a proximal diameter which is smaller than the diameter of hole 284 and a distal diameter which is larger than hole 284. However, the distal diameter is such that yoke 130 passes through hole 284 due to the "give" of material from which section 30 is made. Groove 200 has a width which permits plate 100 to be engaged therein after yoke 130 is pulled through hole 284. The proximal face of stop 202 has a diameter which is greater than hole 284 causing part 160 to be firmly affixed to plate 100 when yoke 130 passes through hole 284, as seen in FIG. 14.

Once the procedure involving needle 140 is completed, and preferably while needle 140 is yet disposed in a patient's blood vessel, needle 140 is automatically retracted. The retraction process involves (1) hingeably relocating protective flap 90 (as seen in FIG. 4) and (2) applying pressure upon part 206 through area 148 of tube 80 to frangibly separate fore part 190 from aft part 192 by breaking bridge 208 of needle/hub part 160.

Flap 90 is commonly released from attachment to tube 80 at groove 146 by inserting a thumb or finger under a portion of flap 90 and lifting. Bridge 208 is broken by applying pressure, preferably between a thumb and forefinger, in the direction of arrows 284 and 286. Franging forces (i.e. shear forces) are thus applied through area 148 to part 206 and an interior portion of tube 80 to support 210. Substantially all other forces applied to bridge 208 are those of tension caused by longitudinal stretching of tube 180. For this reason, bridge 208 comprises a geometric shape which is conducive to breaking when imposed upon by shear forces, but capable of withstanding large amounts of tension.

One of the major reasons that substantially all of the forces placed upon bridge 208 during extension of a retractive mechanism is a close tolerance held between needle 140 and fore part 190. As mentioned previously, part 190 is made to be free of needle 140 such that it can slide thereon. To maintain the tight tolerance and to provide an inexpensive method for manufacture of part 160, needle/hub part 160 is preferably molded as a unit about needle 140. Part 160 is preferably injection molded.

To permit fore part 190 to be molded about needle 140, yet remain slidably free, a thin coat of mold release is applied about needle 140 prior to molding. By applying a coat of mold release 288 in an area wherefore part 190 is molded, fore part 190 remains only slidably attached to needle 140. Of course, at the distal end 290 of needle, aft part 194 is firmly and securely affixed by the molding process causing needle 140 to be retracted when tube 140, attached to aft part 194, is permitted to contract. When needle 140 is retracted through yoke 130 and hub 132, the only access into tube 80 is through hole 150, which has substantially the same diameter as needle 140. Of course, once needle 140 is retracted, it is irretrievably held inside tube 80 by a relaxed tube 180.

Except for needle 140, which is made of medical grade steel, needle/hub part 160 is made from a moldable material having sufficient tensile strength to withstand pull pressures of device 10, yet be facilely separated at bridge 208. As such, part 160 is preferably made of a synthetic resinous material, such as polyurethane, polypropylene or polyethylene. For an experimental device, the synthetic resinous material used was polyurethane sold as Quik Cast distributed by TAP Plastics, Dublin, Calif. 94568. However, many commercially available materials may be used within the scope of the invention.

Barrel section 20 is likewise preferably made from synthetic resinous material. Barrel section 20 is also preferably molded about rear delivery needle 266. The same material which is used in commercially available barrels for vacuum based blood drawing tubes (e.g. VACUTAINER® blood collection tubes) may be used. Needle cover 268 may be one of the same as VACUTAINER® blood collection tube barrel needle covers now commonly used.

Needle containment section 30 is preferably made by a single molded process. Mold material should be selected such that it provides sufficient material strength to engage and hold the hub 132 connection through the pull process, sufficiently flexible when made as a thin membrane to permit distortion sufficient to break bridge 208, and fangible for facile opening as at groove 280. The material is preferably a synthetic resinous material and may be polyethylene, although other materials meeting flexibility, medical compatibility and strength requirements may be used.

Figure 16:
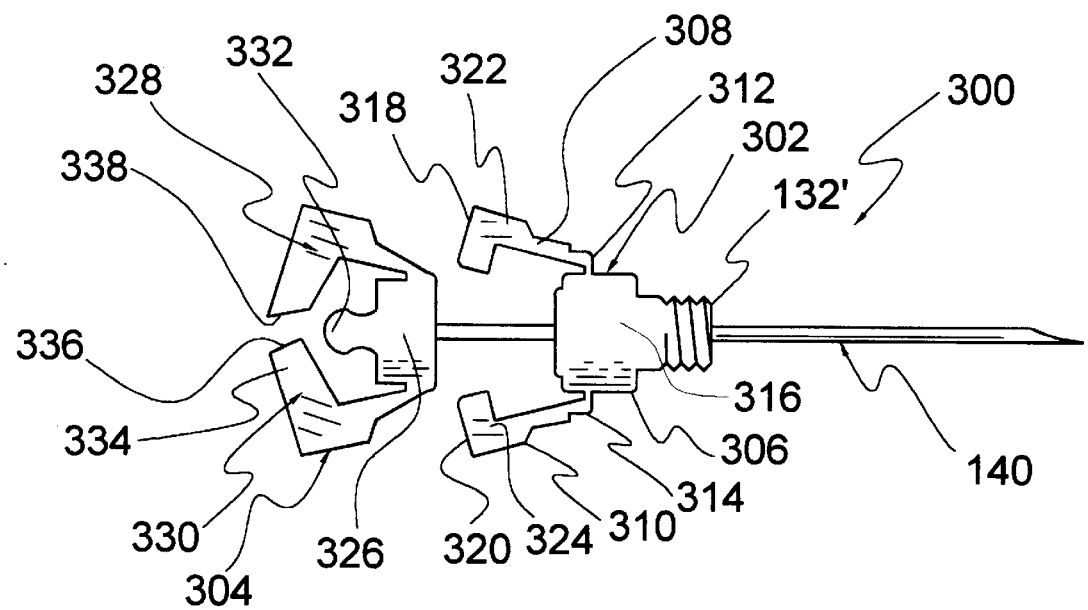
FIG. 16 is a side elevation of an alternative embodiment of a needle/hub assembly showing a first part which is molded about and securely affixed to the needle and a second part which is molded about the needle but which is free to slide longitudinally along the needle.

Reference is now made to FIGS. 16–20 which relate to another embodiment of the invention. This embodiment is similar to the embodiment seen in FIGS. 6–14 in general form and function, but does not depend upon a frangible part to release and retract the needle. As seen in FIG. 16, a needle/hub assembly 300 comprises two parts, designated fore-part 302 and aft-part 304, which are formed about a needle 140. Parts 302 and 304 may be molded about needle 140 simultaneously. Part 302 is preferably molded about a segment of needle 140 to which a mold release has been applied, as earlier described. (See FIG. 5.)

Fore-part 302 comprises a central body 306 and a pair of outwardly extending wings or arms, individually designated 308 and 310. Each arm 308,310 is connected to central body 306 by a biased hinge 312 and 314, respectively. The biasing of hinges 312 and 314 is preferably formed as a part of the molding process. Such hinges are well known in the art (as an example, note the hinges on telephone connectors). Each arm 308,310 is biased to extend outwardly from central body 306 a predetermined distance. Disposed at the outer end 318, 320 of each arm 308, 310, respectively, is an inwardly projecting latching extremity 322, 324.

Central body 306 comprises a cover connecting hub 132', which is similar in form and function to hub 132. A portion 316 is disposed distal to hub 132', where hinges 312 and 314 are attached.

Aft-part 304 comprises a central body part 326, a pair of outwardly extending and biased wings or arms 328 and 330 and a tube hub 332. Wing 330 comprises an inwardly projecting strut 334, which ends at a clamping face 336. In opposing fashion, wing 328 comprises an inwardly projecting jaw 338. Function and use of the various parts of fore-part 302 and aft-part 304 are disclosed in detail hereafter.

Figure 17:
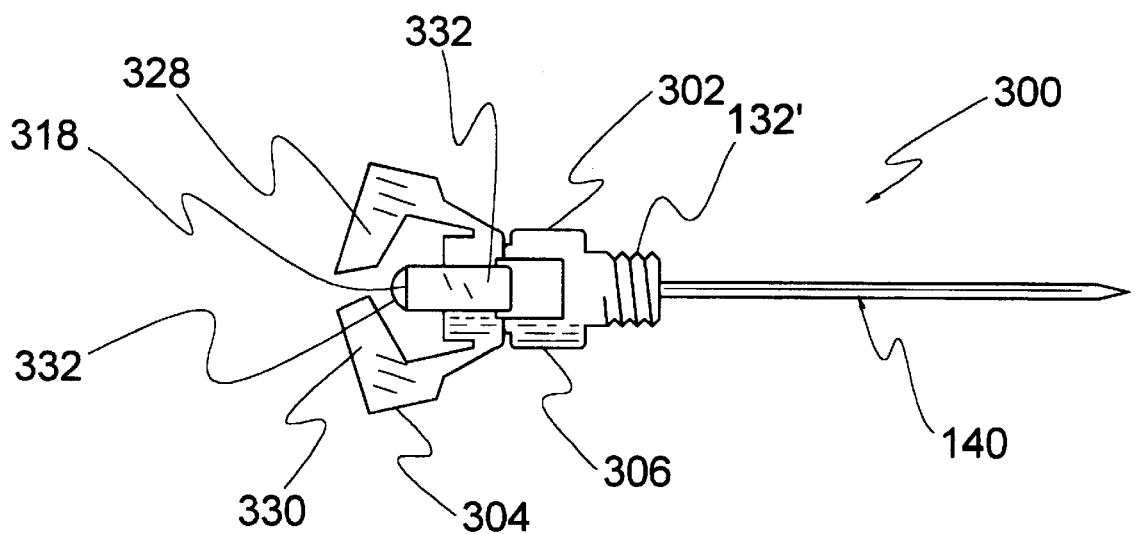
FIG. 17 is a side elevation of the embodiment seen in FIG. 16 with the slidable part moved to an adjoining position relative to the first part.

As mentioned earlier, fore-part 302 is preferably molded about needle 140, but not attached thereto, except by the natural engagement provided by materially surrounding the circumference of a portion of the needle. This permits fore-part 302 to be rotated 90° and moved into linkable proximity with aft-part 304 as seen in FIG. 17.

Figure 21:
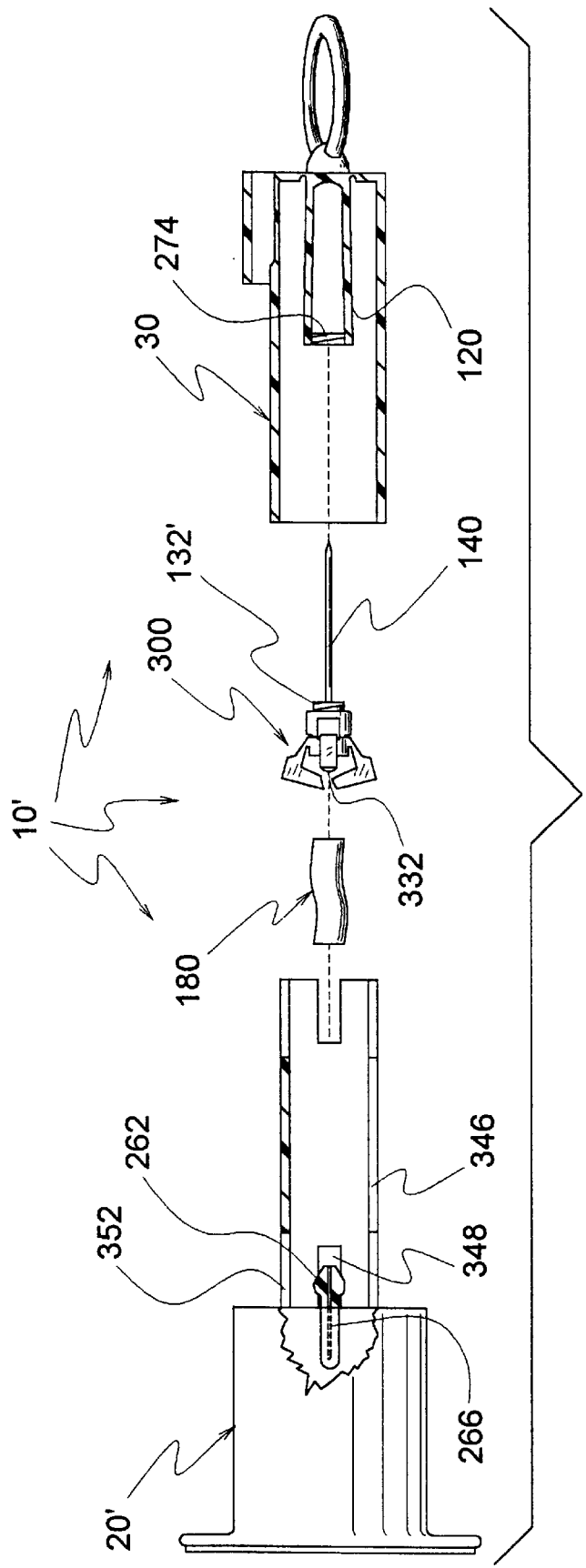
FIG. 21 is an exploded perspective view of the device comprising the alternate needle/hub embodiment.

The parts content in this second embodiment of blood draw device 10 is best seen in FIG. 21. This second embodiment comprises a barrel section 20', tube 180, needle hub assembly 300 and needle containment section 30.

Barrel section 20' is substantially the same as barrel section 20 except for the substitution of a guide-catch cylinder 340 integrally and medially disposed on a fore portion of barrel section 20' rather than a stabilizing key similarly disposed upon barrel section 20.

Figure 20:
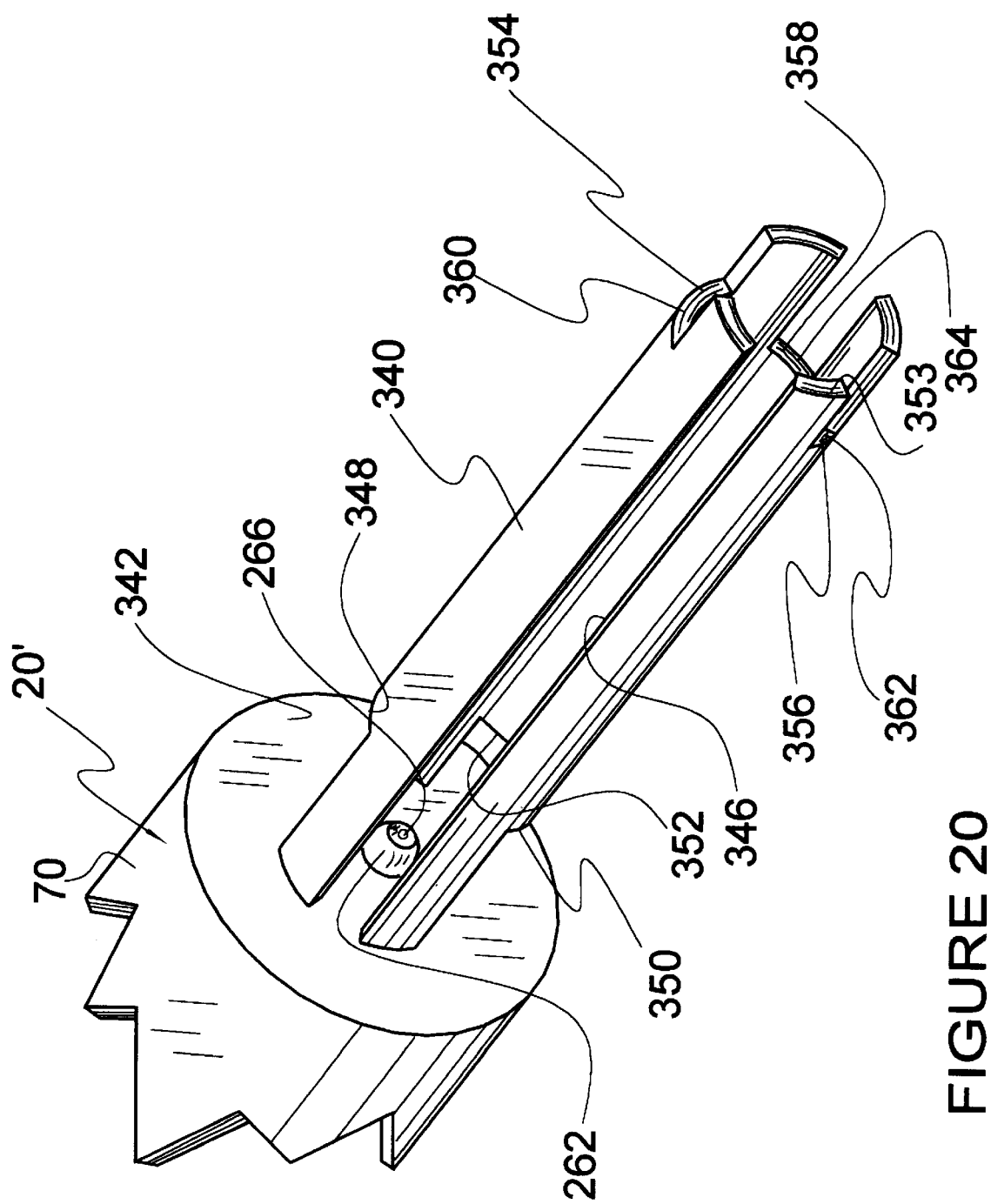
FIG. 20 is a perspective view with some parts removed for clarity of a barrel section associated with the embodiment seen in FIGS. 16–20.

Guide-catch cylinder 340 is best seen in FIG. 20. As seen therein, barrel 20' comprises barrel 70, a substantially closed fore face 342 of barrel 70, distal needle hub 262 providing access to needle 266, and guide-catch cylinder 340. Guide-catch cylinder 340 is medially disposed upon face 342 and extends in elongated fashion in line with needle 140 (not seen in FIG. 20). Hub 262 is medially disposed inside cylinder 340 along the same line.

Cylinder 340 comprises a plurality of slots which provide relief for outwardly biased members of parts 302 and 304, travel guide for assembly 300 and catch stops which selectively maintain parts of assembly 300 in a proximal position while the needle is in use. A first slot 346, disposed to act as a guide, extends the length of cylinder 340. In this embodiment, device 10 is assembled to dispose a portion of wing 330 in slot 346.

Disposed at its distal end, cylinder 340 comprises a second slot 348 offset at 90° from slot 346 and having a length which is adequate for relief from compression of wing 308, when assembly 300 is distally disposed before use. Likewise, cylinder 340 comprises a third slot 350 similar to slot 348 and juxtaposed 180°, therefrom, to provide relief from compression of wing 310. A fourth slot 352 of cylinder 340 is distally disposed 180° from slot 346 and provides before-use relief from compression for wing 328. If an outwardly biasing material is used in the manufacture of assembly 300 which does not take a set after time between assembly and use, it is not necessary to provide slots 348, 350 and 352.

Cylinder 340 provides openings for four slots at its proximal end 353, i.e., slots 346, 354, 356 and 358. As mentioned earlier, slot 346 provides a guide for assembly 300 by containment of wing 300. Longitudinally slots 354 and 356 are respectively aligned with slots 348 and 350. Slot 354 comprises a catching edge 360 for end 318 of wing 308, while slot 356 comprises a catching edge 362 for end 320 of wing 310. Slot 358 is aligned with slot 352 and provides a catching edge 364 for wing 328, as described in detail hereafter. Each slot has a depth such that in combination latch portions of wings 308, 310 and 328 occur substantially simultaneously.

Figure 18:
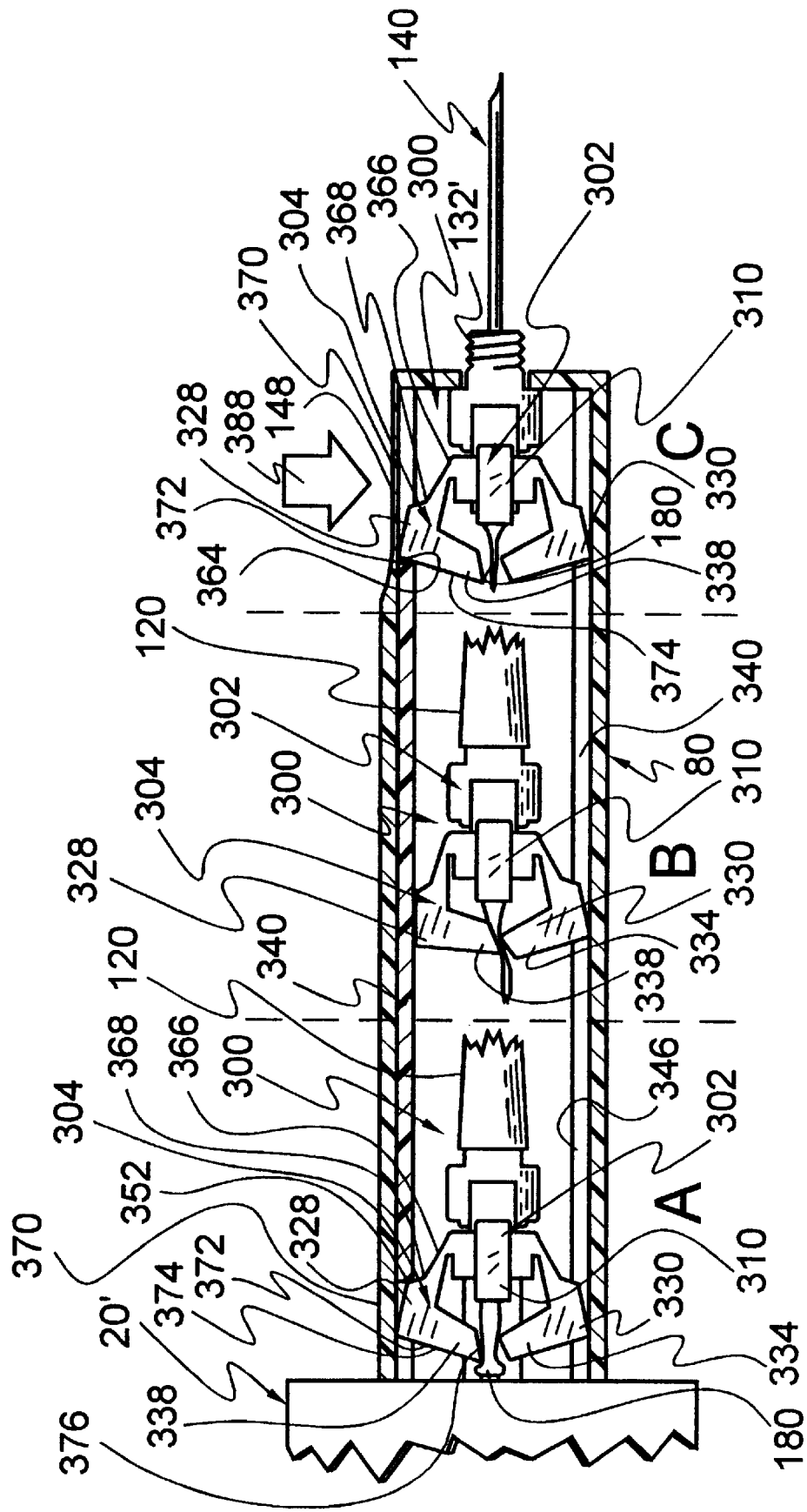
FIG. 18 is a longitudinal section of a portion of the device showing the alternate needle/hub embodiment in three different positions in the device.
Figure 19:
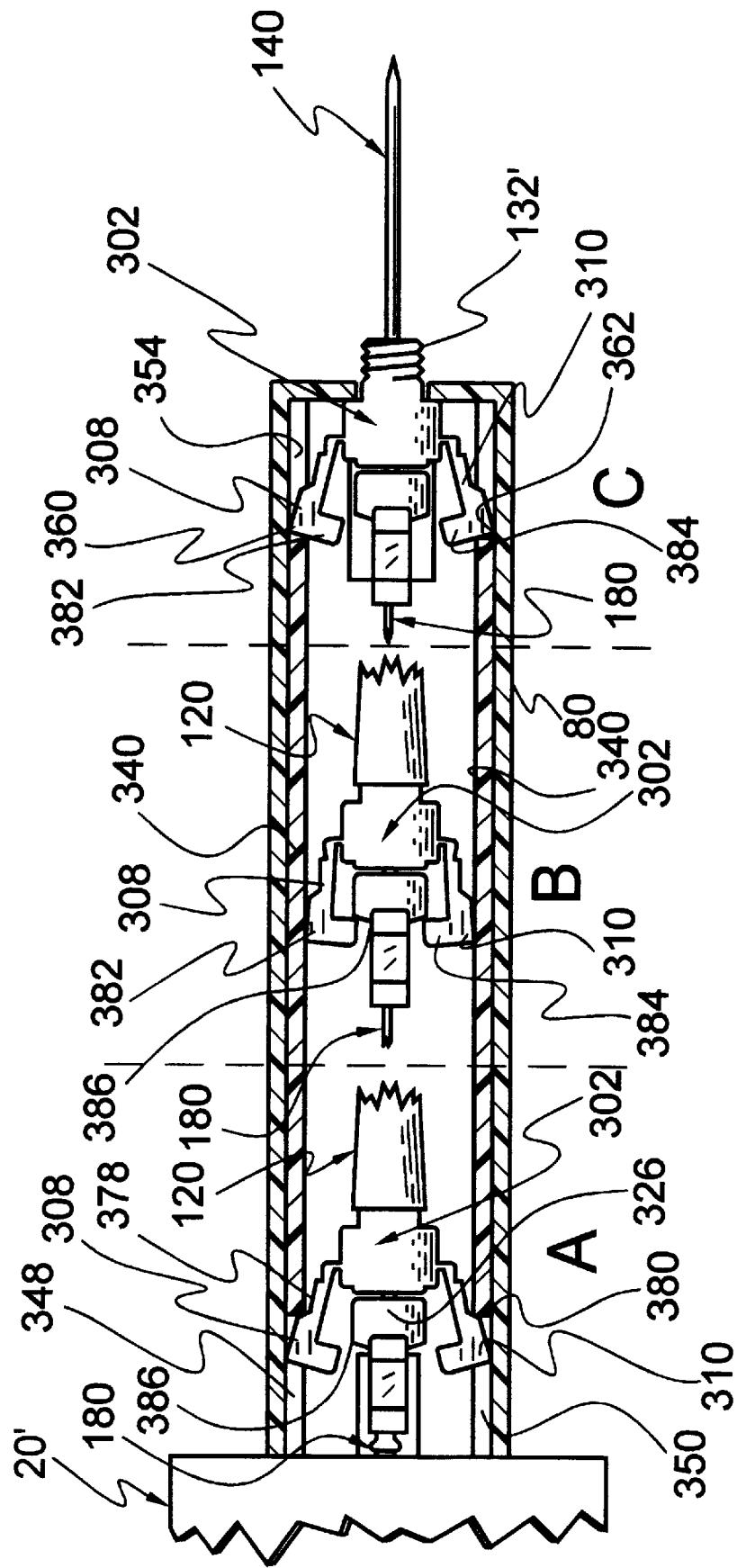
FIG. 19 is a section similar to the section seen in FIG. 18, but rotated 90°.

The latching operation of the elements of assembly 300 is best seen in FIGS. 18 and 19. Each of FIGS. 18 and 19 are divided by dashed lines into three sections (A, B and C) to demonstrate operation of fore-part 302 and aft-part 304 of assembly 300 at different positions along the length of cylinder 340. Note that wings 328 and 330 are vertically disposed in FIG. 18. Wings 308 and 310 are vertically oriented in FIG. 19, as parts of assembly 300 in FIG. 19 are rotated by 90° relative to parts in FIG. 18.

It is particularly important to note that wing 328, as seen in FIG. 18A and 18C, extends superiorly from central body part 326 along a line 366 to pivot arcuately upward at arc 368 to join a superior line 370. Further, line 370 ends at a latch point 372. From latch point 372, the shape of wing 328 is further defined by an inwardly progressing line 374 and an acutely connected line 376 which, in combination, demarcate jaw 338.

As seen in FIG. 18A, assembly 300 is residing distally within cylinder 340 and tube 80, and wing 330 is free to move in the longitudinal direction of needle 140 guided by slot 346. In the same assembly 300 position, wing 328 is disposed in an uncompressed or relaxed state within slot 352. When assembly 300 is pulled proximally to a cocked and useful state as seen in FIG. 18C, assembly 300 passes through an intermediate state seen in FIG. 18B. As assembly 300 is moved proximally from the state seen in FIG. 18A, the form of wing 328 formed along arcuate line 368 permits wing 328 to be collapsed, such that line 370 of wing 328 coincides with the cylindrical inner surface of cylinder 340. In this manner, the aft-part 304 of assembly 300 is facilely allowed to move through cylinder 340.

Compression of wing 328, as seen in FIG. 18B, causes jaw 338 to compressively pinch tube 140, thereby stopping any flow of liquid therethrough while wing 328 is between slots 352 and 358. Moving assembly 300 proximally to the position seen in FIG. 18C permits wing 328 to be once more relieved as it is biased to enter slot 358. Once there, a latch formed at latch point 372 and along line 374 is caught by edge 364, firmly retaining assembly 300 with tube 140 in a stretched condition.

Referring now to FIG. 19, device 10 has been rotated 90° clockwise relative to a view of the needle 140 end of the device. In FIG. 19, wings 308 and 310 are vertically oriented. Each arm 308, 310 resides in a non-compressed state in slots 348 and 350, respectively. Arm 308 comprises an arcuate surface 378, similar to the wing 328 arcuate surface along line 368, which provides a facile release from slot 348. Arm 310 comprises a similar surface 380 for facile release from slot 350.

As assembly 300 is pulled proximally from the state seen in FIG. 19A to the state seen in FIG. 19B, arms 308 and 310 are compressed inwardly. Each arm 308 and 310 comprises a latching foot, respectively designated 382 and 384, which engages and grips a distal annular surface 386 of central body 326. In this manner, fore-part 302 is releasibly adjoined to aft-part 304, while assembly 300 is pulled forward to a cocked position. In its most proximal position, arms 308 and 310 are outwardly biased into slots 354 and 356, respectively. In this position, feet 382 and 384 catch against edges 360 and 362 to form a permanent latch thereat. Note that outward biasing of arms 308 and 310 release the grasp of feet 382 and 384 against surface 386, thereby releasing the grip of aft-part 304 by fore-part 302.

When the grip of aft-part 304 is so released, needle 140 is relieved of proximal containment in tube 80 when aft-part 304 is triggered to a released state to be distally displaced by contraction of tube 180. Referring once more to FIG. 18C, aft-part 304 is released from a cocked state by depressing area 148 in the direction of arrow 388. Such depression forces wing 328 inward until the part of wing 328 along line 374 and latch point 372 clears edge 364. Contraction of elastic tube 180 retracts aft-part 304 and needle 140, to which the aft-part is securely affixed, into the distal section of tube 80 seen in FIG. 18A. Fore-part 302 remains proximal in tube 80 to effectively plug the hole formed by removal of hub 282 and collar 114. Note that fore-part 302 comprises a threaded hub 132', similar to hub 132.

Reference is now made to FIG. 21, showing an exploded view of the parts which are comprised in the alternate embodiment seen in FIGS. 16–20. The alternate embodiment parts comprise barrel section 20', tube 180, needle hub assembly 300 and needle containment section 30.

Assembly of the parts seen in FIG. 21 into a complete needle retracting device 10', which is functionally equivalent to device 10, involves the following steps:

1. Affixing tube 180 to hub 332;
2. Biasing wings 308,310 and 328 inwardly and sliding assembly into cylinder 340 for engagement with slots 348, 350 and 352, respectively;
3. Affixing tube 180 to hub 262. Note that access to hub 262 is provided through slot 346;
4. Laterally displacing section 30 such that the threaded connecting segment 274 of needle cover 120 engages hub 132';
5. Rotating section 30 to affix hub 132' to needle cover 120 (assembly 300 is restrained from rotating because wing 330 is disposed in slot 346 both during assembly and cocking procedures;
6. Affixing section 30 to section 20', preferably by application of adhesives or by ultrasonic welding to form a hermetically sealed package about needle 140.

A Catheter Embodiment

Figure 22:
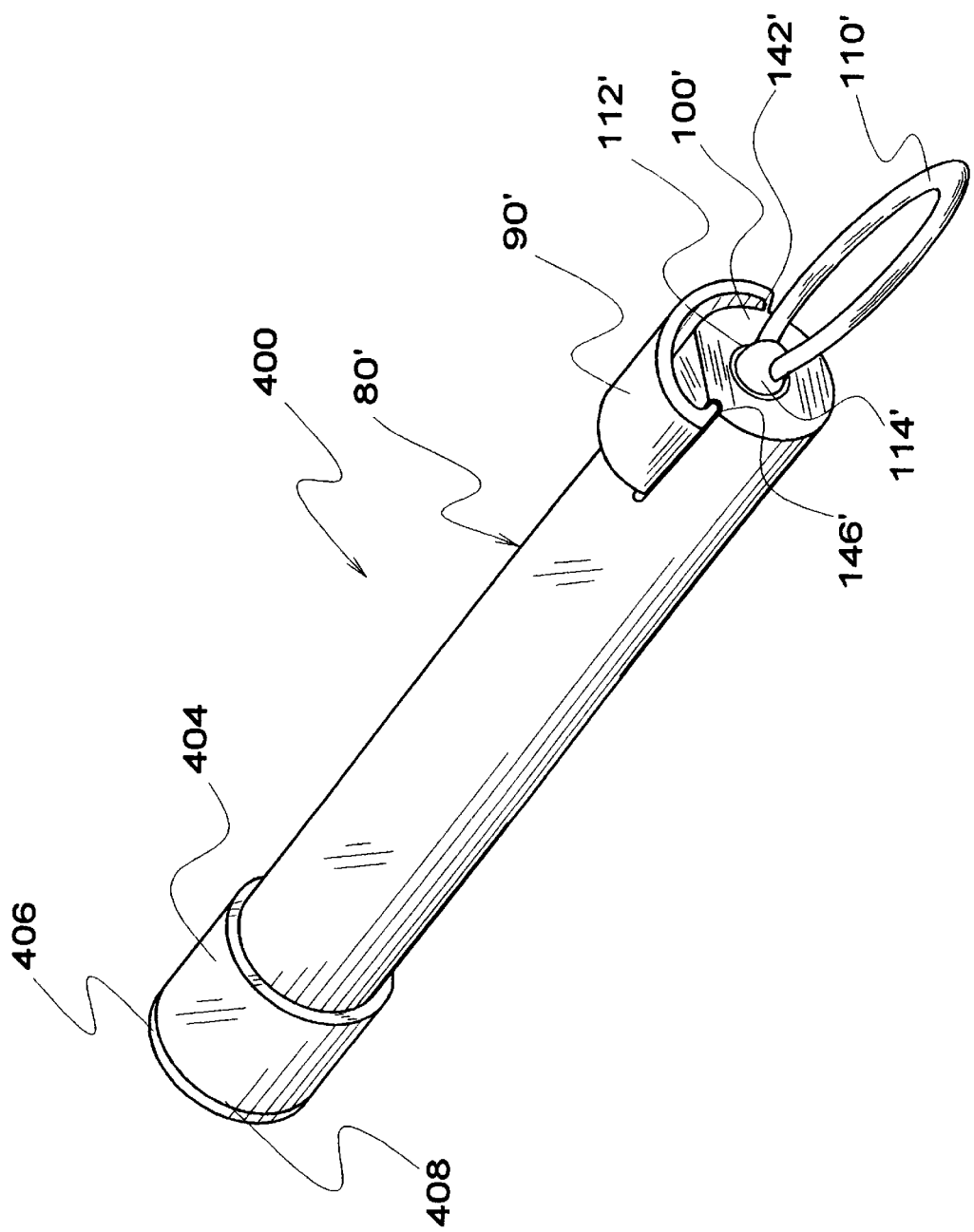
FIG. 22 is perspective view of an alternate embodiment of the invention showing a totally enclosed IV catheter insertion assembly.
Figure 23:
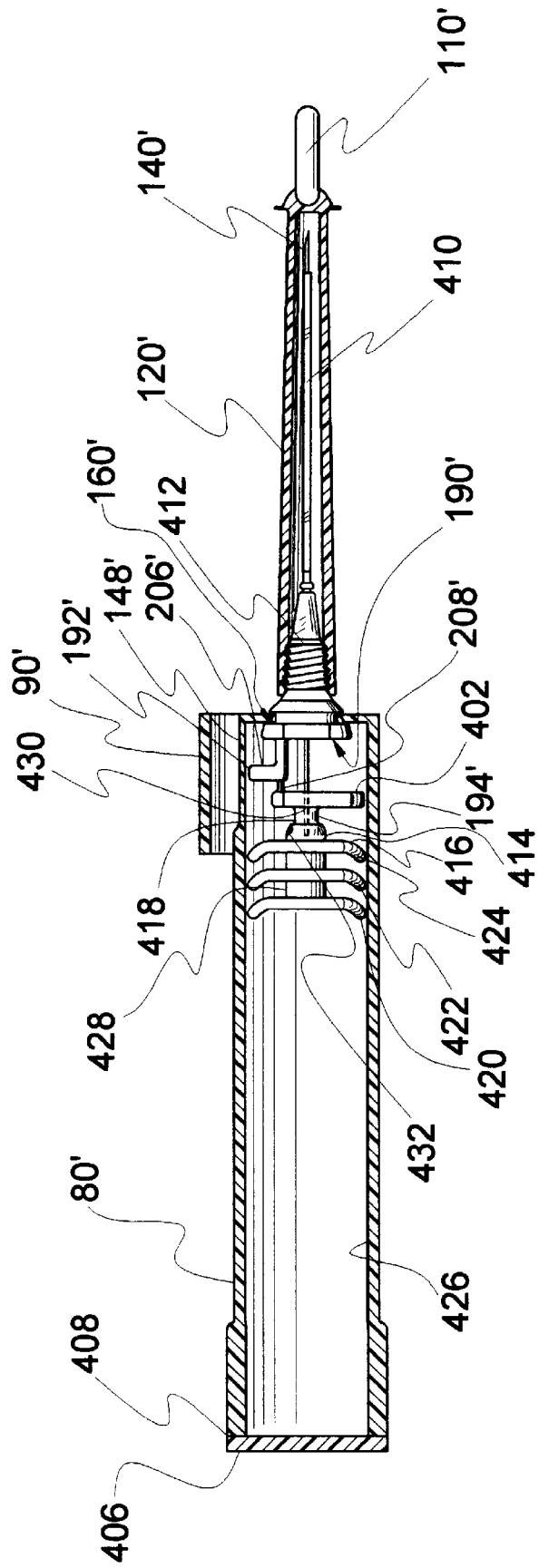
FIG. 23 is a longitudinal section of the assembly seen in FIG. 22.

Reference is now made to FIGS. 22 and 23 illustrating a catheter insertion apparatus 400, which is another embodiment of the invention. A closed, transport compatible package of apparatus 400 is seen in FIG. 22. Exteriorly, apparatus 400 is seen to comprise a pull ring 110' affixed to and integral with a front face plate 100', which is similar to face plate 100. Face plate 100' is integral with a tube 80' which is also similar in form and function to tube 80. Face plate 100' also comprises an annular frangible segment 112' which permits ring 110' and a collar portion 114' of plate 100' to be frangibly separated from plate 100' when pulling a needle assembly proximally from tube 80' for use.

Tube 80' comprises a flap 90' similar in form and function to flap 90, which is releasibly affixed to a groove 146' and on an opposite end attached by a living hinge 142' to tube 80'. Tube 80' is elongated to fully contain a needle 140' used in catheter insertion and a needle draw mechanism 402, as seen in FIG. 23.

At its distal end, tube 80' comprises an annular raised section 404, which acts as a handle during the needle pulling procedure. Further, apparatus 400 comprises a distal plate 406 which is securely affixed at the distal end 408 of tube 80' to enclose and hermetically seal needle 140' and withdrawal mechanism 402 inside tube 80'.

Withdrawal mechanism 402 comprises a needle/hub part 160', which is similar to part 160 in form and function. Basic ways in which part 160' departs from the form of part 160 is found at the proximal and distal segments of part 160'. Proximally, part 160' comprises a secondary connection 412 for a transcutaneous catheter 410.

Such catheters and catheter connections are well known in the transcutaneous catheter art. Also needles used with transcutaneous catheters are readily available. A common source is Becton, Dickinson and Company of Franklin Lakes, N.J. 07417-1883. A current source for such catheters is Abbot Hospitals, Inc., North Chicago, Ill. 60064. The material from which tube 80' and plate 406 is made is similar to the materials prescribed for tube 80.

Distally part 160' comprises a connection 414 whereby a return energy storing component 416 is affixed to a hub 418 portion of part 160'. As seen in FIG. 23, part 160' comprises catheter needle 140', a fore part 190' proximal to the sharp end of needle 140', a central part 192', and an aft part 194'. With the exceptions of proximal and distal connections of mechanism 402, parts 190', 192' and 194' are substantially the same in form and function to parts 190, 192 and 194. A bridge part 208' and upwardly extending part 206', each being respectively similar in form and function to bridge 208 and part 206, are similarly inwardly disposed for compressible access via a depressible area 148' of tube 80'.

Markedly different, although within the scope of the invention, is return energy storing component 416. Component 416 comprises a plurality of piston head parts 420, 422 and 424, which communicate with an inner wall 426 of tube 80' to effectively pull and retain a vacuum as the mechanism is moved proximally. The vacuum contained in tube 80' provides the force which retracts needle 140' when bridge 208' is frangibly broken. To provide an adequate retraction force, parts 420, 422 and 424 must create a differential force sufficient to overcome forces of stiction in both the needle and other retracting mechanisms. For apparatus 400 to have substantially universal use, a minimum atmospheric pressure of ten pounds per square inch is assumed. As an example, for a minimum pressure of four pounds realized from an atmospheric pressure of ten pounds per square inch, each part 420, 422 and 424 must have a minimum area of four tenths of a square inch. As parts 420, 422 and 424 are essentially circular planes, their diameter must be a minimum of 0.36 inches (0.9 centimeters). However, for some retracting pistons, only on the order of two pounds of force have been required. In such lower force requirement cases, a proportionate reduction in part 420, 422 and 424 size is possible.

Parts 420, 422 and 424 are securely affixed to a medially disposed piston hub 428, which is in turn likewise affixed to mechanism 416 via aft part 194'. As indicated by dashed lines 430, needle 140' communicates with hub 428 via part 194. Hub 428 is a hollow vessel which is completely sealed, except for a gas communicating plug 432 disposed proximal from part 424.

Plug 432 is made from a hydrophobic material which is permissive to passage of gas (air), but retards flow of water based liquids (such as blood). The preferred material is a sintered, ultra high molecular weight polyethylene having a particle size on the order of 10 microns, a material available from POREX Technologies, 500 Bohannon Road, Fairbum, Ga. 30213. Plug 432 is securely affixed to hub 428 to provide a pathway for gas to relieve pressure as blood is communicated into hub 428 through needle 140'.

Hub 428 is made from either translucent or transparent materials through which blood may be seen. Thus, by providing the pathway from needle 140' into hub 428 and permitting air to escape from hub 428 as influent blood arrives, hub 428 provides a visually determinable blood "flash", which is commonly used to ascertain entry of needle 140' into a blood vessel.

To use apparatus 400, ring 110' and collar 114' are frangibly separated from plate 100'. Needle cover 120', needle 140', and catheter 410 are pulled from tube 80', until mechanism 402 is firmly attached to plate 100'. By this action a vacuum is created in the portion of tube 80' which is distal to part 420. Cover 120' is removed and needle 140' and catheter 410 are transcutaneously inserted into a patient following good medical practices. When needle 140' enters a blood vessel, blood is communicated to hub 428 through which a blood "flash" indicates to the attending technician that the vessel has been entered. At this point, flap 90' is lifted to provide access to area 148'. A portion of area 148' is depressed to frangibly break bridge 208', which releases the aft portion 194' of mechanism 402 to be retracted by force stored via parts 420, 422 and 424 in cooperation with tube 80'. Needle 140' is thereby withdrawn. The only pathway through which blood may be communicated upon withdrawal of needle 140' is into tube 80'. This limitation upon needle withdrawal is a definite advantage over non-self-retracting needle systems currently in use. Under appropriately controlled conditions, catheter 410 is removed for attachment of other medical devices.

A Syringe Embodiment

Reference is now made to FIGS. 24 and 25 wherein a standard commercially available 3 cc syringe 500 is seen in FIG. 24 and a self-retracting medical needle assembly 510 is seen in FIG. 25. Syringe 500 comprises a male luer fitting 512 and a female luer lock connector 514 disposed at an end of an elongated syringe barrel 516. Male fitting 512 comprises a fluid flow lumen 518, through which fluid is communicated between barrel 516 and a medical needle.

Assembly 510 comprises a housing 520, a female luer lock connector 522 and a needle cover 524 extending outward from housing 520 at an end of housing 520, which is distal from luer lock connector 522. Cover 524 comprises a thinned section 526 and an enlarged end 528 which, in combination, provide a section which may be easily grasped between a thumb and forefinger to pull cover 524 from housing 520.

Figure 26A:
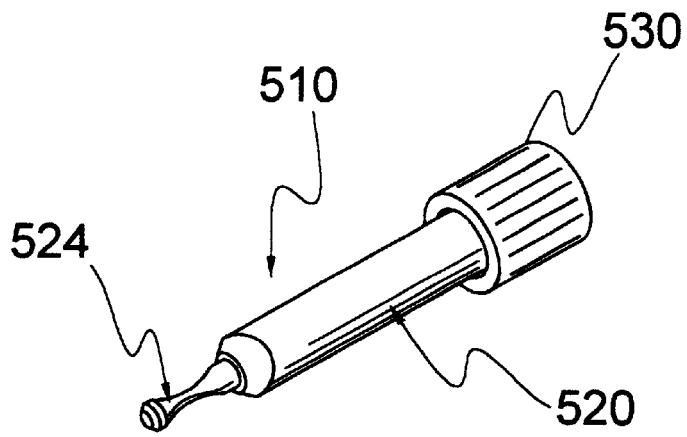
FIGS. 26A–D are perspective views of the retractable medical needle assembly in various stages of use.

Steps involved in using assembly 510 are best seen in FIGS. 26A–D. An "off-the-shelf" embodiment of assembly 510, with an aft portion covered by a cap 530, is seen in FIG. 26A. Cap 530 preferably comprises a male luer lock thread similar to female luer lock connector 514 for secure attachment to luer lock connector 522 of housing 520. In place for transport, cap 530 also is frangibly connected to housing 510, preferably by a connection process known in the plastics molding art as heat staking. Similarly, cover 524 is preferably frangibly connected to housing 520 by heat staking.

Figure 26B:
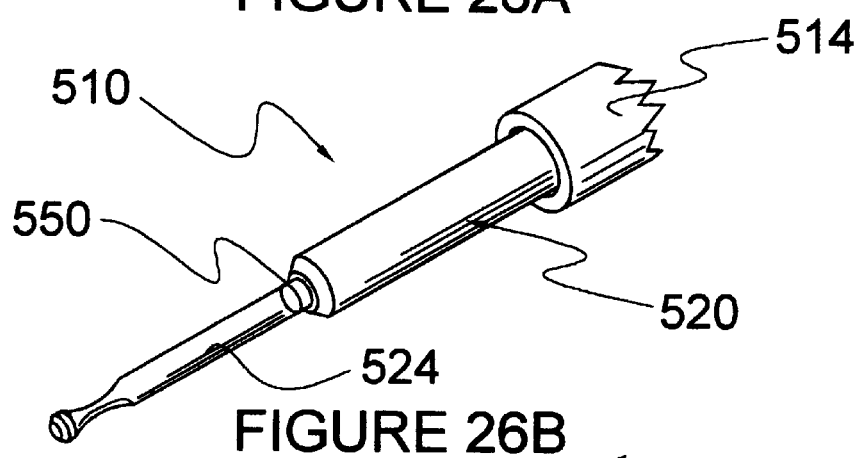

After assembly 510 is connected to a syringe, seen in part by a section of female luer lock connector 514 in FIG. 26B, cover 524 and a medical needle 540 (seen in FIG. 26C) are pulled from housing 510. Cover 524 is preferably frangibly separated from housing 510 to permit cover 524 and needle 540 to be so extended.

Figure 26C:
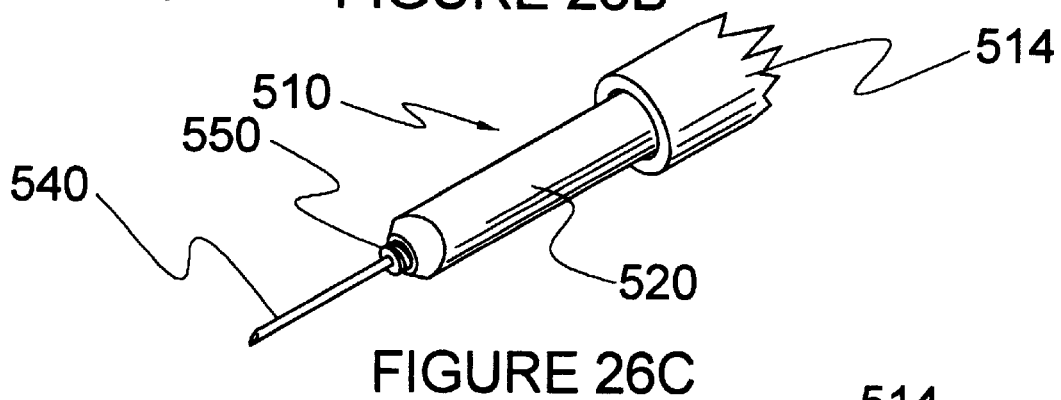
Figure 26D:
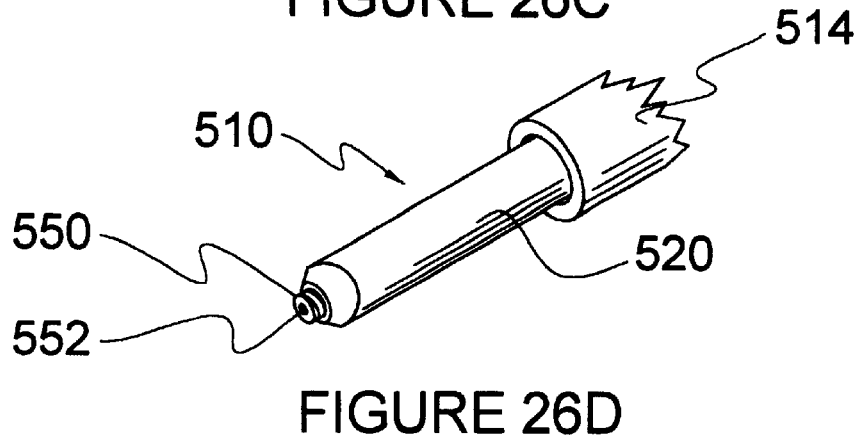

As seen in FIG. 26C, cover 524 is removed (preferably by a quarter-turn twist) to expose medical needle 540. Also exposed is a first hub 550 which rides upon needle 540, but which is slidably free from needle 540 when needle 540 is retracted.

After a medical procedure, medical needle 540 is retracted, by releasing a latch from a catch (disclosed in detail hereafter), back into housing 510. Lumen 552, through which needle 540 refractively travels, is the only opening which remains at the fore-end of housing 510 upon needle retraction. Following retraction, medical needle 540 is completely and safely contained inside housing 510, thereby permitting simple procedures for safe disposal.

Figure 27:
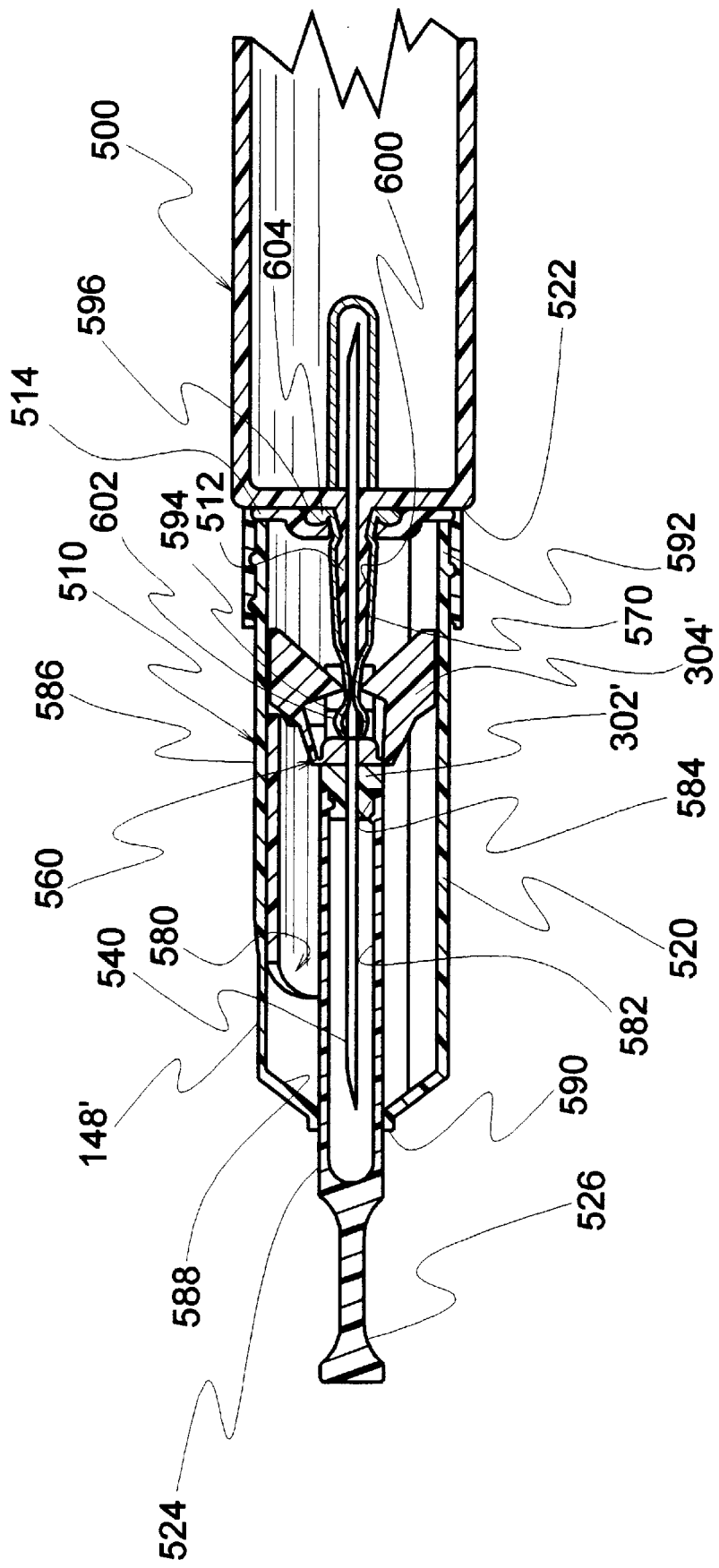
FIG. 27 is a magnified lateral elevation section of the medical needle assembly.

Reference is now made to FIG. 27 in which one embodiment of syringe needle assembly 510 is seen in cross section, greatly magnified. A syringe 500 is affixed to assembly 510 by a female luer lock connector 514. As described earlier, female connector 522 is threaded into luer lock connector 514 to firmly, but releasibly affix assembly 510 to syringe 500.

In addition to cover 524 and housing 520, assembly 510 comprises a medical needle hub assembly 560, an elastic tube member 570 and an inner housing member 580. As disclosed heretofore, cover 524 comprises a thinned section 526 which provides for facilely gripping cover 524 to pull it and needle 540 from housing 520. Cover 524 also comprises an elongated hollow barrel section 582 in which needle 540 is protectively enclosed prior to use. At an end 584 which is distally disposed from thinned section 526, cover 524 comprises a coupler 584 which releasibly attaches to hub 550. Such an attachment is preferably threaded.

Housing 520 comprises an elongated cylindrically shaped barrel 586 and orifice 588 disposed at a needle exit and reentry end 590 of barrel 586. At an end 592, which is distal from end 590, barrel 586 comprises a blunt transverse termination. Disposed near the exit and reentry end 590 is a deformable area 148' (similar in form and function to area 148, described heretofore). To accomplish the fimction of area 148', housing 520, cover 524 and inner housing member 580 are made from a pliable synthetic material, such as polypropylene. Though not seen in FIGS. 25–28, one should understand that a flap similar to flap 90 may be added to housing 520 to protect area 148' from being inadvertently depressed prematurely.

Medical needle hub assembly 560 comprises medical needle 540, a fore hub part 302' and an aft hub part 304'. Hub parts 302' and 304' are similar in form and function to parts 302 and 304, respectively, and are therefore denoted by primes of the earlier named hub parts. Parts 302' and 304' comprise essentially all of the features of parts 302 and 304. The major difference between each part 302, 304 and 302', 304', respectively, is size. Parts 302' and 304' are much smaller than respective parts 302 and 304 to permit the size of assembly 510 to be compacted to a diameter which is consistent with the radial diameter of connector 514. Assembly 560 also comprises an elastic tube hub 594 disposed at an end of needle 540 distal from its sharpened end. Similar to parts 302 and 304, parts 302' and 304' are preferably made from resilient, synthetic resinous material.

Rather than using separate parts, such as parts 302' and 304', medical needle hub assembly 560 may comprise a single hub similar to needle/hub part 160 or 160'. In such a case, the hub similar to needle/hub part 160 or 160' is frangibly separated to retract needle 540 into housing 520.

Inner housing member 580 is similar in form and function to cylinder 340 relative to providing forward catches for parts 302' and 304'. Inner housing member 580 comprises catches for wings of parts 302' and 304' and a back plate 596. As may be seen in FIG. 29, back plate 596 comprises an annular groove or recess 598 which forms a catch for a circular lip 604 of elastic tube 570. A catch edge 360', similar to edge 360 which forms a catch of cylinder 340, forms a catch for a wing of part 302'. A similar catch is on the other side of inner housing 580, but is not seen in FIG. 29.

Reference is now made to FIGS. 27–30A–C, wherein elastic tube member 570 is seen. Elastic tube member 570 may be made from medical grade latex, silicone rubber or any other elastic tubular material which is reasonably inert and non-injurious to blood In such materials, elastic tube member 570 may be fabricated by molding, extruding or dipping methods which are well known in the art of elastic part manufacturing.

Figure 28:
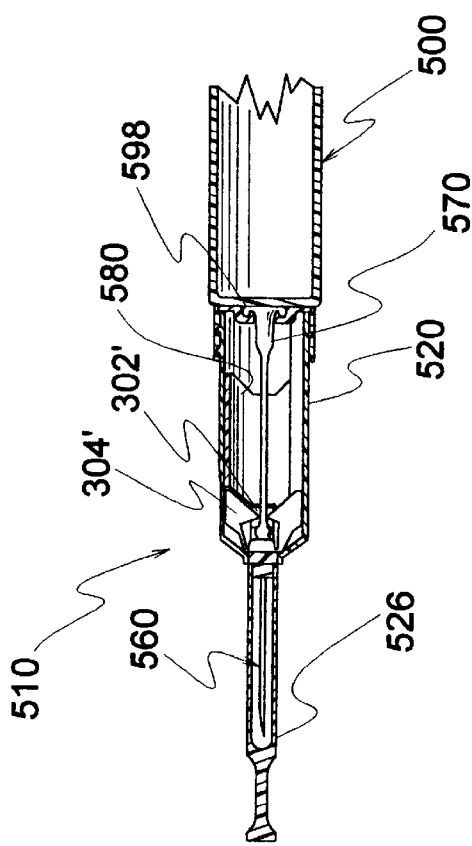
FIG. 28 is a lateral elevation section of the assembly seen in FIG. 27, but somewhat reduced in size and having a medical needle extended for use.

As seen in FIG. 27, tube member 570 comprises an internal surface 600 which conformably but relatively loosely fits over male luer fitting 512. It is preferable for fitting 512 to somewhat loosely fit surface 600 to permit space for fluid to be withdrawn inward through needle 540 when needle retraction takes place. However, it should be specially noted that surface 600 should be constricted to tightly seal about fitting 512 when needle 540 is extended outwardly from housing 520, as seen in FIG. 28. This constriction assures a tight seal between tube 570 and fitting 512 when assembly 510 is in use. Pulling of medical needle hub assembly 560 outward from housing 520, which results in the stretching of tube 570 about fitting 512 to form the seal, is best seen in FIG. 28.

On an end proximal to needle 540, tube 570 comprises an inner surface 602 which is sized to snugly fit over tube hub 594. From a simplicity of manufacturing point of view, it is preferred to provide a fit which causes tube 570 to adhere to hub 594 without adhesive. However, it is within the scope of the invention to adhesively secure tube 570 to hub 594 to assure total connection reliability. On the end of tube 570 proximal to surface 600, tube 570 comprises annular lip 604, best seen in FIGS. 30A–C.

As seen in FIGS. 30A–C, tube 570 comprises a generally frustoconical shape which is somewhat elongated into the region of inner surface 602. While a frustoconical shape is preferred, a long tubular shape of substantially constant radius may be used. However, if tube 570 is made by dipping or molding, added features which may be incorporated thereby include an O-ring shape 606, seen in FIG. 30A, disposed as an internally directed raised feature which acts to closely engage a fitting 512 and thereby to wipe fitting 512 clean when it is disengaged from tube 570. Also, a series of ribs 608, seen in FIG. 30C disposed along inner surface 600 causes a space to be eliminated when tube 570 is stretched and to be recreated when tube 570 is allowed to compress to a resting state while retracting needle 540. The added space creates a negative pressure which draws fluid inward from needle 540 as it is retracted to minimize fluid regurgitation upon needle retraction.

Lip 604 comprises an annular hook which holds tube 570 in place in groove 598 when fitting 512 is inserted into assembly 510. Preferably, lip 604 is adhesively secured to backplate 596 to permit fitting 512 to be disconnected and withdrawn without disassembling tube 570 from backplate 596.

Figure 29:
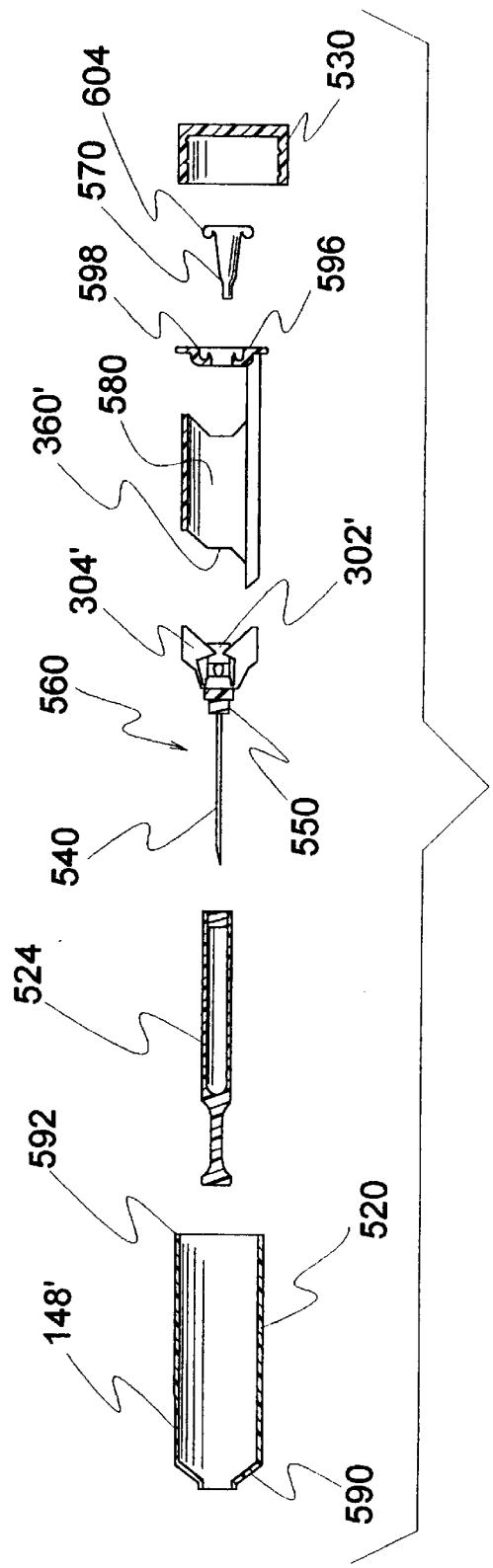
FIG. 29 is an exploded view of the retractable medical needle assembly.

As seen in FIG. 29, assembly 510 is directly adaptable to automatic construction. Housing 520, cover 524, parts 302' and 304', inner housing 580 and cap 530 are all preferably injection molded parts. Tube 570 is preferably mass produced by extrusion, dipping or molding. Needle 540 is preferably made from medical needle grade steel and sharpened to a needle point by methods currently well known in the medical needle art.

Assembly 510 is designed to be automatically assembled. First parts 302' and 304' are slidably affixed to needle 540 by inserting needle 540 through axial holes in each of parts 302' and 304'. Part 304' is best securely affixed to needle 540 by an adhesive (preferably epoxy). Cover 534 is releasibly affixed to hub 550. Tube 570 is disposed through backplate 596 and lip 604 is preferably adhesively affixed to groove 598. Inner surface 602 is disposed about hub 594 and, if necessary to assure secure affixation, bonded thereto. Housing 520 is disposed about inner housing 580 and cover 524, such that thinned section 526 is disposed outside exit and reentry end 590. One wing of part 304' is aligned with distortable area 148'. Housing 520 and blunt end 592 is juxtaposed against backplate 596 and securely affixed thereat, preferably by ultrasonic bonding. Cap 530 is releasibly affixed to backplate 596 by a threaded connection. To provide proof of tampering, cap 530 is preferably heat staked to housing 520 and housing 520 is heat staked to cover

Another Phlebotomy Embodiment

Figure 31:
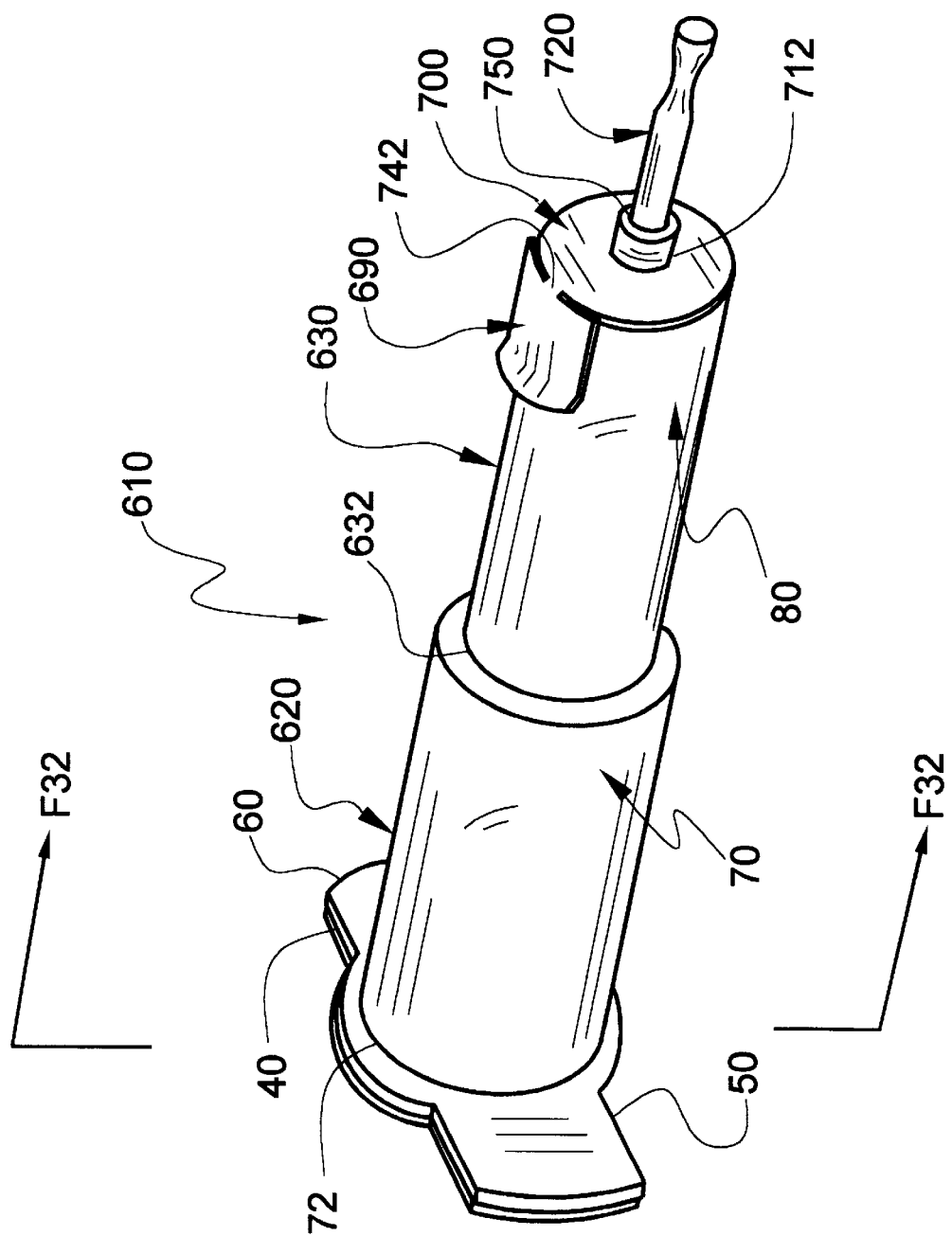
FIG. 31 is a perspective view of another blood draw device, showing the exterior of the device housing.
Figure 32:
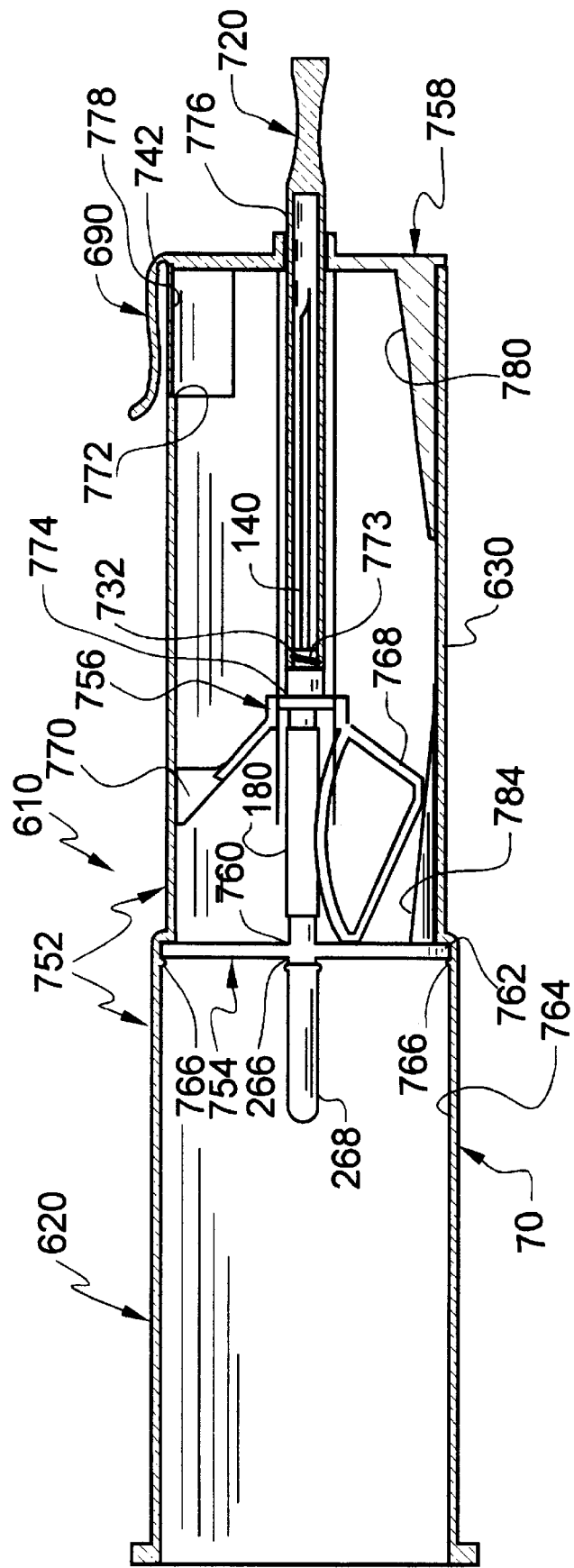
FIG. 32 is a cross section along lines F32/F32 of the blood draw device seen in FIG. 31.

Another phlebotomy embodiment of the invention is seen in FIG. 31. The embodiment of FIG. 31 comprises a device 610 which is similar in form and function to device 10 seen in FIGS. 1–4. As seen in FIG. 31, device 610 comprises a barrel section 620 and a needle containment section 630. In a completely assembled device, section 620 is securely affixed to section 630 along circular line 632 to provide protection for contents of the device from environmental damage and contamination. As seen in FIGS. 32 and 33, barrel section 620 and needle containment section 630 may be preferably molded as a single part to reduce the number of molded parts.

Barrel section 620 comprises a planar seal 40 and a pair of left and right ear or handle parts, designated 50 and 60, respectively, and a hollow barrel 70. Planar seal 40 is preferably adhesively attached to barrel section 620 within a plane area defined by continuous line 72 such that the hollow of barrel 70 is maintained in a sterile condition prior to use. To use device 610, seal 40 is manually removed. Of course, a different kind of seal may be used, such as a snap-on part which may be molded as a tether-attached part of section 620. The snap-on part is not shown in FIG. 31, but production of such parts is well known in the art. A more detailed description of the internal parts of barrel 70 is provided hereafter.

Needle containment section 630 comprises an elongated tube 680, a flap 690, a proximally facing front face plate 700 and a needle cover 720 partly externally disposed prior to use. Needle cover 720 is separable from front face plate 700 by means of a frangibly detachable cylindrical segment 712 of needle containment section 630, which is described in more detail hereafter.

Steps related to the use of device 610 are similar to those disclosed for device 10 in FIGS. 2–4. However, needle cover 720 is preferably attached to cylindrical segment 712 by heat staking or ultrasonic welding. Therefore, needle cover 720 is detached by breaking the heat stake or ultrasonic weld joint and pulling needle cover 720 and its associated medical needle, generally numbered 140, outward from needle containment section 630. Once needle cover 720 and medical needle 140 are fully extended, a latch is caught upon a catch retaining needle cover 720 and medical needle 140 in position just prior to use. Structure of examples of a catch, a latch and workings of other parts disposed within needle containment section 630 are disclosed in more detail later.

As in device 10, seal 40 is removed from barrel section 620. In a next step, needle cover 720 is removed from device 610. Needle cover 720 is preferably attached to a hub 732 by a rotatably detachable coupler, such as by a threaded, frictionally held or bayonet type connector. In any event, the coupling attachment between hub 732 and cover 720 must be able to support a pull force at least as great as a retarding force imposed in the opposite direction by a retracting mechanism which is energized by the pull extending cover 720 until engagement of the aforementioned catch and latch. As seen in FIG. 33, hollow medical needle 140 is bared upon removal of cover 720.

Similar to flap 90, flap 690 comprises a living hinge attachment 742 to needle containment section 630. Different from flap 90, flap 690 does not comprise a hook latch normally engaged in a groove, but is preferably molded to lie in a biased position upon tube 80. However, flap 690, like flap 90, is facilely lifted from its biased position to permit access to a distortable section disposed under and protected by flap 690. Thus, during a medical blood draw procedure, flap 690 is protectively disposed. Once blood acquisition has been completed, flap 690 is lifted by action of a single digit after which needle 140 may be retracted by depressing an area 778 which is made and positioned to act in the same fashion as area 148. Retraction places needle 140 safely inside tube 80. The only access inside tube 80 and needle 140 is a hole 750 through which needle cover 720 was drawn to expose needle 140. Retraction mechanisms for device 610 are generally the same as those disclosed for device 10. However, there are differences in internal mechanisms of the two devices which are described in detail hereafter. It may be preferable to protect area 748 by a raised ridge or rim (not shown) rather than by flap 690 to minimize required user training. In such a case, the raised rim should provide tactile feedback to prevent inadvertent depression of area 778.

Attention is now drawn to FIG. 32 wherein device 610 is seen to comprise a reduced number of parts compared to the number of parts shown for the device seen in FIGS. 16–21. Device 610 comprises a cylindrical part 752 which is molded as a single part and comprises the cylindrical portions of needle containment section 630 and barrel section 620. Further, device 610 comprises a rear assembly plate 754, which is similar in form and function to assembly plate 264, except that there is no part which is equivalent to key 260 on plate 754. Device 610 also comprises a single hub 756, elastic tube 180 and a front plate 758.

Similar to assembly plate 264, assembly plate 754 comprises a snubber 268 and rear needle 266 for piercing a vacuum blood collection tube. Proximal to elastic tube 180, assembly plate 754 comprises a hub connection 760 for connecting plate 754 to tube 180. Circumferentially, plate 754 comprises an outside edge 762, which is sized to compressibly fit inside the inner wall 764 of barrel part 620. Preferably, inner wall 764 also comprises a plurality of raised beads or a raised inner ring 766 into which outside edge 762 is "snapped" for firm retention. However, outside edge 762 may be held in place by adhesive bonding or ultrasonic welding, all of which are well known in the art of joining one plastic part to another.

Hub 756 is used to interconnect a medical needle 140 to tube 180 and to provide a tube distorting part 768 and a wing latch 770, which is disposed to attach to a catch 772 when needle 140 is extended for use. Further, hub 756 comprises a threaded portion 773 which is proximal to the sharp end of the needle and used to firmly but releasibly connect to needle cover 720. As earlier disclosed, a friction fit or bayonet coupler or other equivalent connector may be used within the scope of the invention in place of portion 773. Disposed distal from hub 732 is a cylindrical shoulder 774, which fills a cylindrical orifice 776 in front plate 758 through which needle cap 720 and needle 140 are pulled for use of needle 140. Shoulder 774 should be sized to fit snugly into orifice 776 to provide axial support for needle 140. Hub 756 may or may not employ a tube distorting part, such as part 768, within the scope of the invention.

In this manner, the orifice through which needle 140 is retracted to safe containment within tube 80 is orifice 776. For this reason, orifice 776 should be made sufficiently small so that no access is provided to human limbs or other parts. Note that device 610 contains only five parts which are preferably made by injection molding. Note also that, by making section 630 of the same internal diameter as required of orifice 776 for digital safety, device 610 can be made without front plate 758, reducing the number of injection molded parts to four. They are needle cap 720, cylindrical part 752, plate 754, hub 756 and front plate 758. The single hub 756 provides the opportunity for this limited number of parts. It may at first appear that fewer parts may be used in construction of device 610 by combining one or more of the five parts. However, based upon current molding and assembly considerations related to cost of the device, this parts breakdown is currently preferred for this embodiment.

Attention is now turned to hub 756. Similar to parts 302 and 302', hub 756 comprises wing latch 770, which is designed to catch at catch 772. As previously described for earlier embodiments, cylindrical part 752 comprises distortable section 778, distortion of which releases latch 770 from catch 772 to permit elastic contraction of tube 180 to retract needle 140 into needle containment section 630.

Figure 33B:
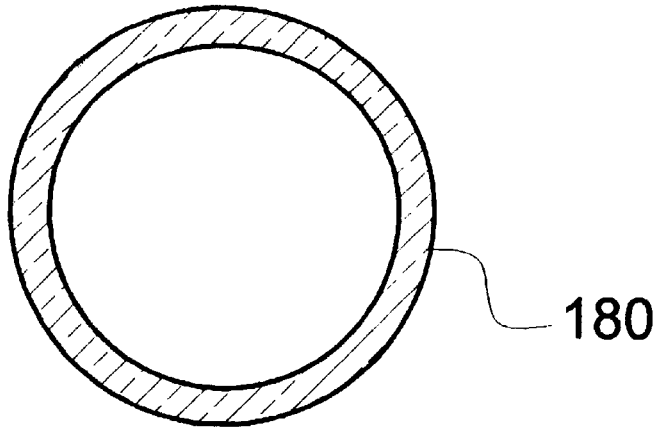
FIG. 33B is a cross section of a stretched elastic tube.
Figure 33C:
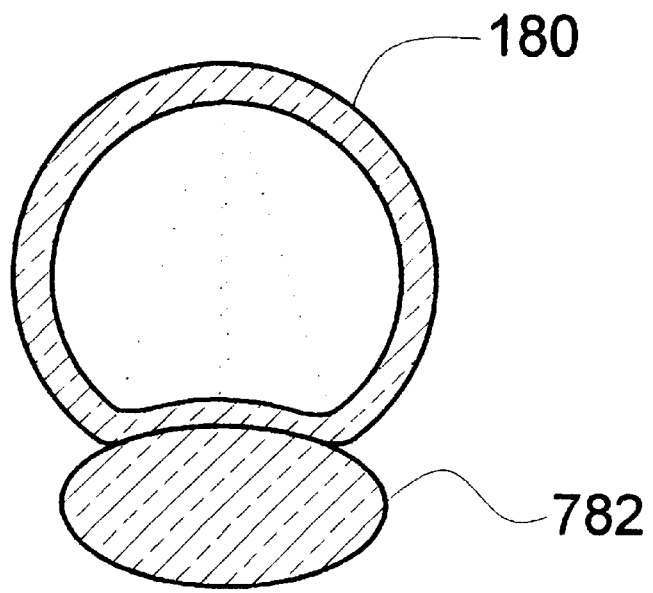
FIG. 33C is a cross section of the stretched elastic tube seen in FIG. 33B, but being distorted by a plastic section from the more circular geometry seen in FIG. 33B.

Hub 756 also comprises tube distorting part 768 which is key to providing control of regurgitant fluid without requiring a check valve. Note that when hub 756 is pulled forward in needle containment section 630, a sloped ramp part 780, preferably molded as part of front plate 758, causes a raised segment 782 of tube distorting part 768 to engage and distort a section of tube 180. Reference is made to FIG. 33B wherein a non-distorted tube is seen to have a substantially circular cross-section. However, in a region or section of tube 180 which is so distorted by part 768 (segment 782), as seen in FIG. 33C, the circular cross section is flattened on one side to reduce the internal cross-sectional area of tube 180. This flattening produces a reduced volume of tube 180 in the section so affected.

To understand the need for such a reduction when needle 140 is extended and device 610 is cocked for needle retraction, one must understand the general dynamics of changes in internal tube volume as a tube is stretched between two hubs to which the tube is attached. Generally, if fluid is captured as a contiguous fluid bolus between, but not in contact with, connecting hubs, and a mark is placed at each end of the bolus, as the tube is stretched, the ends of the fluid bolus remain substantially at the marks. However, if fluid inside the tube is increased to reside within connecting hubs as well, the volume for containment of fluid inside the tube between the hubs increases primarily due to connecting end effects at the hubs.

Such an increase in volume inside tube 180 in a stretched condition relative to the volume inside tube 180 in a relaxed condition causes an excess of contained fluid which is regurgitated or pumped from tube 180, usually through needle 140, when needle 140 is retracted as tube 180 is permitted to contract It has been found through experimental study that the hub size is an important factor in controlling the amount of volume increase. However, complete control cannot be achieved by the hub design alone. Therefore, a distortion of tube 180, when in a stretched condition, provides a significant method for reducing the internal volume of stretched tube 180 to be less than the relaxed volume of tube 180.

Fluid dynamics associated with braking a rapidly retracting needle (and tube) also may contribute to fluid regurgitation. For this reason, it is recommended that final retracting velocity be maintained within as low a velocity as possible. It is for this purpose that a posteriorly disposed ramp 784 provides a frictional contact between tube 180 and part 768 at the end of needle retraction travel. In this embodiment, it is preferred that ramp 784 be molded as a part of plate 754. While this method of fluid control is seen to be applied to the embodiment seen in FIGS. 31–33C, one who is skilled in the art of retracting systems and fluid control would understand that this method or other methods disclosed hereafter may be applied to other needle retracting embodiments disclosed herein.

Use of device 610 is similar in functional steps to devices heretofore described. Needle 140 and needle cap 720 are extended from the rest of device 610 as seen in FIG. 33, with needle cap removed as portrayed in FIG. 33A. The needle is used in a medical procedure after which protecting flap (shroud) 690 is raised, preferably by a finger or thumb, to provide access to distortable section 778. Section 778 is distorted to cause latch 770 to become disengaged from catch 772. The freed hub 756, needle 140, and contracting tube 180 are then fully retracted into needle containment section 630 for safe retraction and storage of needle 140.

Figure 34:
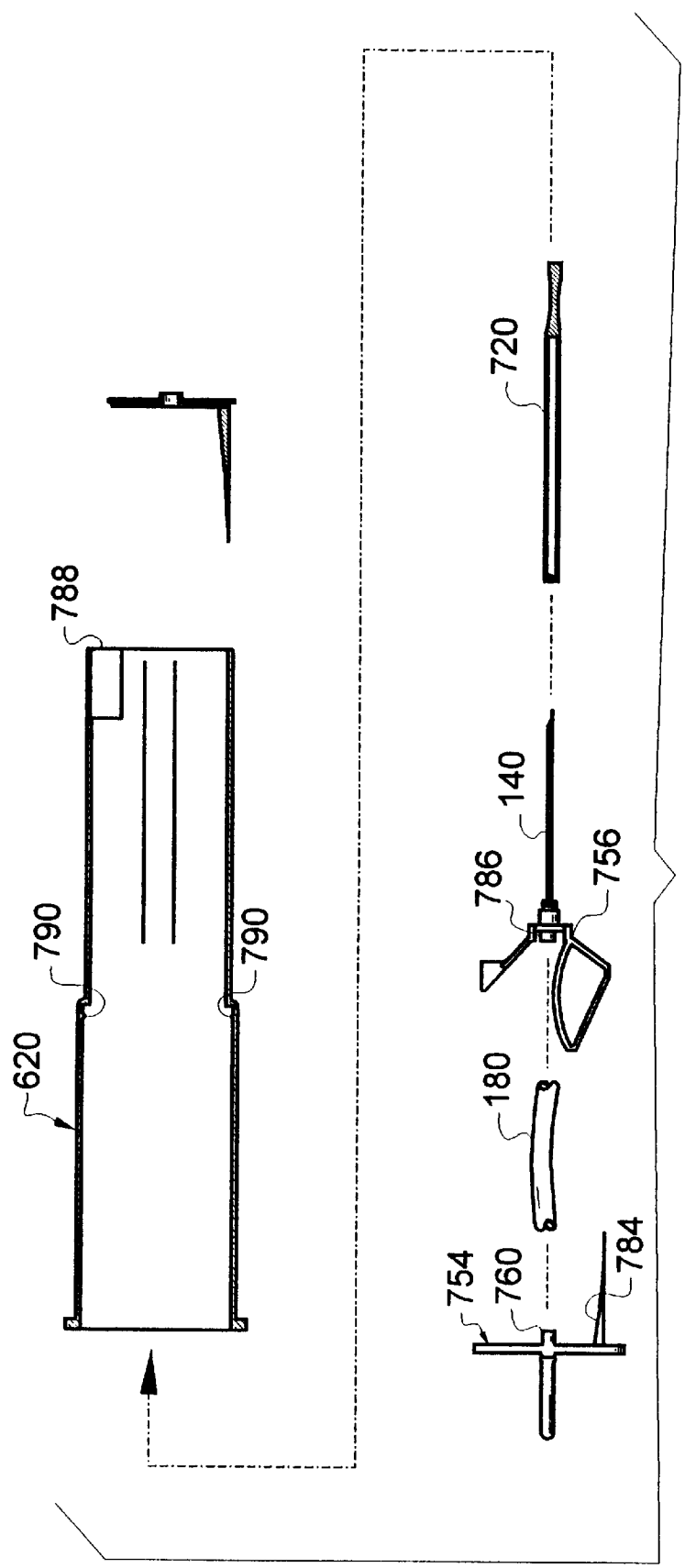
FIG. 34 is an exploded view of parts seen in FIGS. 32 and 33.

Of course, for device 610 to compete with current needle devices, assembly should be simple to automate. The simple, linear assembly procedure for device 610 is shown schematically in FIG. 34. Needle 140 is securely affixed to hub 756 (preferably by epoxy), and cover 720 is securely, but releasibly affixed to hub 756 to protect needle 140. Tube 180 is affixed to tube attachment connecting hubs 760 and 786. Methods for securely attaching tube 180 are well known in the current state-of-the-art of connecting elastic tubes to plastic hubs and range from use of connection by physical hub design alone to the use of adhesives and solvents. Once a tube 180 material and a hub 756 and back plate has been selected, the type of appropriate connecting method can be determined by current standard materials and procedures.

So attached, needle 140 and other joined parts are introduced into barrel part 620 until the needle cover 720 is exposed at proximal end 788. To complete assembly of device 610, orifice 776 of front plate 758 is fitted over needle cover 720 and firmly affixed to part 620, preferably by heat staking, although other connecting techniques such as mechanical interconnects and adhesive bonding may be used. Also, it is preferred to either mechanically affix back plate 754 in place (such as by an internally disposed containment ring 790 as seen in barrel part 620) or by heat staking or ultrasonic welding.

Another Catheter Embodiment

Figure 35:
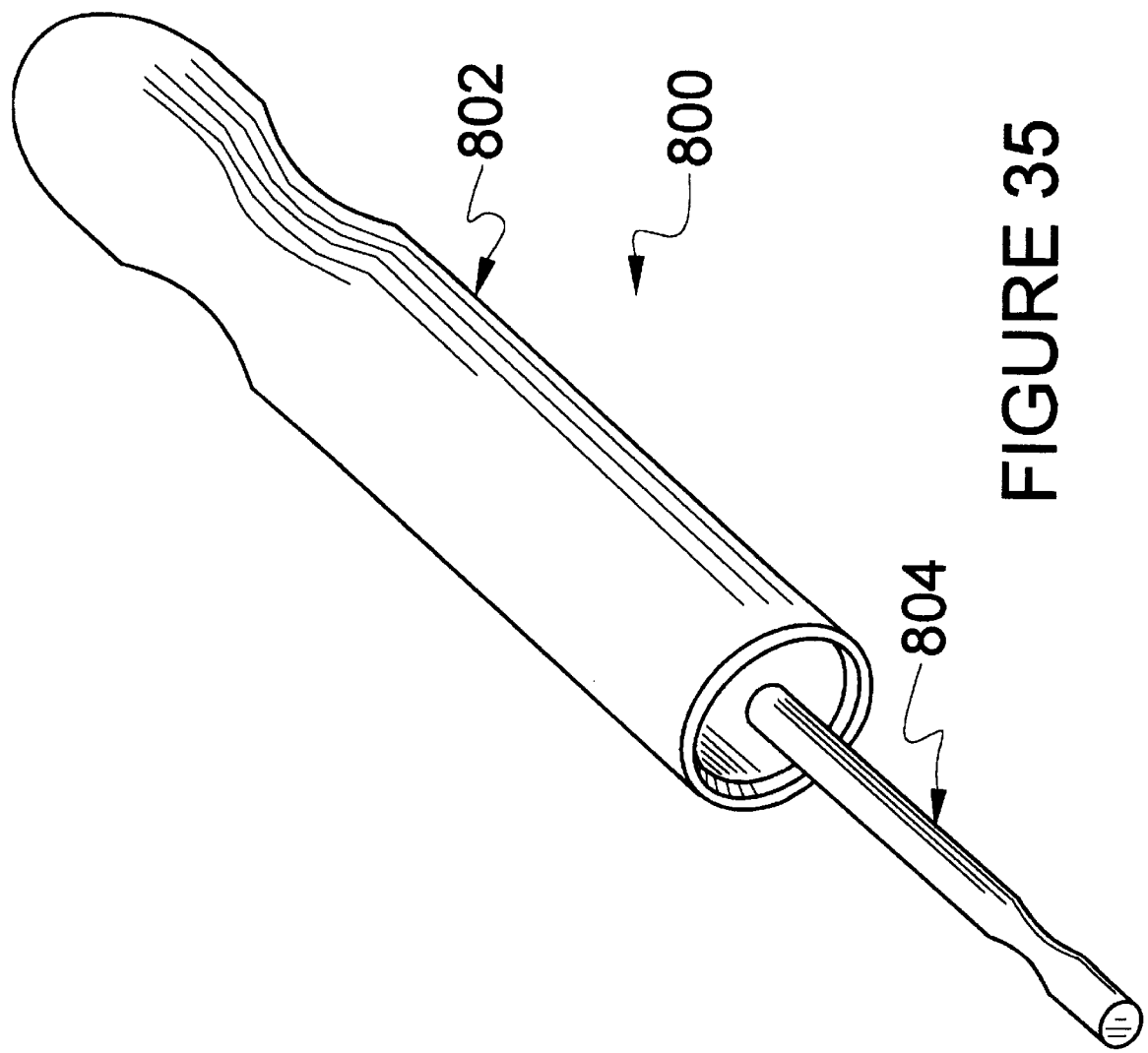
FIG. 35 is a perspective view of a needle withdrawal device which is cocked by extending a slidable exterior cover away from a needle cover.
Figure 36:
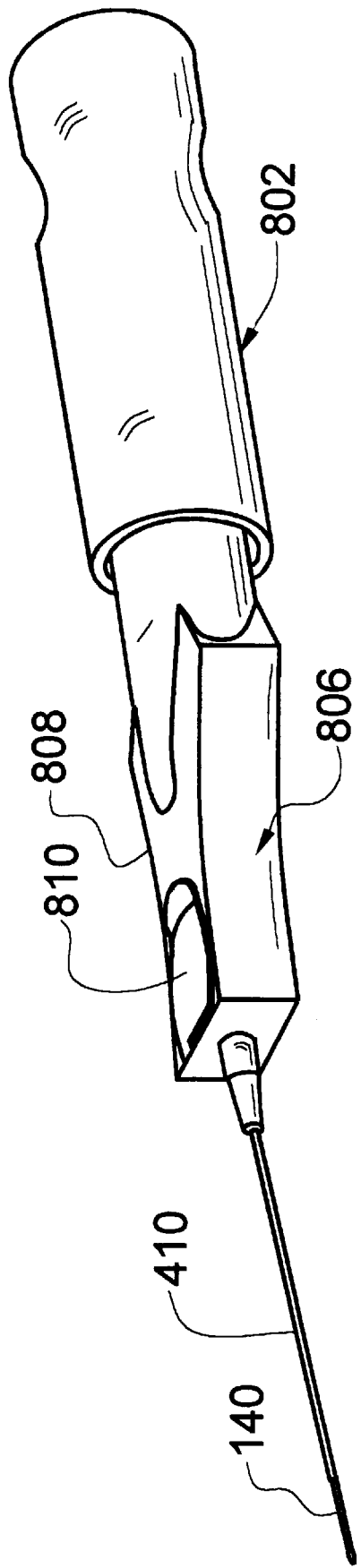
FIG. 36 is a perspective view of a catheter version of the needle withdrawal device seen in FIG. 35, with the slidable exterior cover disposed away from a medical needle to thereby cock the device for automatic needle retraction.
Figure 37:
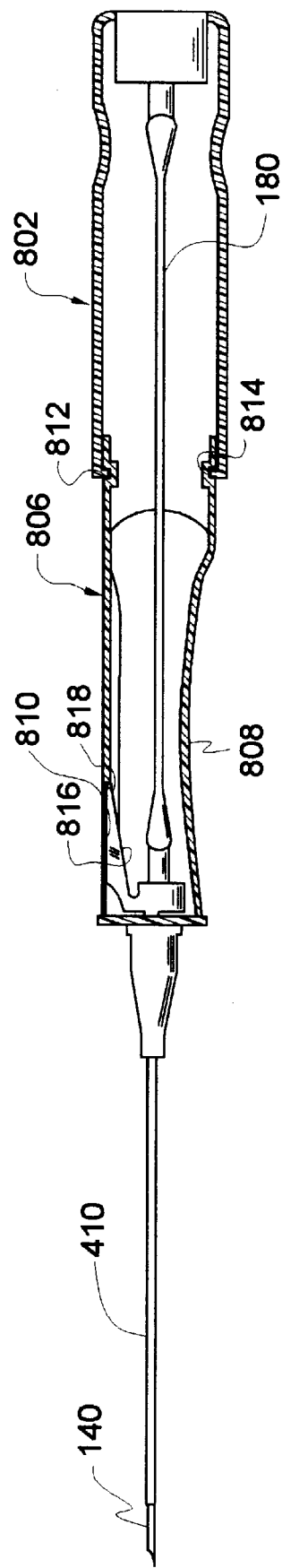
FIG. 37 is a cross section of the catheter version seen in FIG. 36.

Another catheter embodiment of the invention which employs a permanent catch and a separate latch release mechanism is seen in FIGS. 35–37. This construction is best applied to needle retraction devices more closely related to catheter and syringe embodiments due to assembly constraints of embodiments having large posterior parts, such as the barrel part of a blood draw device.

The embodiment of FIGS. 35–37 is a device 800 which comprises a rearwardly extendable cover section 802 and a forwardly extendable needle cover 804. As seen in FIG. 36, cover section 802 is extended rearwardly relative to needle 140' (as an example, a catheter needle and catheter configuration) to permit needle 140' to be exposed for use.

As seen in FIG. 36, in addition to cover section 802 and needle cover 804, device 800 comprises a preformed insertion handle section 806 and a catheter 410. Section 806 comprises a thinned section 808, which provides facile gripping for catheter insertion, and a distortable section 810 by which a latch and catch release is made to retract needle 140'.

In the cross section shown in FIG. 37, section 806 is seen to comprise an annular catch 812 to permanently anchor a corresponding annular latch 814 of cover section 802. In this embodiment, a hub latch 816 is secured against catch 818 when manufactured. Tube 180 is stretched to provide retractive force by rearward extension of section 802. To retract needle 140' to safe containment inside the combined internal volumes of sections 802 and 806, distortable section 810 is compressed to release latch 816 from catch 818.

Fluid Control for Phlebotomy and other Applications

Reference is now made to FIGS. 38–42, wherein another apparatus and method for constraining internal volume of a stretched tube 180 relative to a relaxed tube 180 is seen. In this embodiment a device 820 is seen in cross section. In most ways device 820 is similar in form and function to device 610. Major differences comprise elimination of ramps 780 and 784 in device 820. In the place of ramp 780, a tapered cylindrical section 822 is used in place of section 630 to perform the ramping function of ramp 780. The other major difference is the form and function of a forward hub 824. Note that hub 824 is the only hub surrounding needle 140.

Hub 824 comprises a segment 826 to which a needle cover 720', like needle cover 720, is attached for the purpose of protecting needle 140 and pulling needle 140 and hub 824 to extend needle 140 for use in a medical procedure. Similar to section 630, device 820 comprises a catch 828 and an associated latch 830 which engage to retain hub 824 and needle 140 in an extended state. Release of latch 830 from catch 828 is preferably caused by distortion of a distortable portion 832 of tapered cylindrical section 822.

Distal to segment 826, hub 824 comprises a pair of wing parts 834 and 836 which form a clamp about tube 180 when hub 824 is moved forward to extend needle 140 for use. As seen in FIGS. 41 and 42, each wing part 834 and 836 comprise a U-shaped clamping surface 838 and 840, respectively. When tube 140 is in a relaxed position, the clamping surfaces 838 and 840 do not distort the otherwise circular cross-section of interposed tube 180. However, when tube 180 is stretched by extension of needle 140, the taper of cylindrical section 822 causes wing parts 834 and 836 to clamp about tube 180. The distortion reduces the cross section and therefore the internal volume of stretched tube 180, thereby causing tube 180 to have a smaller internal volume when stretched than when relaxed. Such a condition substantially eliminates any opportunity for fluid regurgitation when needle 140 is retracted. Other apparatus and methods may be used within the scope of the invention to reduce the volume of a stretched tube 180 to be less than a relaxed tube 180. An example of another method is disclosed hereafter.

The opening between clamping surfaces 838 and 840, when needle 140 is extended, determines the amount of flattening of tube 180 and, thus, the amount of volumetric reduction therefrom. An exemplary calculation showing the amount of volumetric reduction achievable is provided as follows:

If D is the internal diameter of an unstretched tube, and d is the internal diameter of a tube stretched to three times its normal length, then it is well known in the art that $D^2$ is approximately equal to three times $d^2$. If, in a stretched and flattened tube, the internal height of the tube may be represented by h, as seen in FIG. 42. Note that the circumference (C) of the stretched tube is π times d. The area of the stretched tube is π times $d^2/4$. However, the cross sectional area (A) of a flattened portion of the stretched tube is given by:

$$A = \pi h^2/4 + (C - \pi h)h/2 \qquad \text{Eq. 1}$$

For a case where h=0.46 mm and d is 0.92 mm, A equals 0.50 mm². The cross-sectional area of a stretched, but unflattened tube is 0.66 mm², providing a reduction in area of 0.16 mm² or a volume reduction of about 0.16 mm³ for each mm the tube is clamped. If the tube is clamped ¾ inch or 19 mm, the exemplary reduction is about 3.0 mm³.

Figure 38:
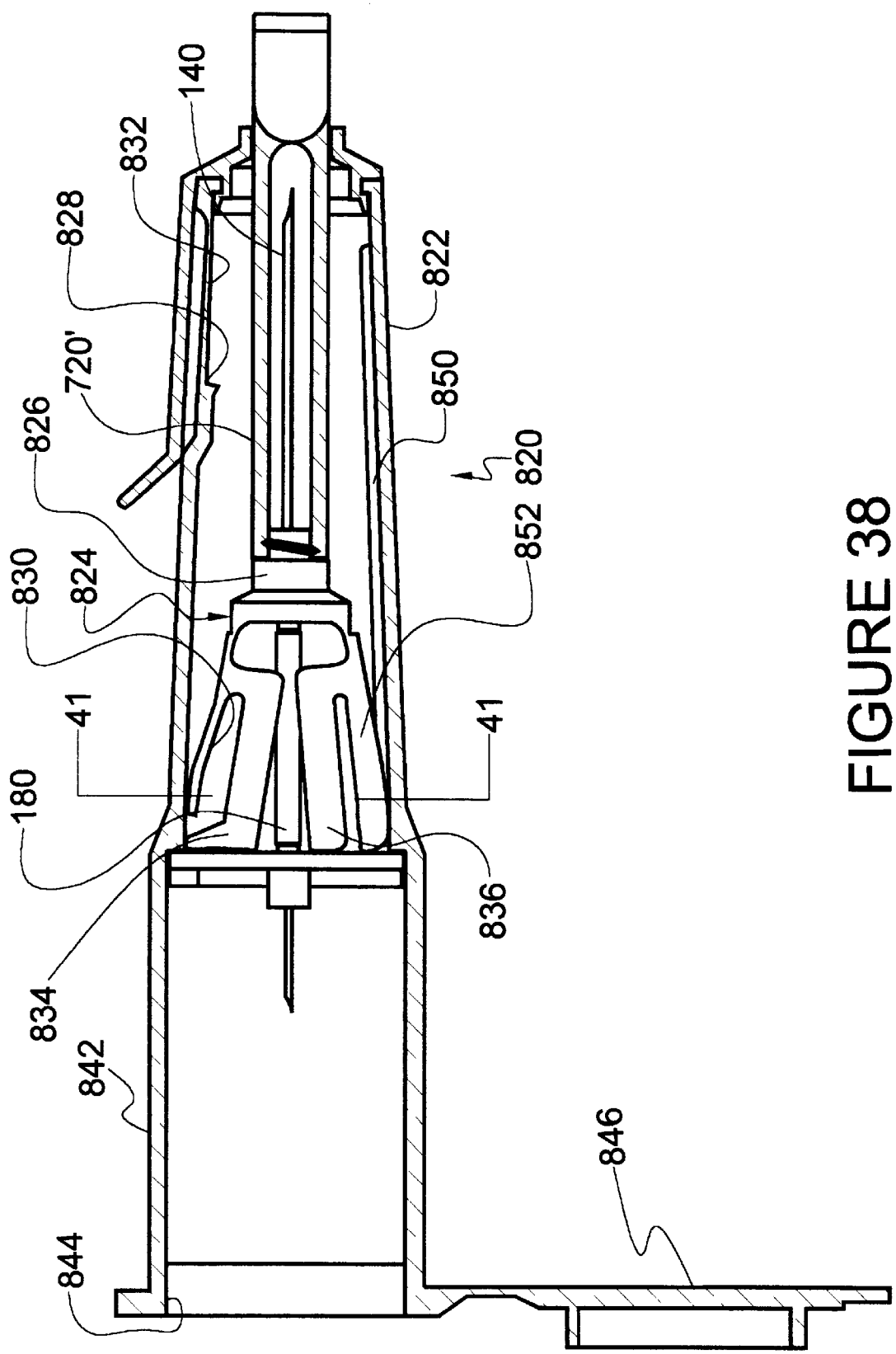
FIG. 38 is a cross section of a needle withdrawal device disposed in a rest or needle transportation state and having another embodiment of an elastic tube distortion apparatus.
Figures 39, 40:
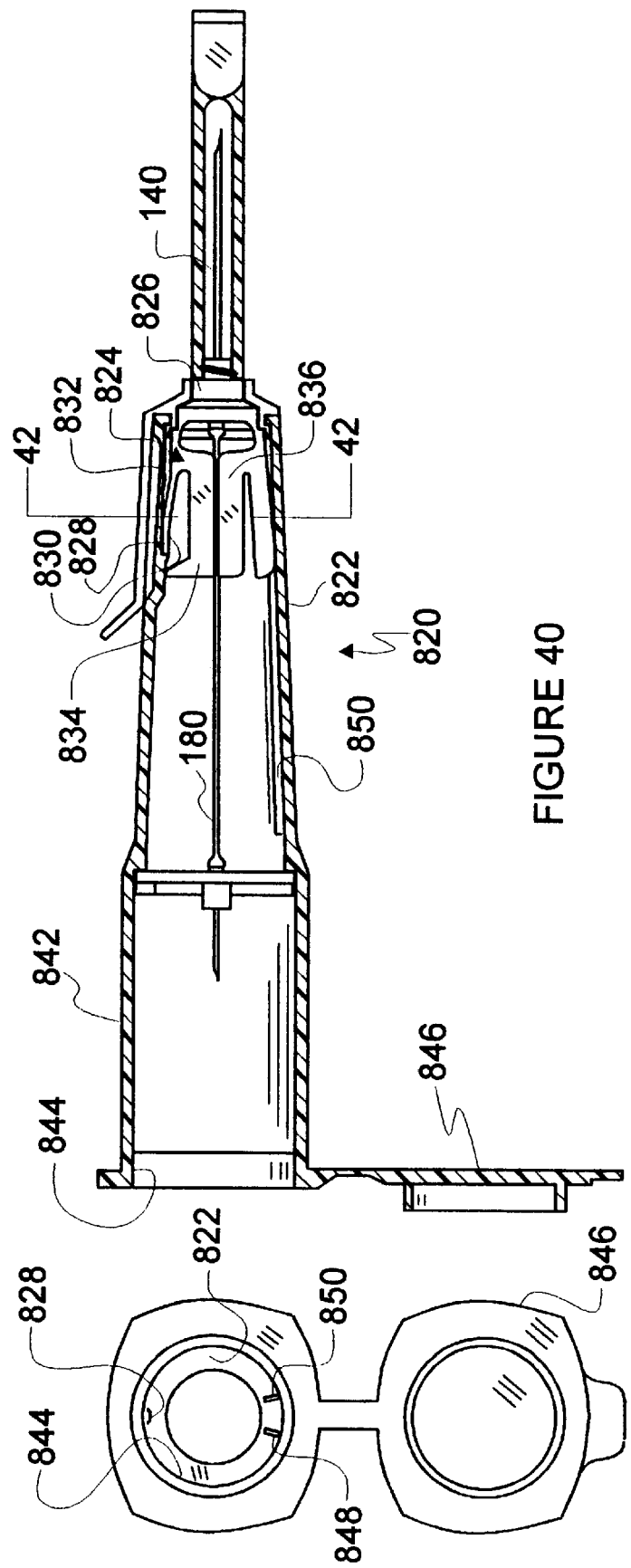
FIG. 39 is a rear elevation of the needle withdrawal device seen in FIG. 38.
FIG. 40 is a cross section of the needle withdrawal device seen in FIG. 38, but disposed in a cocked or ready state whereat a medical needle is ready for use.

Since it is important that latch 830 aligns with catch 828 when needle 140 is extended, tapered cylindrical section 822 preferably comprises guides to assure correct travel of hub 824. Distally, device 820 is seen in FIGS. 38 and 40 to comprise a barrel section 842. At its back end, section 842 is seen to comprise an opening 844 and a tethered cover 846, which is used to provide protection for a rear needle 266 described earlier. Cover 846 is similar in form and function to cover 151 described earlier. As best seen in FIG. 39, segment 822 comprises a pair of guide rails 848 and 850. An inferior segment 852 of wing 836 is disposed to ride between rails 848 and 850 to maintain latch 830 in a desired position relative to catch 828 and distortable portion 832.

Figure 43:
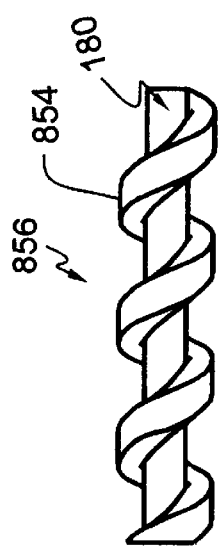
FIG. 43 is a perspective view of an elastic tube with a helical member wrapped about the tube.
Figure 44:
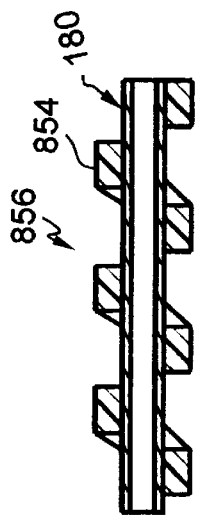
FIG. 44 is a cross section of the elastic tube and helical member seen in FIG. 43.
Figure 45:
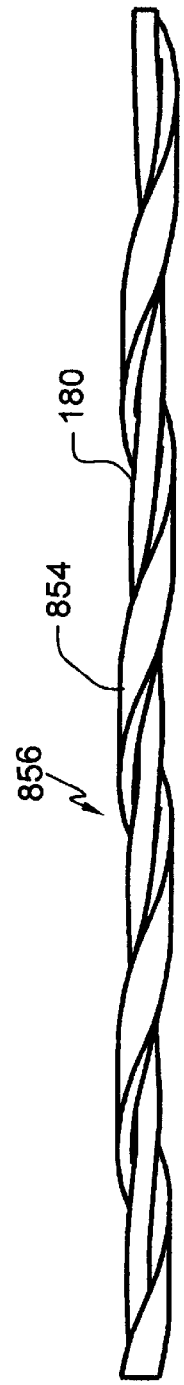
FIG. 45 is a perspective view of the elastic tube of FIG. 43 stretched and the helical member also elongated to close tightly about the elastic tube to distort the tube from a round geometry.
Figure 46:
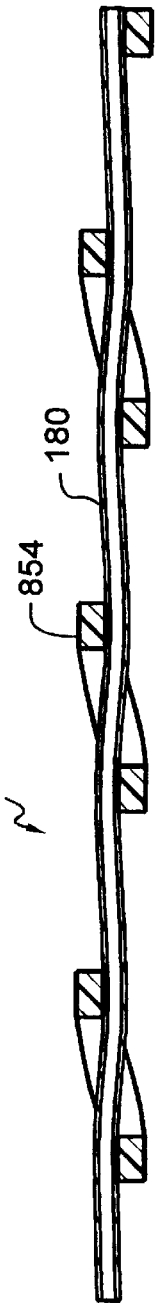
FIG. 46 is a cross section of the elastic tube and helical member seen in FIG. 45.

Another embodiment which constricts the volume of a constricted tube 180 to be less than the volume of tube 180 in a relaxed state is seen in FIGS. 43–46. FIGS. 43 and 44 show tube 180 in a relaxed state. FIGS. 45 and 46 show the tube 180 in a stretched state. In simplest terms, tube 180 is seen to be disposed within a helical wrap 854 to form a combination 856. As is well known in the art, if wrap 854 is relatively inelastic, extending wrap 854 to nearly its resting length will cause wrap 854 to approximate a nearly straight line. As the cross sectional area of an elastic tube decreases by approximately the power of the number of rest lengths the tube is stretched, one who is skilled in the art of helix formation and elastic tube dynamics understands that there exists a critical pitch of the helix beyond which the internal volume of the helix decreases more rapidly upon extension than the internal volume of an interposed tube, such as tube 180.

Calculation of the critical pitch is relatively straight forward, as the following example shows. The general Cartesian coordinate equations for a helix are:

$$x = a \cos \theta = a \cos ns \qquad \text{Eq. 2}$$

$$y = a \sin \theta = a \sin ns \qquad \text{Eq. 3}$$

$$z = 1 \qquad \text{Eq. 4}$$

where:

a is the radius of the helix.

θ is the angle of rotation of the helix about its long axis.

s is the distance along the helix.

l is the distance along the long (z) axis of the helix.

n is the angular rate of change of θ as a function of l.

An equation for the length of a segment along the helix is given by:

$$ds = sqrt(dx^2 + dy^2 + dz^2 +) \qquad \text{Eq. 5}$$

Differentiating Eq.'s 2, 3 and 4, with respect to s and l, and substituting into Eq. 5:

$$ds = sqrt(a^2 n^2 \sin^2 ns \, ds^2 + a^2 n^2 \cos^2 ns \, ds^2 + dl^2) \qquad \text{Eq. 6}$$

Which reduces to:

$$ds = sqrt(a^2 n^2 ds^2 + dl^2) \qquad \text{Eq. 7}$$

or:

$$ds^2(1 - a^2) = dl^2$$

Integrating over the length (S) of the helix and of a distance (L) to which the helix is spread, the relationship between a and n is given by:

$$S = L / sqrt(1 - a^2 n^2) \qquad \text{Eq. 8}$$

The value of n may be given as:

$$n = 2\pi N/S \qquad \text{Eq. 9}$$

Where N is the total number of turns in helix length S. Substituting for n and squaring both sides of the equation and solving for radius a:

$$S = L / sqrt(1 - a^2 [2\pi N/S]^2) \qquad \text{Eq. 10}$$

or:

$$S^2 = S^2 L^2 / (S^2 - a^2 [2\pi N]^2) \qquad \text{Eq. 11}$$

which yields:

$$L^2 = (S^2 - a^2 [2\pi N]^2) \qquad \text{Eq. 12}$$

Solving for a:

$$a = Sqrt(S^2 - L^2)/2\pi N \qquad \text{Eq. 13}$$

Solving r N:

$$N = Sqrt(S^2 - L^2)/2\pi a \qquad \text{Eq. 14}$$

Through experimentation, it has been found that change in internal volume of a stretched tube between two know points along a length of the tube (not comprising endpoints where the tube is connected to a hub or the like) is not changed substantially by stretching.

Therefore, the following relationships apply:

$$V = 2\pi a^2 l' \qquad \text{Eq. 15}$$

where:

l' is also the length of the section between the two known points.

Note that, since V is a constant:

a is substantially equivalent to sqrt(K/l')

where K is an easily derived constant.

It has also been determined experimentally that the total internal volume (V') of an elastic tube does vary due at least to volumetric variations at tube ends where unions are made with connecting hubs. This variation generally causes the volume of a stretched tube to be greater than the volume of the same unstretched tube. This change in volume results in fluid regurgitation when the tube is used as a retracting mechanism and concurrently as a container and transport path for fluid received from a medical needle. It is for this reason that use of a helix wrap (such as wrap 854) is preferably used to reduce or restrict an increase in volume of the stretched tube.

An example of a method of design and employment of a volume restricting helix is given below:

Using a plastic tube in place of the medical needle to permit visual observation of the increase in volume due to stretching an elastic tube to a length three times its rest state length, the increase ($\delta V'$) in volume was observed to be:

$$\delta V' = 6.5 \text{ microliters } (\mu l)$$

in an elastic tube having the following rest state dimensions:

O.D.$_{at\ rest}$=3.18 mm
I.D.$_{at\ rest}$=1.59 mm
Length$_{at\ rest}$=19.1 mm
Internal Volume$_{at\ rest}$=38 $\mu l$ and having the following stretched dimensions:

Nominal O.D.$_{stretched}$=1.83 mm
Calculated I.D.$_{stretched}$=0.92 mm
Length$_{stretched}$=57.2 mm
Internal Volume$_{stretched}$=45 $\mu l$
Nominal tube O.D. volume$_{stretched}$=150 $\mu l$ Assuming that a compressive reduction in total tube volume (including the tube itself) would result in a reduction in internal volume of substantially the same amount, a reduction of the O.D. volume to approximately 143 $\mu l$ when the tube is stretched requires compressing the exterior of the tube to an equivalent average diameter of about 1.78 mm.

Because the number of turns of the helix is not permitted to change when the helix is lengthened from a rest state to a stretched state of tube 180 in this application, Eq. 14 (reproduced below) can be used to evaluate the length S and number of turns N of the helix.

$$N = Sqrt(S^2 - L^2)/2\pi a \qquad \text{Eq. 14}$$

By entering values for the rest or unstretched state (r), Eq. 14 becomes:

$$N = Sqrt(S^2 - L_r^2)/2\pi a_r \qquad \text{Eq. 14r}$$

Likewise, entering values for stretched state (s), Eq. 14 becomes:

$$N = Sqrt(S^2 - L_s^2)/2\pi a_s \qquad \text{Eq. 14s}$$

and:

$$Sqrt(S^2 - L_r^2)/2\pi a_r = Sqrt(S^2 - L_s^2)/2\pi a_s$$

squaring and cross multiplying:

$$(S^2 - L_r^2)(2\pi a_s)^2 = (S^2 - L_s^2)(2\pi a_r)^2$$

solving for S:

$$S^2 = (L_r^2 a_s^2 - L_s^2 a_r^2)/(a_s^2 - a_r^2)$$

For the example given above:

S=68 mm

Evaluating N (number of turns) from equation 14s:

N=6.6 turns

However, as seen in FIGS. 45 and 46, wrap 854 does not fully enclose tube 180 and, S therefore, tube 180 is periodically free to expand outward from the constraint of wrap 854 in the gaps between the constraint of the helix. For this reason, the number of actual turns ($N_a$) should be fewer than the predicted value of N, above. Even so, a more desirable value of $N_a$ can be arrived at without undue experimentation by one skilled in the art of fluid dynamics. It is well known in the elastic tube extrusion art to enclose one or more helically wound coils of support material in the wall of extruded tubes. Such enclosed coils are most often used to add strength to the tube to support the tube against inadvertent collapse or to be able to withstand high pressure. A process similar to such an extrusion process can be used to make combination 856 by properly controlling the pitch and using the coil not to support the tube against collapse, but to constrict the tube when it is stretched with a predetermined pitch of the helix.

Interlocking Hub Embodiment

Figure 47:
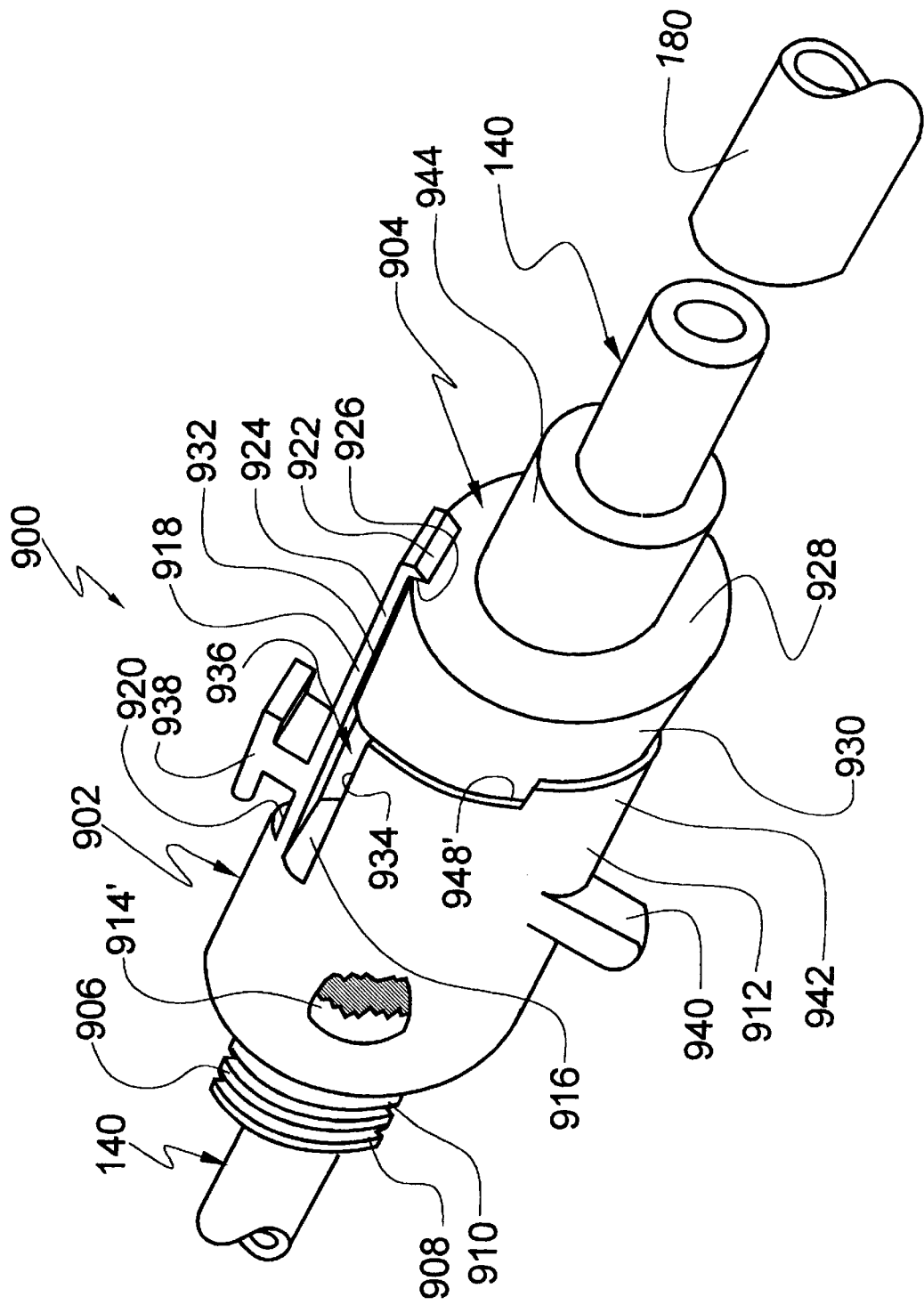
FIG. 47 is a perspective view of a two part medical needle hub apparatus.

Reference is now made to FIGS. 47 and 48 wherein another hub part 900 is seen. Except for the apparatus and method related to latching part 900 and releasing a portion of part 900 to retract a needle 140, part 900 is similar in form and function to needle/hub part 160.

Part 900 comprises two separable components, a forward component 902 and a rear component 904. Forward component 902 comprises a section 906 which comprises a threaded segment 908 and a cylindrical segment 910 which are similar in form and function to threaded portion 776 and cylindrical shoulder 774, respectively. Joined to segment 910 is an elongated cylindrical body 912 which comprises a pair of wing latches 914 and 914'. n FIG. 47, only a portion of one wing latch, latch 914', is seen mostly removed for a better presentation of the rest of forward component 902. A portion of cylindrical segment 910 is removed to provide an "L" shaped surface 916, the purpose of which is described in detail hereafter. Further, component 902 comprises an elongated strut 918 securely affixed on one end 920 to surface 916, as seen in FIG. 47.

Strut 918 comprises a latching member 922 disposed at the other end 924. Latching member 922 comprises a latch 926, which firmly, but releasibly, affixes forward component 902 to rear component 904 along a surface 928 of component 904. Surface 928 is preferably orthogonal to the axis of needle 140.

Component 904 comprises a main body section 930 which comprises a flattened portion 932, juxtaposed to an overlaying part of strut 918, as seen in FIG. 47. Portion 932 is raised above a portion 934 of "L" shaped surface 916 which is parallel to portion 932. In combination, strut 918, portion 934 and flattened portion 932 define a substantially rectangular opening 936 into which strut 918 may bend to release latching member 922 from surface 928.

Though not shown, it should be understood that part 900 is used within an elongated cylinder in a manner similar to that of needle/hub part 160. In that manner, forward component 902 comprises a raised button 938 which is raised from strut 918 to communicate with an internal surface of a distortable membrane, such as membrane 778 seen in FIG. 32. With distortion of the membrane and compressibly communication with button 938, strut 918 above opening 936 can cause strut 918 to bend toward the surface of portion 934 such that latching member 922 is released from surface 928.

Forward component 902 further comprises a stabilizing leg 940, which is designed to communicate with an inner surface of the aforementioned elongated cylinder which is juxtaposed to the distortable membrane to provide stability for needle 140. Also, component 902 comprises an arc shaped piece 942, which provides axially disposed support for rear component 904 while such is joined with forward component 902. As is the case of fore part 190 seen in FIG. 7, forward component 902 is slidably affixed to needle 140.

Rear component 904 further comprises a secure attachment to needle 140, a hub 944 to which an elastic tube 180 is attached. Proximal to the sharp end of needle 140 is a convex conical surface 946, which is shaped to mate with a concave conical surface 948 disposed inward from line 948' on cylindrical body 912 to provide a sterility barrier for needle 140 while component 902 is joined to component 904.

Needle 140 is extended for use by pulling a needle cover attached to threaded segment 908 as previously described. In a prior to use rest state, component 904 is affixed to component 902 by latching member 922 during manufacture of part 900. When part 900 is brought forward to extend needle 140 for use, wing latches 914 and 914' are caught upon catches (not shown) to securely and permanently affix component 902 in a forward position At the end of a medical procedure when it is desired to retract needle 140 for safe containment, button 938 is depressed through the distortable membrane to bend strut 918 into opening 936, cant latch member 922 away from surface 928, and thereby release component 904 and associated needle 140 for retraction by the force of energy contained in elastic tube 180.

Similar to other hubs and needle related parts, both components 902 and 904 are preferably injection molded from synthetic resinous materials. Materials which are compatible with requirements for components 902 and 904 are well known in the needle hub manufacturing art.

Standard and Pre-filled Syringe Embodiments

Figure 49:
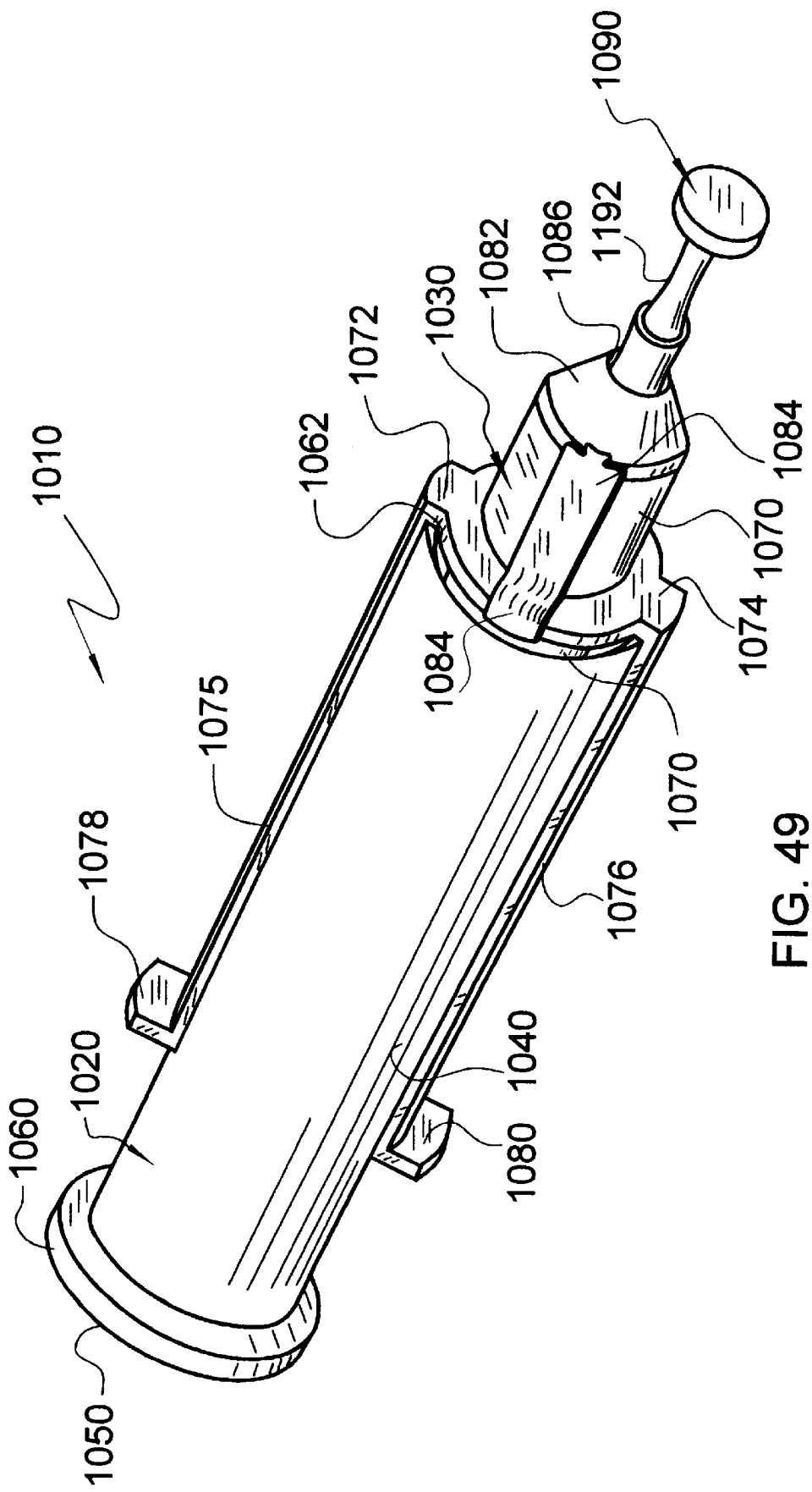
FIG. 49 is a perspective of a combination syringe and medical needle apparatus.

Reference is now made to FIG. 49 wherein an embodiment according to the invention of a combination syringe/medical needle apparatus 1010 is seen. As illustrated in FIG. 49, combination 1010 comprises a syringe barrel 1020 and a plunger part 1030.

Barrel 1020 comprises a hollow elongated tube member 1040 and a distal end 1050 which is transversely disposed to member 1040. Preferably, a section 1060 at distal end 1050 has a generally larger radius of curvature than the curvature of member 1040 to permit barrel 1020 to be facilely gripped and moved relative to part 1030. Proximally, an end 1062 provides an entry and exit orifice 1064 for plunger part 1030.

Plunger part 1030 also comprises a hollow elongated tube member 1070 which is sized to fit-without-touching-inside member 1040. Extending radially outward from member 1070 is a securely affixed appendage 1072, which is disposed to be in near proximity, but not to touch end 1062. Preferably, appendage 1072 comprises a proximal face 1074 which is generally large enough to be gripped with a fore finger and an index finger for use in single handed syringe manipulation.

Extending distally from appendage 1072 and juxtaposed to member 1040 are a pair of opposing members 1075 and 1076, which end abruptly in outwardly distending handles 1078 and 1080, respectively. The length of members 1075 and 1076 are dependent upon the length of barrel 1020 and are adjusted to provide facile single handed syringe manipulation. Such adjustments are well known in the art of syringe design. Outward extension of handles 1078 and 1080 should be sufficient to provide digitary control using the index and middle fingers.

Proximally plunger part 1030 terminates in a hollow frustoconical nose cone 1082 to which a shield 1084 is attached. The purpose and function of shield 1084 is disclosed in detail hereafter. Nose cone 1082 comprises an axially disposed orifice 1086 through which a medical apparatus puller 1090 operates to extend a medical needle apparatus 1100, an example of which is seen in cross section in FIG. 50.

Figure 50:
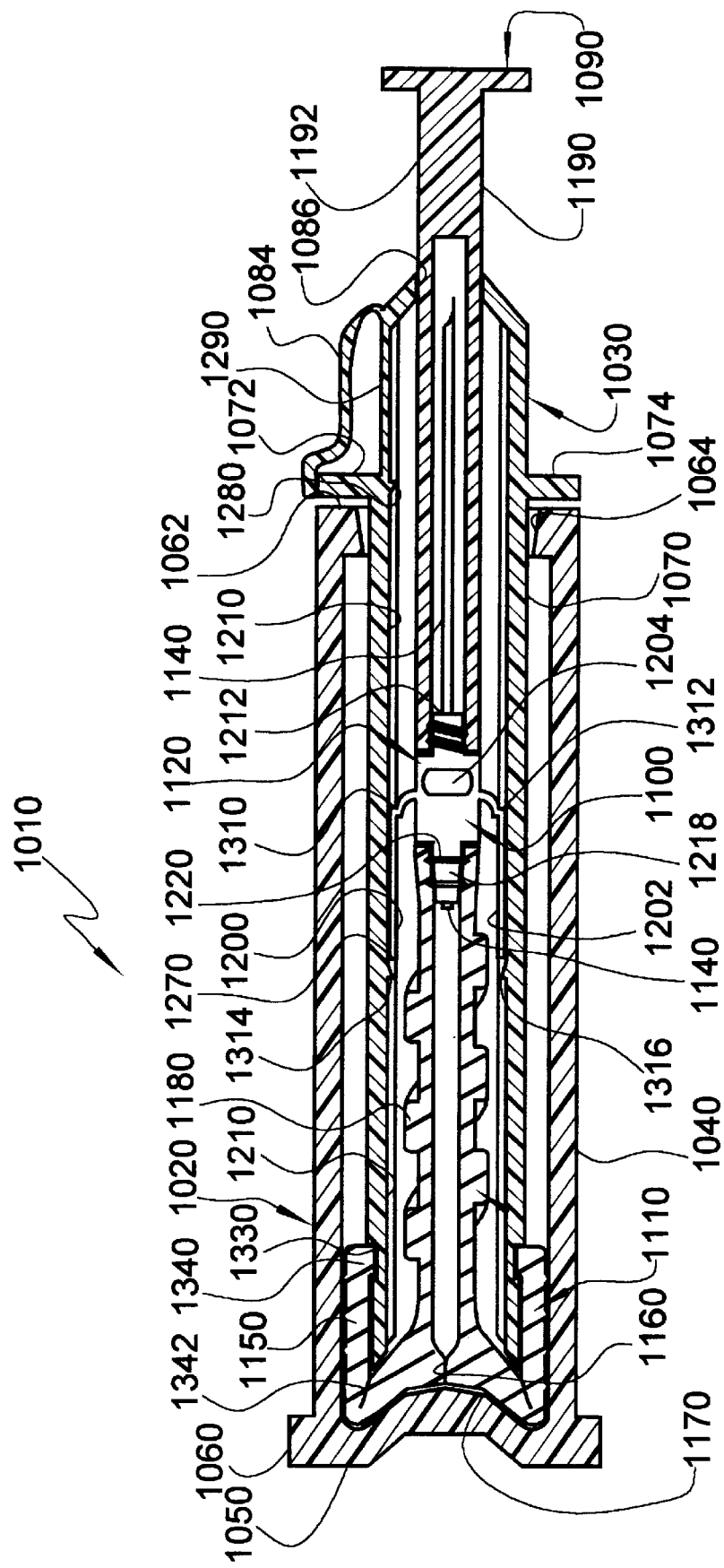
FIG. 50 is a cross section of a lateral elevation of the combination seen in FIG. 49.

Referring to FIG. 50, medical needle apparatus 1010 is seen to comprise a pliant and stretchable elastic component 1110, a hub element 1120 and a hollow medical needle 1140. While component 1110 may be made as a number of separate parts, it is presently preferred that component 1110 comprise integrally formed and attached parts which functionally perform as a seal 1150, a normally closed valve 1160, an interfacing surface 1170 to a ventral surface of a posterior portion of barrel 1020, and an elastic tube 1180. In the embodiment of FIGS. 49 and 50, valve 1160 is a slit valve.

As is common with standard contemporary disposable syringes, member 1040 comprises an opening 1064, comprising a frustoconical shape which is conducive to passage of seal 1150 in a direction into member 1040, but unfavorable to release of seal 1150 from member 1040.

In this case, puller 1090 is a needle cover 1190 which physically and asceptically protects needle 1140. A portion 1192 of cover 1190 is exteriorly accessible through orifice 1086.

Figure 51:
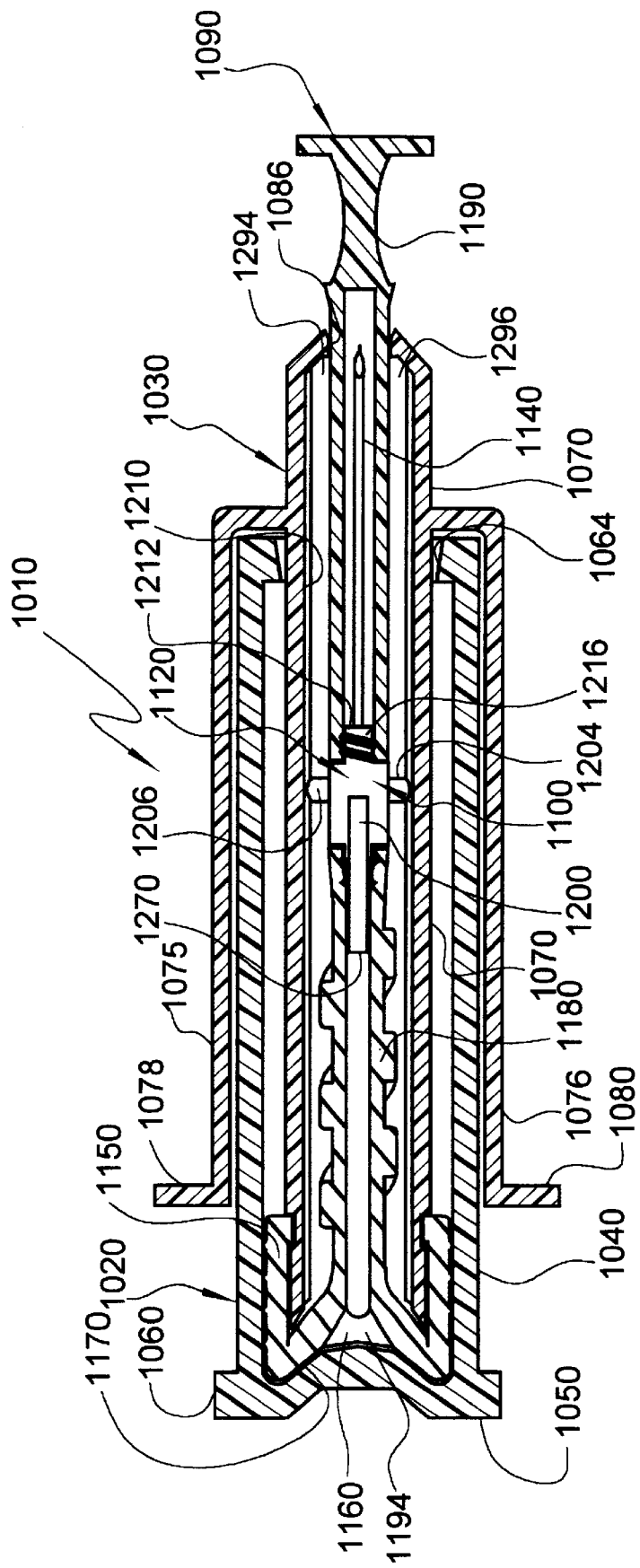
FIG. 51 is a cross section of a lateral elevation or the combination seen in FIG. 49 but rotated 90° relative to that seen in FIG. 50.

In FIG. 51, device 1010 is seen in cross section rotated 90° about the long axis of needle 1140. This rotation gives visibility to opposing members 1075 and 1076. The rotation also gives visibility to a planar face 1194 of slit valve 1160.

Referring now to FIGS. 50 and 51 in combination, hub element 1120 is seen to comprise a superior wing part 1200, an inferior wing part 1202 and a pair of side supports 1204 and 1206. Each wing part 1200 and 1202 and each side support 1204 and 1206 is designed to slide along an inner surface 1210 of hollow elongated tube member 1070 thereby providing stability and support for hub element 1120 and medical needle apparatus 1100. On a proximal end 1212, hub element 1120 comprises a releasible (e.g., threaded) connector 1216 for a secure, but releasible attachment to puller 1090. On a distal end 1218, hub element 1120 comprises a tube gripping hub member 1220 for attachment to elastic tube 1180. While it may be necessary for some materials used in fabrication of tube 1180 to use an adhesive for attachment to hub member 1220, adequate attachment has been achieved by physically stretching tube 1180 over a slightly larger hub member 1220.

Figure 54:
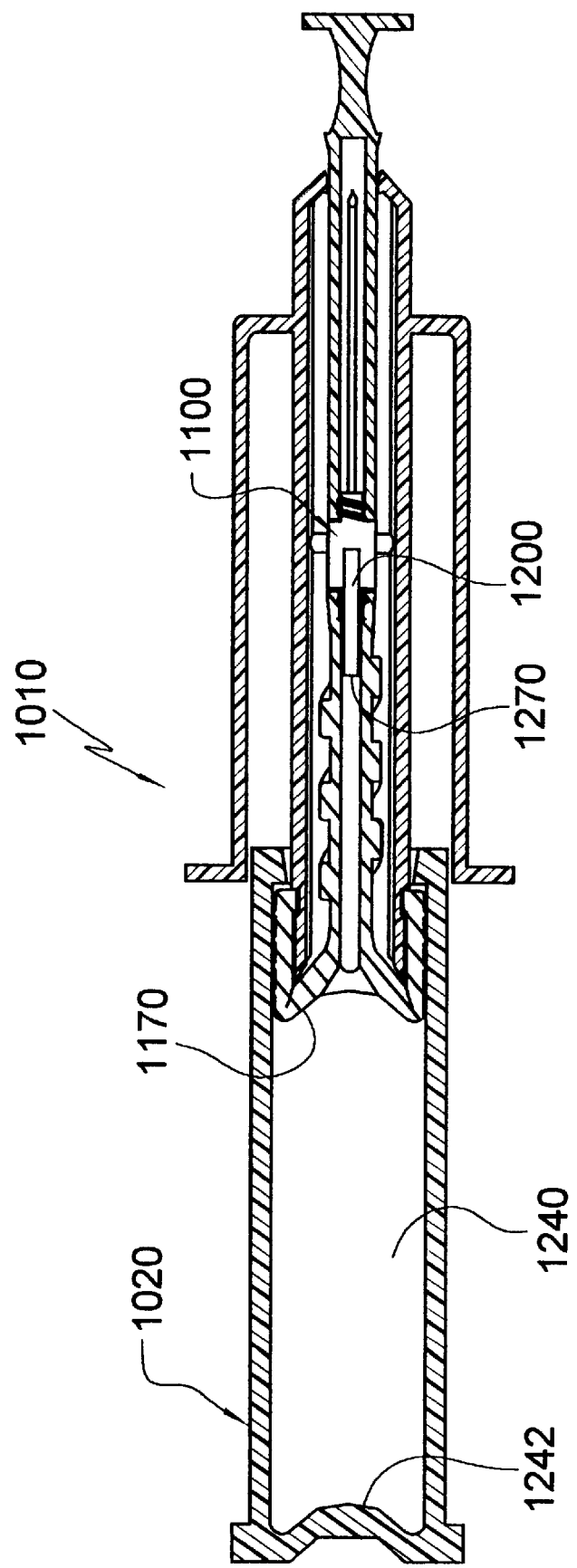
FIG. 54 is a cross section of the combination in an axial orientation as seen in FIG. 51, but with a barrel section extended outward from a plunger section.

FIGS. 53, 54 and 55 illustrate apparatus and methods for extending medical needle apparatus 1100 to a position where needle 1140 is disposed for use, and whereby valve 1160 is opened to permit flow of fluid therethrough are seen. In FIG. 55, medical needle apparatus 1100, with medical needle 1140 securely attached to hub element 1120, is extended for disposing needle 1140 in position for use in a medical procedure. Needle cover 1190 by which medical needle apparatus 1100 was extended and thereafter removed, is shown in FIG. 55A Elastic tube 1180 is stretched as apparatus 1100 is extended to store retraction energy and to return needle 1140 into the protective cover at the end of the medical procedure.

The stretching of tube 1180 not only provides a flow path for fluid to and from needle 1180 and stores retractive force for apparatus 1100, but also opens normally closed valve 1160. As seen in FIG. 52, tube 1180 comprises linkages 1222 and 1224 which are integrally attached to slit valve 1160. Thickness of linkages 1220 and 1224 depends upon the size of the inside diameter of tube 1140 and the length and thickness of the face 1194 (and opposing face 1194') of slit valve 1160. Such thickness can be determined without undue experimentation. As seen in FIG. 53, stretching tube 1180 decreases the diameter of tube 1180 and distorts slit valve 1160 to part opposing faces 1194 and 1194', thereby opening valve 1160. While there are other devices and methods for accomplishing the opening of a normally closed valve as tube 1180 is stretched, this particular embodiment is preferred because valve 1160 and tube 1180 are made as a single part.

Figure 56:
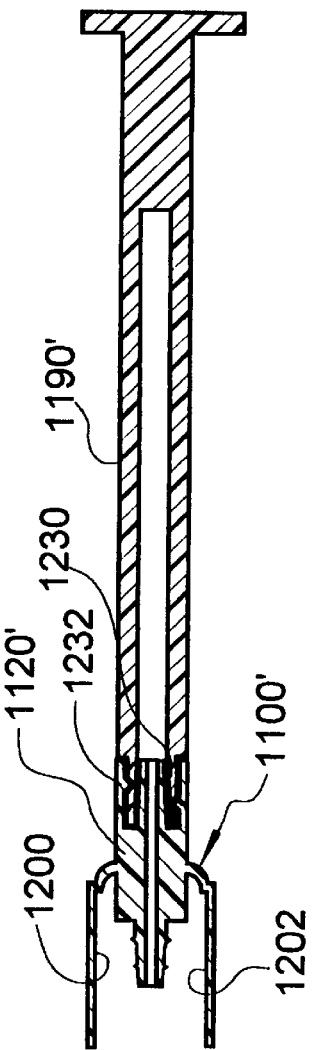
FIG. 56 is a cross section of a hub part of a medical needle apparatus connected via a luer-lock fitting to a part used as a puller to extend the medical needle apparatus.

In some cases, it may be desirable to select a medical needle determined by the situation and procedure rather than have a needle delivered as a predetermined element of a syringe. For this purpose, rather than providing a needle cover 1190, a puller 1190' having a hub apparatus attachment such as that seen as an example in FIG. 56 can be used. A medical needle apparatus 1100' comprising a hub element 1120' is used, rather than the medical needle apparatus 1100 and associated hub element 1120. The major difference is in the hub elements and particularly in the connection to the pullers used. In the case of the embodiment of FIG. 56, puller 1190' comprises a female luer-lock fitting 1230 and hub element 1120' comprises a complementary male luer-lock fitting 1232. The use of luer fittings provides an excellent seal to close any pathway into hub element 1120', as well as providing a compatible connector for affixing a medical needle to hub element 1120' after medical needle apparatus 1100' has been extended for use.

Generally, device 1010 can be used as either a standard syringe or a pre-filled syringe. If device 1010 is simply used as a standard syringe, there is no need to provide access for filling the syringe other than through a medical needle. Also, in this case, there may be no need to provide a normally closed valve, such as valve 1160. In either case, barrel 1020 and interfacing surface 1170 combine to define a space 1240 wherein medical or biological fluid resides either prior to or after a medical procedure.

Though not absolutely necessary it is preferred that barrel 1020 at end 1050 comprise a generally frustoconical inner surface 1242 and that interfacing surface 1170, juxtaposing inner surface 1242, have a complementary shape to facilitate expulsion of gas from space 1240. In the case of the simple syringe application, surface 1242 is formed as a continuous, integral element formed as a part of barrel 1020.

Figure 57:
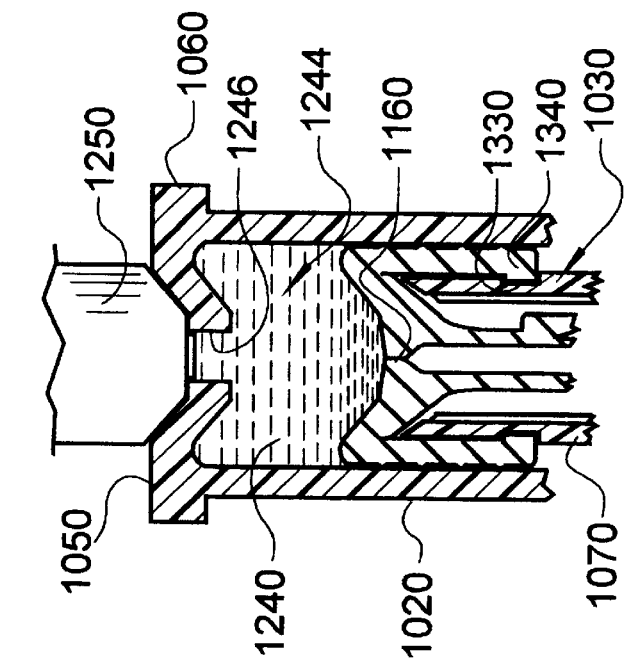
FIG. 57 is a segment of a cross section of a vertically oriented syringe/medical needle apparatus combination having a filler orifice disposed beneath a filler nozzle for the purpose of prefilling the syringe with a medical fluid.
Figure 58:
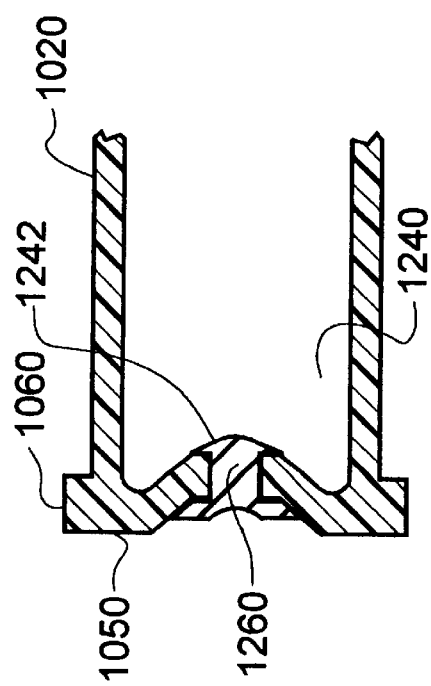
FIG. 58 is a horizontally oriented segment of a cross section of the syringe/medical needle apparatus combination seen in FIG. 57 with a plug placed in the filler orifice.

To augment filling space 1240 with a medical fluid, such as liquid 1244 in FIG. 57, an orifice is provided, such as orifice 1246 seen in FIGS. 57 and 58. A preferred method for pre-filling device 1010 is to orient device 1010 vertically with the proximal portion downwardly disposed. A pliant nozzle, such as nozzle 1250 in FIG. 57, is sealably disposed against end 1050 and orifice 1246. While surface 1170 is in contact with surface 1242, a connection to a vacuum is made through nozzle 1250 to evacuate gas from space 1240. Thereafter, a connection is made with a vessel containing the liquid to be stored in device 1010 through a low resistance pathway via nozzle 1250. Plunger part 1030 is moved downward to draw liquid 1244 into space 1240. Other than access through orifice 1246, there is no escape path for liquid form device 1010 until valve 1160 is opened. Also, a secondary seal can be provided, such as by luer-lock fittings 1230 and 1232, to prevent evaporative escape of liquid.

Once space 1240 is filled with a predetermined volume of liquid 1244, a plug (such as plug 1260 seen in FIG. 58) is used to seal orifice 1246 from further liquid flow. As one who is skilled in the art of filling and sealing medical vials would understand, this method of filling and sealing is only one of many methods available in the art. Other such methods may be used within the scope of this invention to safely and effectively fill and ready device 1010 for use as a pre-filled syringe.

With the exception of medical needle apparatus 1100 and 1100' extension and retraction, device 1010 is generally used as a standard medical syringe, requiring but a minimum of training. Generally, puller 1090 is drawn outward from plunger part 1030 to extend medical needle apparatus 1100 or 1100' for use. As illustrate in FIG. 55 (see also FIGS. 50, 51, 54, 59, 60 and 61), hub element 1120 (and 1120') comprises awing part 1200 which extends outward toward inner surface 1210. Preferably, wing part 1200 is slightly compressed inside plunger part 1030 to retain a moderate outward pressure against surface 1210.

Wing part 1200 comprises a distal blunt end 1270 special formed to provide a latching contact. When medical needle apparatus 1100 (or 1100') is drawn outward from plunger part 1030 to a position where medical needle 1140 is made ready for use, end 1270 is brought into latching contact with a protrusion 1280 on inner surface 1210. Protrusion 1280 acts as a catch for end 1270.

Figure 60:
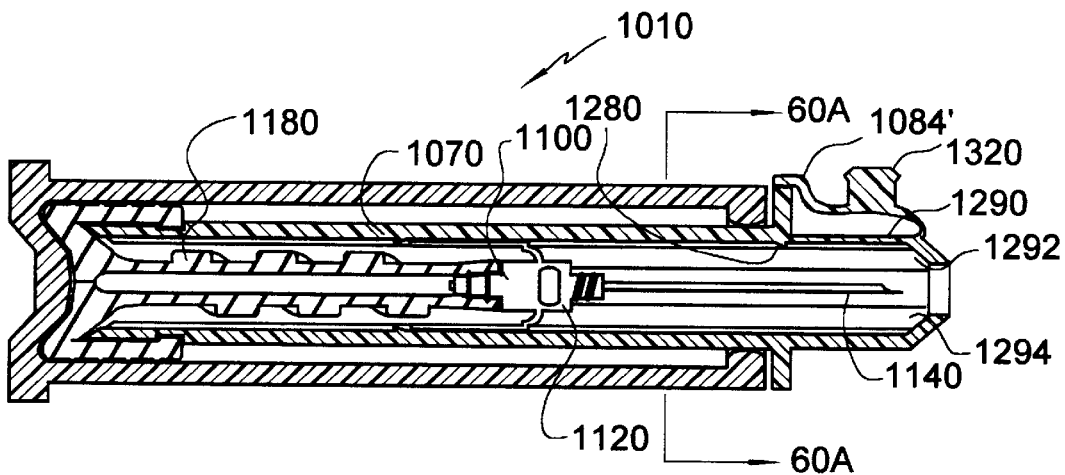
FIG. 60 is a cross section of a lateral elevation similar to the combination seen in FIG. 50, but with a plug disposed upon a shield located above and protecting a depressible, distortable section of the plunger section.
Figure 61:
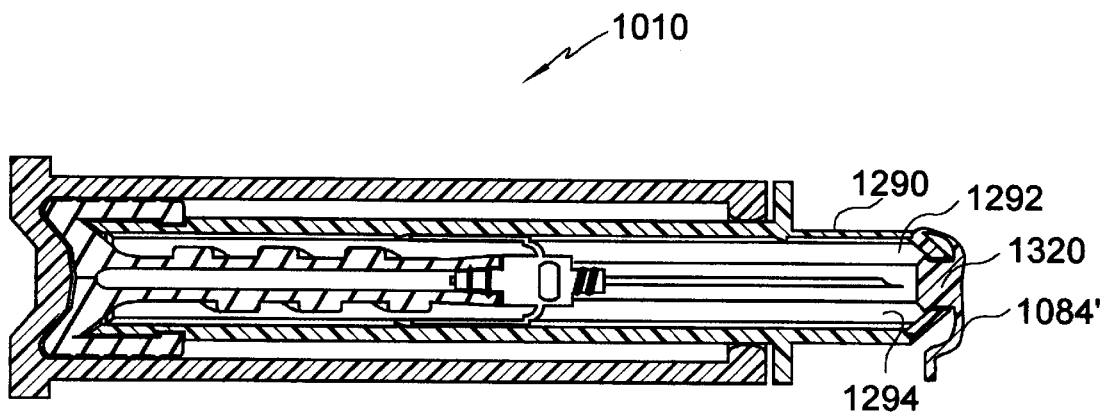
FIG. 61 is a cross section of the lateral elevation of FIG. 60 with the shield rotated to affix the plug into the plunger section.

A thinned depressible section 1290 is in an area of plunger part 1030 immediately proximal to protrusion 1280. Section 1290 is sufficiently thinned to be facilely depressed in a manner and with forces consistent with depressing a key on a membrane keyboard. By such depression, wing part 1200 at end 1270 (acting as a latch) is released from protrusion 1280 (a catch). Energy stored in extended tube 1180 automatically causes retraction of medical needle apparatus 1100 (or 1100') to withdraw medical needle 1140 inside hollow tube member 1070. Such a retracted needle 1140 is shown in FIGS. 60 and 61.

Dangerous needle stick problems related to recovering bared medical needles have resulted in rules being made and enforced which ban recovering medical needles unless special conditions or equipment make such recovering safe, both for the care giver and the patient. However, there are many reasons why it would be desirable to recover a medical needle so that it can be used a plurality of times. Such reasons include, the double use of a medical needle to pre-fill a syringe through the medical needle at a site remote from the patient and then transport the filled syringe for delivery to the patient, and also delivering medication from the same syringe to the same patient following a procedure comprising incremental steps.

In each of the above cases, the medical needle should be recovered in the interim before a subsequent use. For greatest safety, the medical needle should be retracted into a safe housing, such as into the hollow of plunger part 1030 immediately after each use and, in fact, directly from the patient, as is possible with this novel invention. For maximum safety, a medical needle should only be uncovered immediately prior to use and immediately sheathed thereafter.

Figure 60A:
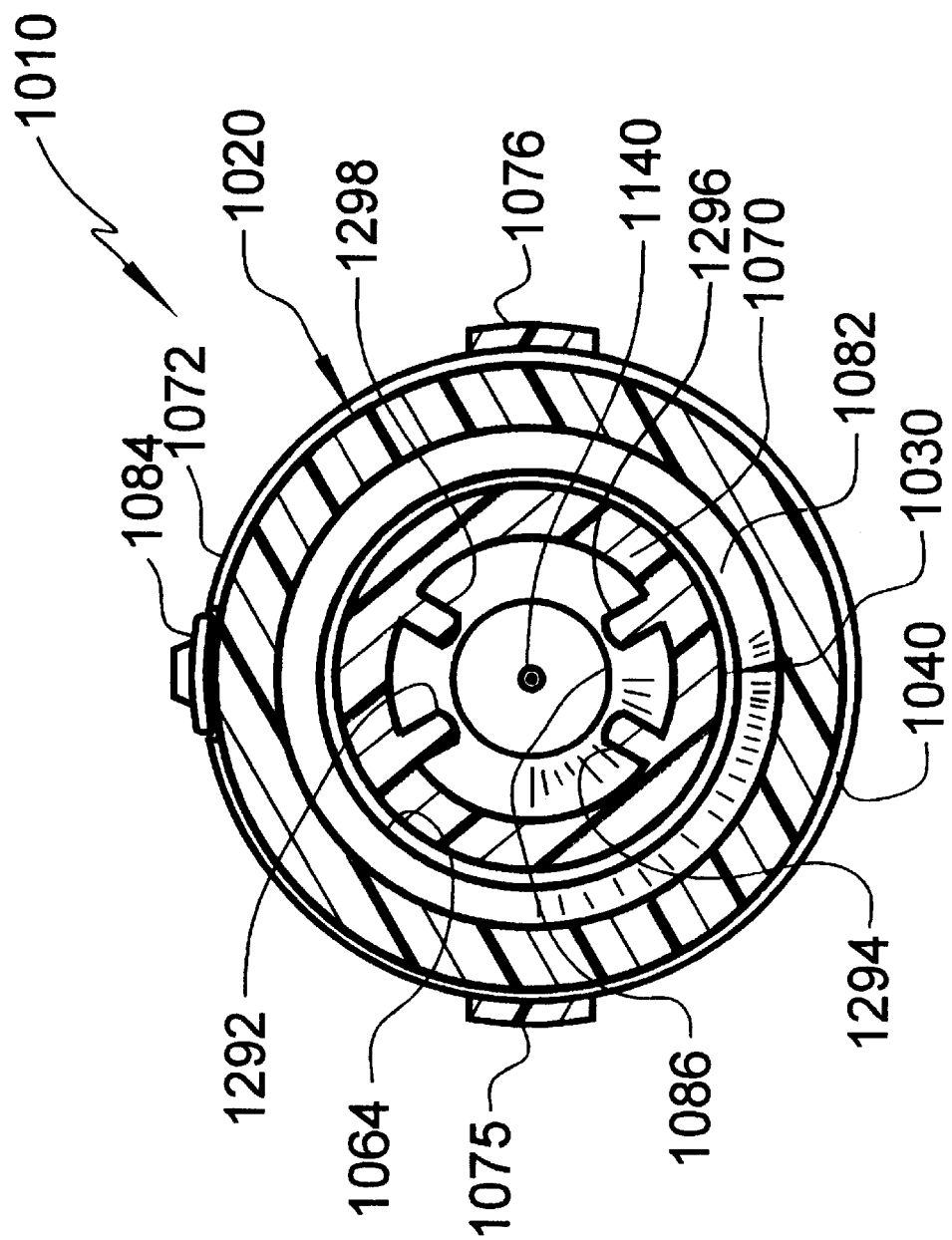
FIG. 60A is a cross section taken along lines 60A—60A in FIG. 60.

To provide for safely baring and recovering the needle, a retracted needle is recovered by the following inventive method using device 1010. In FIG. 60, medical needle 1140 and hub element 1120 are retracted to return needle 1140 to a safely sheathed condition. As seen in FIG. 60A, elongated tube member 1070 of plunger part 1030 comprises a plurality of inwardly disposed ribs 1292, 1294, 1296 and 1298. Outwardly extending parts of hub element 1120, wing parts 1200 and 1202 and side supports 1204 and 1206 are constrained from axial displacement by ribs 1292, 1294, 1296 and 1298.

Wing part 1200 is constrained by ribs 1292 and 1298, wing part 1202 by ribs 1294 and 1296, side support 1204 by ribs 1298 and 1296 and side support 1206 by ribs 1292 and 1294. Inward displacements of ribs 1292, 1294, 1296 and 1298 are disposed to centrally constrain, but allow linear displacement of hub element 1120 and needle cover 1190. Further, wing parts 1202 and 1204 and side supports 1204 and 1206 combine to restrain needle 1140 in a substantially coaxial direction relative to the long axis of tube member 1070.

When needle 1140, wing parts 1202 and 1204, and side supports 1204 and 1206 are so constrained, needle cover 1190 can be safely and effectively re-inserted through orifice 1086, rotated to reengage connector 1216, and thereby be repositioned for re-extending needle 1140 for subsequent use. Both conditions necessary for safely and effectively recovering needle 1140 with needle cover 1190 are met as, first, the needle is safely sheathed while the recovering act is performed and, second, cover 1190 is biased away from contact with needle 1140 to protect sterility of needle 1140 during the recovery process.

Of course, parts of needle cover 1190, which may come in contact with needle 1140 when cover 1190 is removed after extending needle 1140, must be designed to remain uncontaminated while cover 1190 is removed. As one who is skilled in the art of handling needle covers well understands, there are procedures currently known in the art for handling and protecting removed needle covers in such circumstances.

As is well known in the art of using and disposing of medical needles, it is often desirable to remove the option of further use of a medical needle after a medical procedure is completed. In those cases where needles are added to a syringe prior to retraction, a needle cover 1190 or puller 1190' cannot be reconnected to a hub element. In that case, the needle is safely retained and cannot be reused. However, in the case of a syringe designed for needle reuse as disclosed above, another element must be added to eradicate options for reuse.

Three different embodiments which can be used for destroying subsequent operability of device 1010 are disclosed hereafter. First, attention is drawn to FIG. 62, in which only the parts necessary to describe a way of permanently locking needle cover 1190 into tube member 1070 are shown. As illustrated in FIG. 62, nose cone 1082 comprises an inwardly disposed annular shoulder 1300, the surface of which is transverse to the long axis of needle 1140 and tube member 1070. As disclosed above, the travel of needle cover 1190 is constrained to be along the long axis of needle 1140. Needle cover 1190 comprises a raised shoulder 1302 which incorporates a proximally disposed transverse face 1304. Since tube 1180 will buckle when forced compressively and the material of nose cone 1082 will give sufficiently when needle cover 1190 is forcibly pushed into tube member 1070, such inward movement ultimately causes shoulder 1300 to lock against face 1304, thereby sealing device 1010 against further use.

Elements used in a second method of eradicating the possibility of further use after completion of a medical procedure are shown in FIG. 50. Proximally disposed sections of wing parts 1200 and 1202 each comprise a transversely disposed latching segment 1310 and 1312, respectively. Complementary catches 1314 and 1316 are disposed upon the inner surface 1210 of tube member 1070. These catches and latches are so placed that forcing needle cover 1190 inward into tube member 1070 with sufficient force and displacement to cause catches 1314 and 1316 to catch latches 1310 and 1312, respectively, securely constrains needle 1140 inside tube member 1070, thereby negating further use.

A plug 1320, added to shield 1084 (to form shield 1084'), is seen in FIGS. 60 and 61 to provide a third method for sealing device 1010 against further use. As seen in FIG. 60, shield 1084' comprises plug 1320 vertical and exteriorly disposed such that after needle 1140 is finally retracted by lifting shield 1084' for access to section 1290 to cause the retraction, plug 1320 is rotated approximately 90° and forced into tube member 1070. Plug 1320 comprises complementary surfaces to a catching surface, such as shoulder 1300, to securely affix plug 1320 and to close device 1010 against further use.

Of particular importance is the use of device 1010 as a pre-filled syringe. Sealed arts must be tightly closed to maintain the effectiveness of medical fluids contained within space 1240. (See FIG. 57.) Plug 1260, sliding seal 1150, valve 1160, cover 1190, and puller 1190' connections to medical needle apparatus 1100 should all provide a substantially closed environment for the medical fluid contained in the pre-filled syringe. Only when medical needle apparatus 1100 is extended for use should valve 1160 open. It is also preferred that the medical fluid is exposed to an external environment only when puller 1190' or cover 1190 are removed.

To ready device 1010 for use, medical apparatus 1100 is extended by pulling either cover 1190 or puller 1190' until latch 1270 is caught by catch 1280, thereby opening valve 1160. Either cover 1190 or puller 1190' is then removed. If puller 1190' is used, a medical needle having a luer fitting is connected to medical needle apparatus 1100.

As is common practice in medical injections, all gas is purged from the fluid pathway by vertically disposing device 1010 with the medical needle 1140 pointed upward, and decreasing volume 1244 until the medical fluid is seen to escape needle 1140. A predetermined volume, not necessarily all of the volume left in space 1240, is dispensed. Upon completion of this segment of the procedure, medical needle 1140 is retracted by depressing section 1290.

As disclosed above, needle cover 1190, having been protected from unacceptable contamination, can be reinserted and reconnected to recover medical needle apparatus 1100 for subsequent use of the pre-filled syringe. Upon a final step of using device 1010, cover 1190 is forcibly inserted into tube member 1070 to secure needle 1140 from firer use. Alternatively, plug 1320 is securely affixed into orifice 1086.

Figure 59:
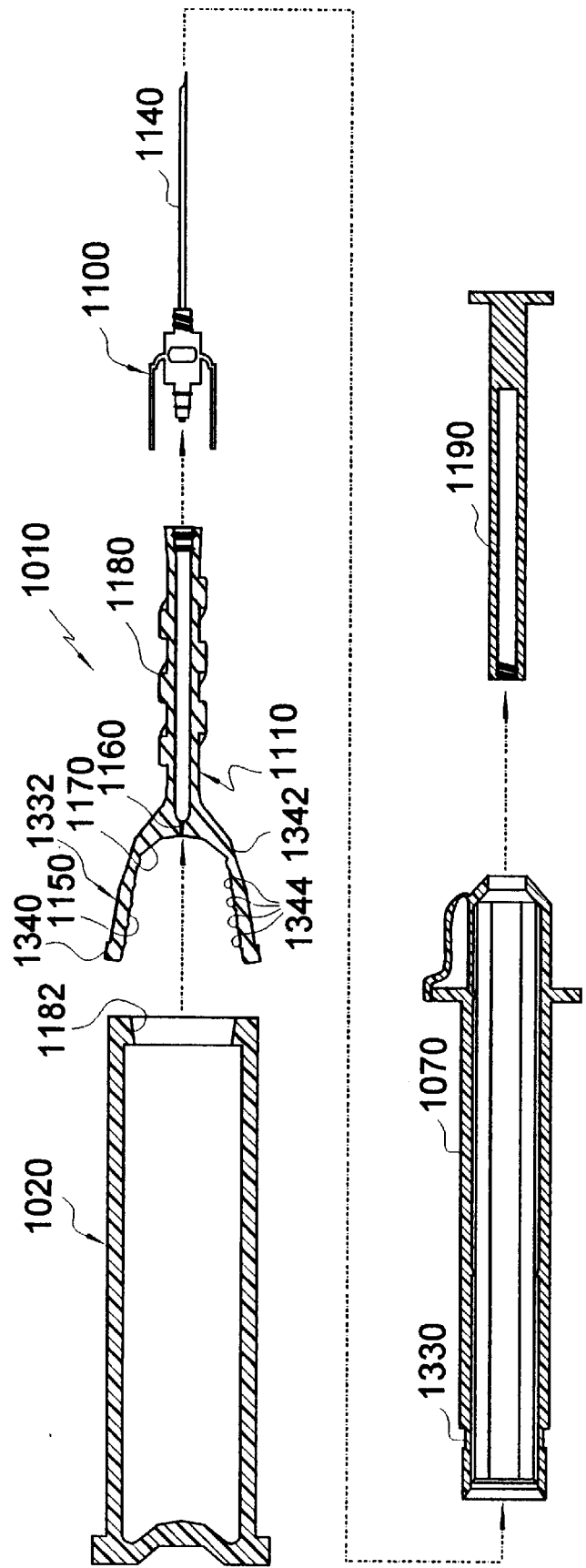
FIG. 59 is an exploded view of the combination seen in FIG. 49 with only the assembly step of attaching a medical needle to a hub completed.

Referring now to FIG. 59, device 1010 assembly steps (of course all manufacture and assembly should be performed under appropriately clean conditions) are seen to comprise:

1. Fabrication by injection molding or other high volume, low cost process hub element 1120 (or 1120'). It is preferred to make medical hub element 1120 from a synthetic resinous material which has sufficient flexibility and strength that extend parts (1200 and 1202)

can be used as depressible latches. While no part of hub element 1120 must contact the medical fluid, it is preferred that the selected material be inert both to bodily fluids and medically injectable fluids. Such material may be selected from an appropriate grade of polyurethane, polypropylene and polyethylene.

2. Medical grade steel, such as the steel currently used in disposable medical needles should be used for needle 1140. When the medical needle 1140 is provided as an integral part of hub element 1120, needle 1140 is preferably securely affixed to hub member 1220 by adhesive processes currently well known in the art of medical needle fabrication. When the medical needle is attached after extension of apparatus 1100, hub element 1120' comprises a luer-lock fitting to be connected initially to puller 1190'.

3. The functions of component 1110 may be performed by a plurality of parts. When component 1110 is made as a single, generally cylindrical, integral part it comprises seal 1150, normally closed valve 1160, interfacing surface 1170 to a ventral surface of a posterior portion of barrel 1020 and an elastic tube 1180. Starting from a proximal end, elastic tube 1180 is normally closed (unless tube 1180 is stretched) by valve 1160. Valve 1160 opens on a distal side to interfacing surface 1170, which extends distally to form seal 1150. Operation of seal 1150 as a fluid control device has been disclosed above and will not be repeated here. Tube 1180 also functions as a regurgitant fluid control device using processes disclosed in detail hereafter. Component 1110 may be made from a plurality of currently available products such as medical grade latex and silicone rubber. However, new and superior products are continuously being introduced into the marketplace. The material should have the following characteristics: effectively inert to both bodily fluids which might contact it; extendable to a length which permits latching apparatus 1100 in a forward condition and at which length it will retract an inserted needle 1140; and able to form an effective seal for seal 1150 and valve 1160. Component 1110 is affixed directly to hub element 1120 (or 1120') via hub member 1220.

4. The joined combination of apparatus 1100 and component 1110 is then inserted into the hollow of tube member 1070, with wing parts and side supports of apparatus 1100 disposed as previously described. As shown in FIG. 59, tube member 1070 comprises an annular groove 1330. Section 1332 of component 1110 comprises seal 1150 with an annular ridge member 1340 (an integral o-ring) that is complementary to groove 1330. Also, section 1332 comprises a thinned, foldable annular region 1342 which permits section 1332 to be folded to double about the exterior surface of tube member 1070. Component 1110 is securely affixed about tube member 1070 with member 1340 residing in groove 1330 to form seal 1150 thereupon. Component 1110 comprises a series of annular rings 1344 to enhance performance of seal 1150.

5. Once component 1110 is affixed to tube member 1070, needle cover 1190 (or puller 1190') is affixed to hub element 1120 (or 1120').

6. Finally, seal 1150 portion of component 1110 and tube member 1070 is forced through opening 1064 to complete assembly of device 1010. Barrel 1020 is shown in FIG. 59 as a barrel having a closed distal end. Of course, barrel 1020 can also have an open, but closable distal end, as earlier disclosed. Though other materials may be used, needle cover 1190 (puller 1190') is preferably made from medical grade polypropylene. Similarly, plunger part 1030 is preferably made from medical grade polypropylene, although other materials which have similar depressible qualities of thin members may also be used within the scope of the invention. As seen in FIG. 62, plunger part 1030 may be made from two separately injection molded parts and then joined later. Ultrasonic bonding is preferred. Selection of materials for barrel 1020 is highly dependent upon fluids stored therein in the pre-filled application. Materials may range from synthetic resinous materials to medical grade glass. If a material which is not absolutely shatterproof is not used, at least a protective cover should be placed over section 1060 at distal end 1050. (Not shown.)

7. In a fully assembled device, it is preferable to physically secure cover 1190 (or puller 1190') to nose cone 1082 by heat staking or the like to provide a sterility barrier.

A method for restricting the volume of a stretched tube 1180 to be less than the volume of tube 1180 in a relaxed state was set forth previously in the detailed description of FIGS. 43–46, setting forth Equations 2–14s (prior reference made to tube 180).

Yet Another Phlebotomy Embodiment

Figure 63:
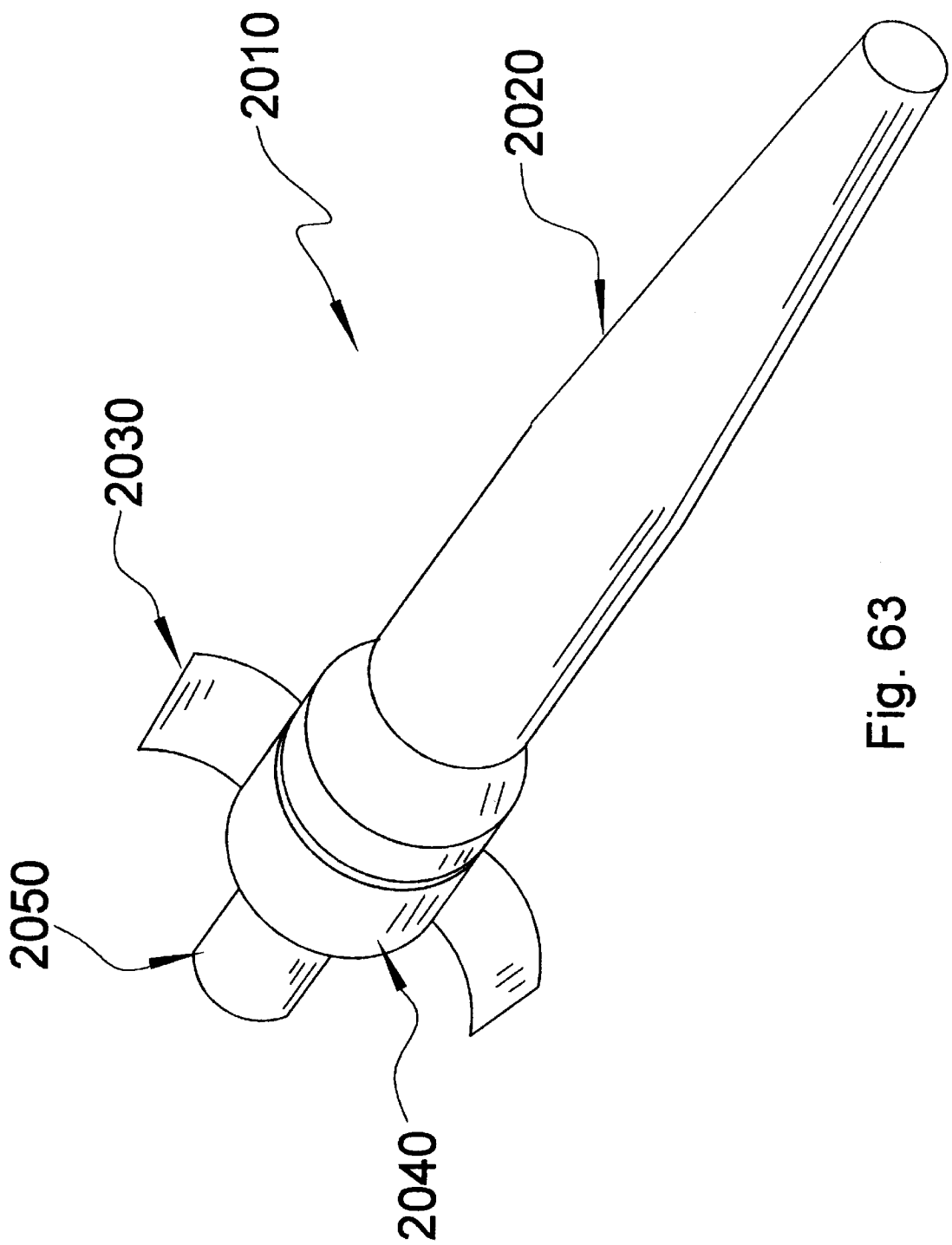
FIG. 63 is a perspective of a safety replacement needle apparatus for a medical phlebotomy procedure.

Reference is now made to FIG. 63 wherein an embodiment of a disposable, self-retracting phlebotomy needle assembly 2010 is seen. As manufactured and transported, assembly 2010 comprises aback, rearwardly disposed or distal cover 2020, a seal 2030 (seen broken free for clarity of presentation), a front or forwardly disposed hub 2040 and a front, forwardly disposed or proximal cover 20O0. Other parts, hidden within assembly 2010 are seen in cross section in FIG. 64. These internal parts comprise a back or rearwardly disposed hub 2060, a phlebotomy needle 2070 securely affixed to hub 2060, an elastic tube disposed about needle 2070 and securely affixed to hubs 2040 and 2060, a snubber 2080 disposed about a distally sharpened end 2082 of needle 2070 and a sheath 2090 which protectively encloses snubber 2080 and end 2082.

Figure 74:
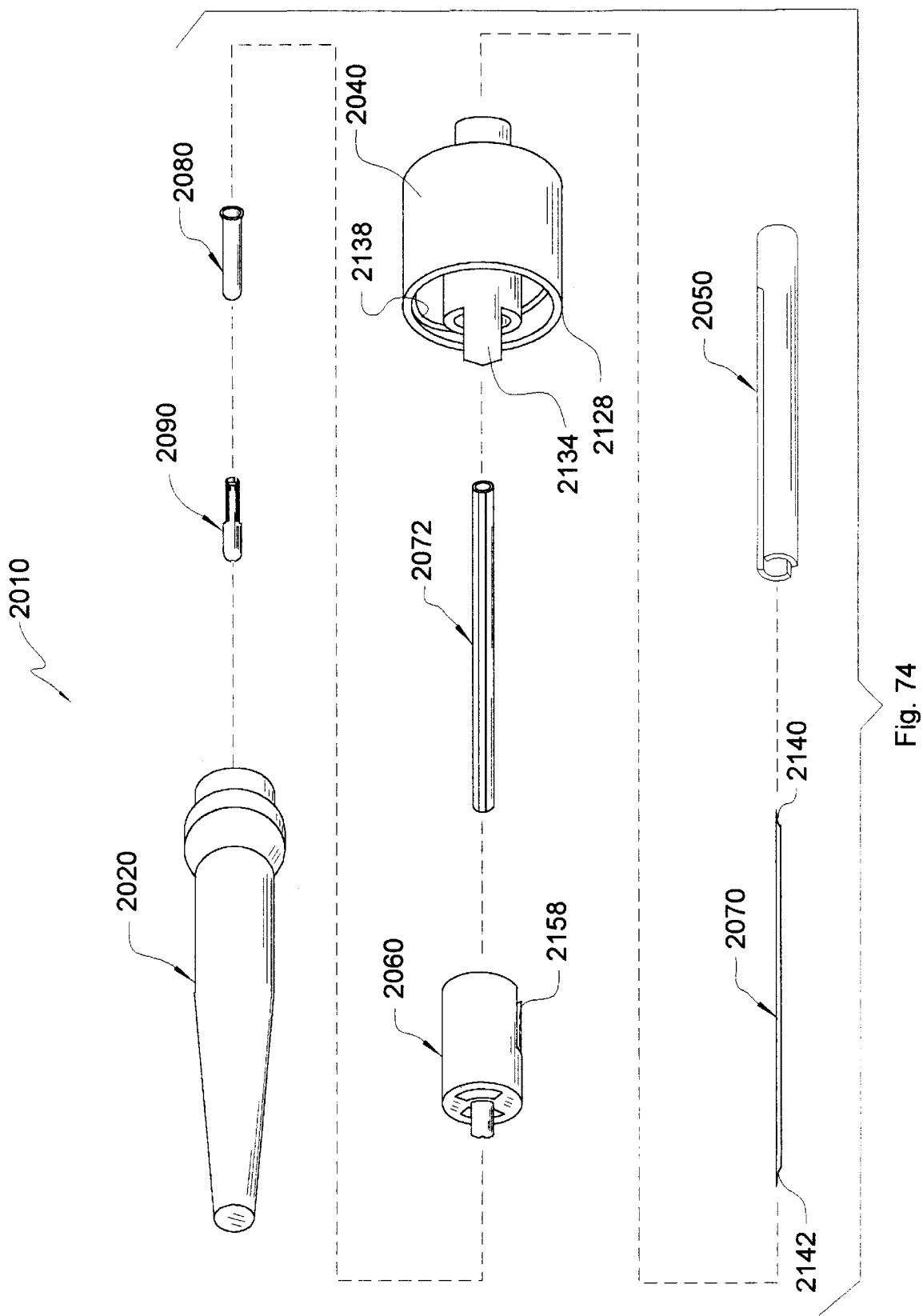
FIG. 74 is an exploded perspective of the phlebotomy needle components seen in FIG. 64.

Each of the above named parts of assembly 2010 are seen as individual components in FIGS. 65–73 and an exploded view of all of the parts in an exploded configuration is shown in FIG. 74.

Figure 64:
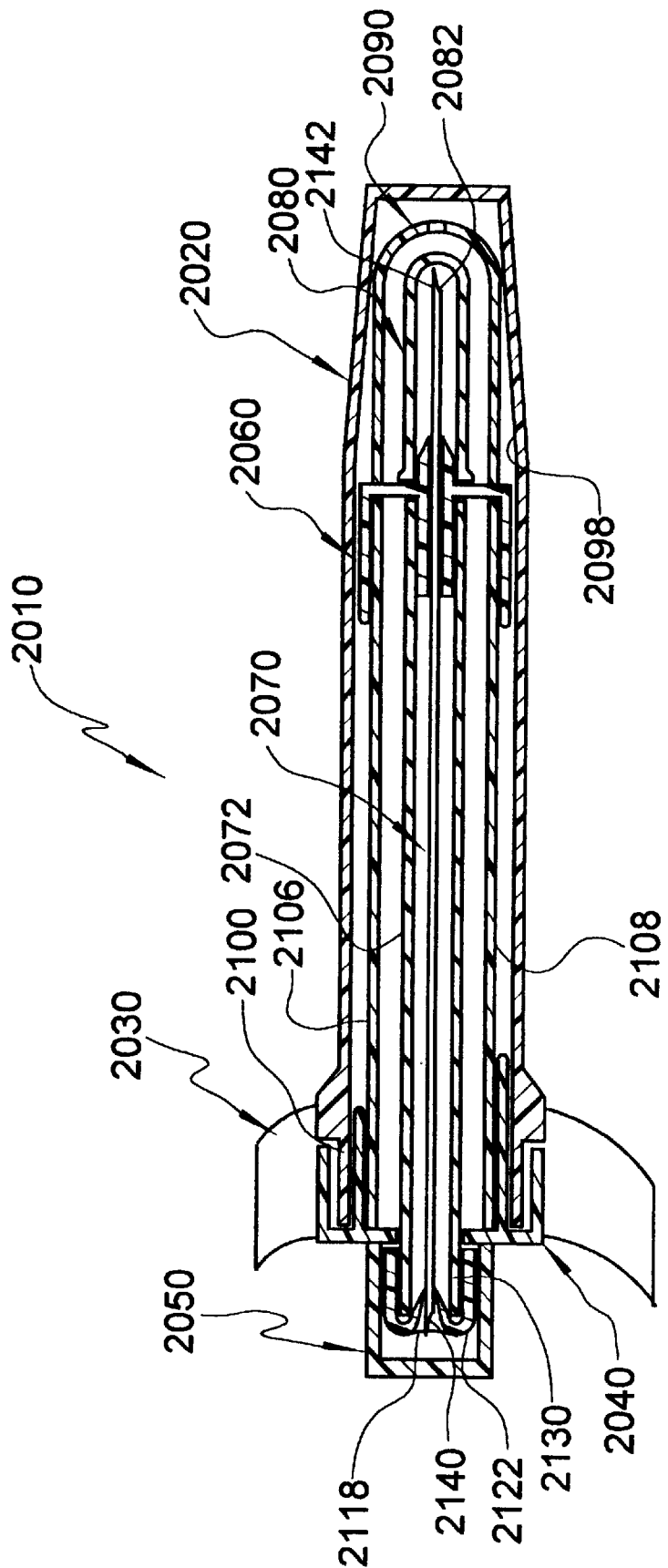
FIG. 64 is a cross section of the apparatus seen in FIG. 63.
Figure 65:
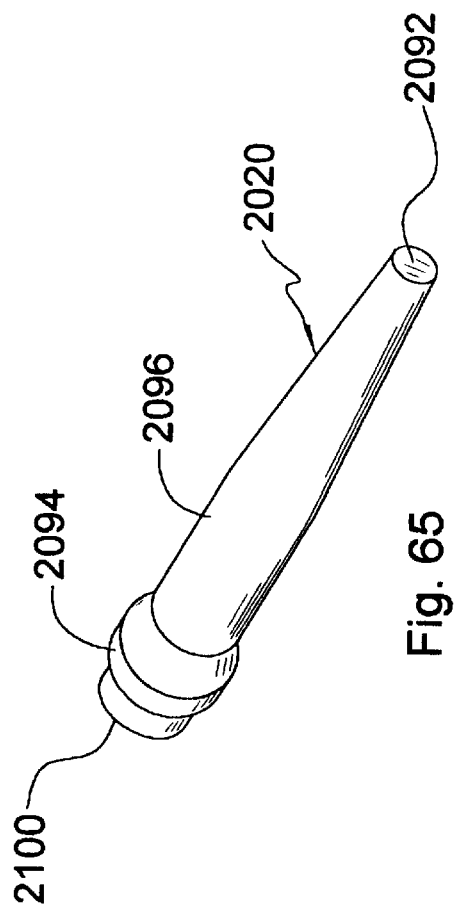
FIG. 65 is a perspective of a back cap of the apparatus seen in FIG. 63.

Referring to FIG. 65, back cover 2020 comprises an elongated, cylindrical housing which having a blunt distal end 2092 attached to a raised portion 2094 by an elongated cylindrical section 2096. Cover 2020 further comprises a hollow interior surface 2098, shown in FIG. 64. Proximally, cover 2020 necks down to a hollow cylindrical section 2100 of smaller radius than portion 2094. The purpose and function of section 2100 is disclosed hereafter. Back cover 2020 is preferably made from a resilient, structurally sound synthetic resonant material. For example, medical grade polypropylene may be used, but other plastic materials such as acrylics and polycarbonates can be used when economies of materials cost are compatible with resultant parts cost.

Figure 66:
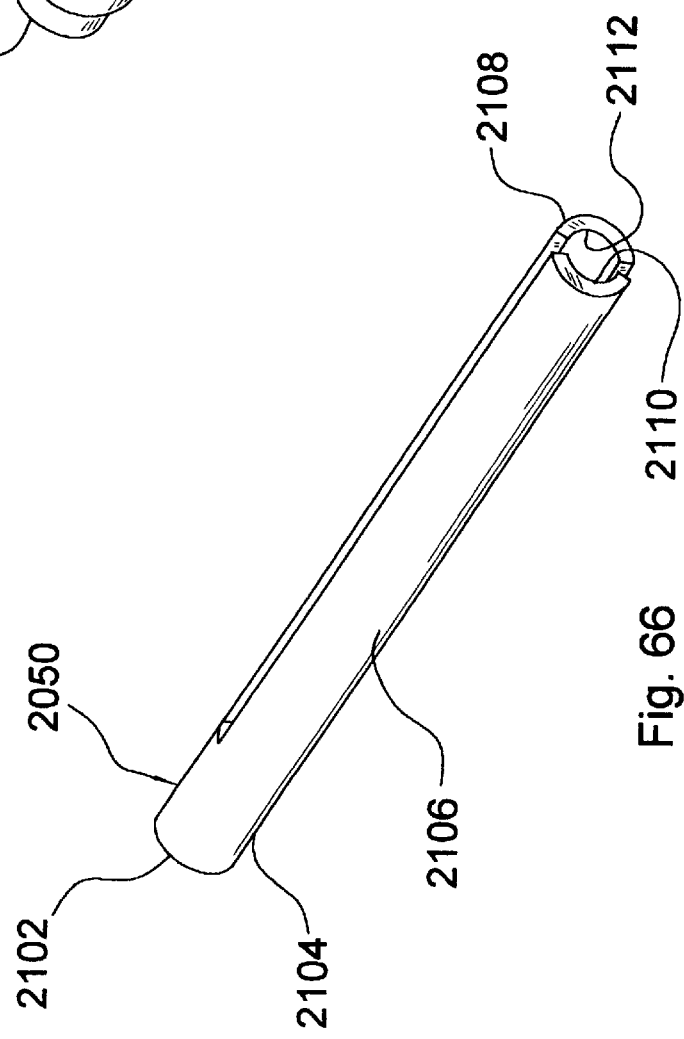
FIG. 66 is a perspective of a front cap of the apparatus seen in FIG. 63.
Figure 68:
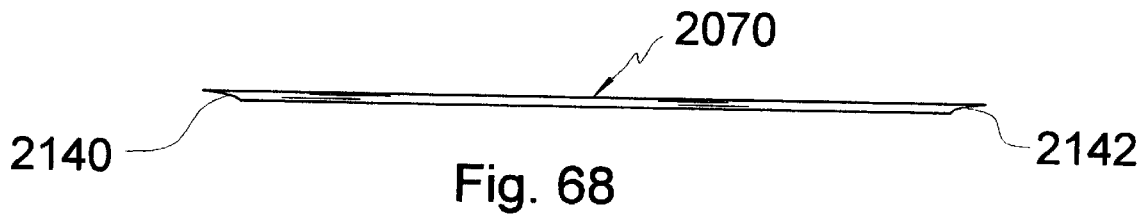
FIG. 68 is a perspective of a double ended needle of the type generally used in medical phlebotomy procedures and seen in FIG. 64.

FIG. 66 is a perspective of front cover 2050. Cover 2050 comprises a closed proximal end 2102 which is affixed to a hollow cylindrical section 2104. Distal from section 2104, cover 2050 is split into a pair of elongated legs 2106 and 2108, each comprising blunt distal ends 2110 and 2112, respectively. Front cover 2050 is also preferably made from polypropylene, however, as in the case of back cover 2020, other structurally stable synthetic resinous materials may be used.

One embodiment of front hub 2040 is seen in FIGS. 67 and 67A–C. In oblique perspective in FIG. 67, the proximal end of hub 2040 is shown to comprise a superior arched slot 2114 and an inferior arched slot 2116 surrounding a front hub segment 2118. Segment 2118 joins slots 2114 and 2116 at a planar front face 2120. As best seen in a combination of FIGS. 64, 67, 67B and 67C, front hub segment 2188 is a hollow cylinder closed proximally by a slitted end 2122. End 2122 comprises an "X" cut 2124 which provides a closable pathway through which needle 2070 is retracted in safe containment. It is important to note that other types of closures or partial closures can be used to block reextension of needle 2070 through an end, such as end 2122. An example of another embodiment is disclosed in detail hereafter.

FIG. 67A shows an oblique perspective of hub 2040 rotated approximately 90° from the angle of hub 2040 seen in FIG. 67, making the distal or rearwardly disposed surface 2126 of hub 40 visible. From the rear, hub 2040 is seen to comprise a tube coupler 2128 in the form of a hollow raised cylinder for attaching tube 2072 to hub 2040. Preferably, coupler 2128 comprises an internally disposed surface 2130 which is substantially the same diameter as the external surface of tube 2072. Tube 2072 residing within surface 2130 is seen in FIGS. 64 and 67C. Also, material make-up of hub 2040 and tube 2072 should permit ready adhesion of tube 2072 to surface 2130. Other methods and configurations for connecting tube 2072 to hub 2040 are within the scope of this instant invention.

Extending distally from a distal end 2132 of coupler 2128 is a tab 2134, shown in FIG. 67B. The function and purpose of tab 2134 is fully disclosed hereafter. Medially and proximally disposed relative to surface 2126 is a cylindrical surface 2136 which comprises a thread pattern 2138 for connecting securely to a barrel. The connecting method is disclosed in detail hereafter. Hub 2040 is preferably made from medical grade polypropylene, although other materials may be used which are adhesible to tube 2072 and which have good structural integrity relative to needle puncture resistance.

Needle 2070 is preferably made from a medical grade stainless steel cannula with a percutaneous sharpened tip on a proximal end 2140 and a non-coring sharpened tip 2142 on a distal end 2082. Needle 2070 should comprise a diameter consistent with contemporary phlebotomy needle diameters and should have sufficient length to provide a desired insertion length (usually one to one and one-half inches (25 to 38 millimeters)) measured as the length extending proximally from a barrel and to provide a desired insertion length (about 0.4 inches (10 millimeters)) within the barrel for introduction into a vacuum sampling tube.

Figure 69:
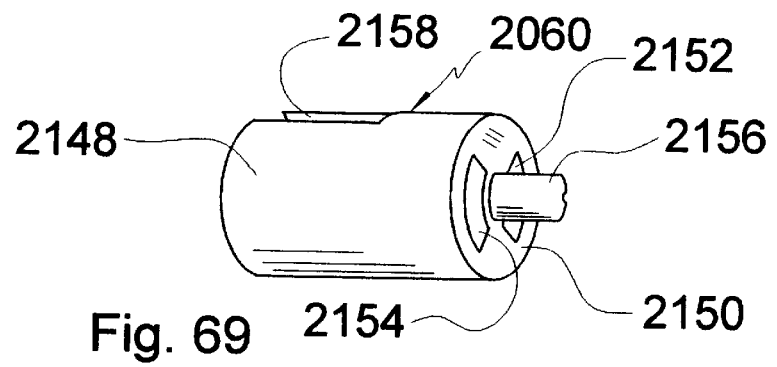
FIG. 69 is a perspective of a rearward needle hub seen in cross section in FIG. 64.

An oblique perspective of rear hub 2060 is seen in FIG. 69. As seen in FIG. 69, hub 2060 comprises an essentially hollow cylindrical body 2148 partially closed on one end by a planar surface 2150. Surface 2150 comprises a pair of arcuate slots 2152 and 2154 through which portions of sheath 2090 pass to permit compression of snubber 2080 and access to end 2082 and sharpened tip 2142. Distally, hub 2060 also comprises a centrally disposed needle hub 2156 extended axially outward to support needle 2070.

Figure 72:
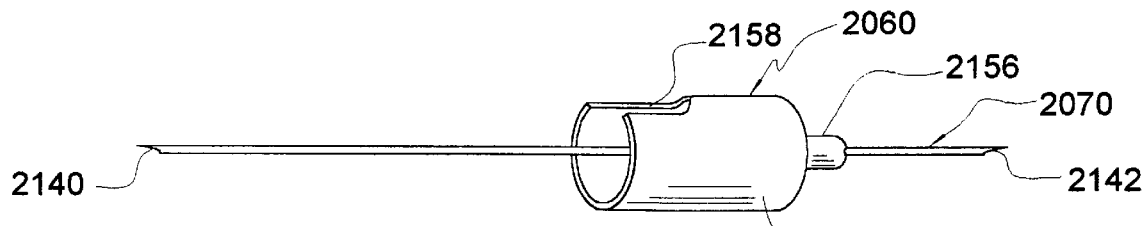
FIG. 72 is a frontal perspective of a combination comprising the medical needle seen in FIG. 68 affixed to the rearward needle hub seen in FIG. 69.
Figure 72A:
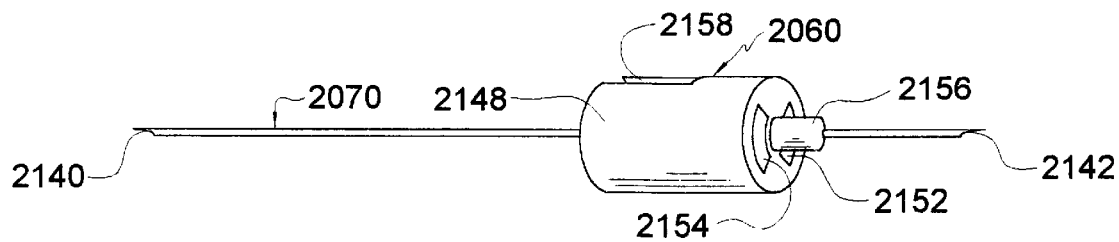
FIG. 72A is a rear perspective of the combination seen in FIG. 72.
Figure 72B:
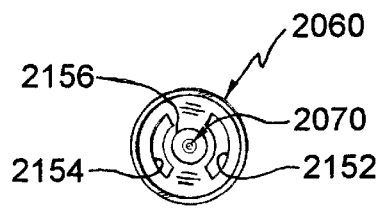
FIG. 72B is a rear elevation of the combination seen in FIG. 72.

A subassembly comprising needle 2070 and hub 2060 is seen in FIGS. 72 and 72A–72C. C. As seen in FIGS. 72 and 72A, cylindrical body 2148 comprises a proximally opening slot 2158. Slot 2158 is sized and positioned to receive tab 2134 when hubs 2040 and 2060 are aligned and disposed in contact one with the other. When tab 2134 is inserted into slot 2158, an axial lock is created which causes hubs 2040 and 2060 to rotate together when either hub is so moved. In an assembled device, needle 2070 is securely affixed to hub 2060, preferably by an adhesive.

Figure 72C:
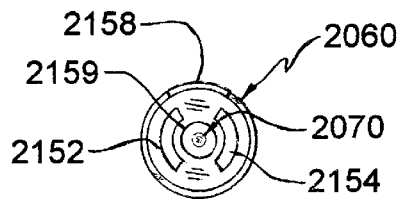
FIG. 72C is a rear elevation of the combination seen in FIG. 72.
Figure 73:
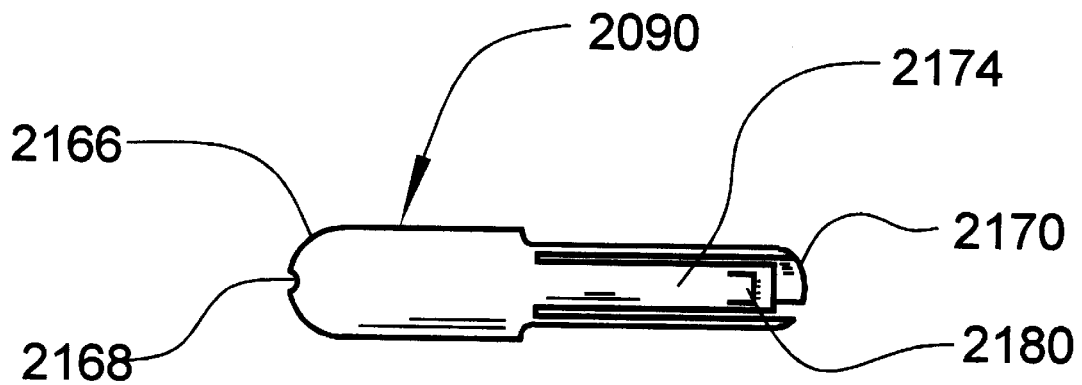
FIG. 73 is a frontal perspective of a shield which protects a rear portion of the medical needle seen in FIG. 68.
Figure 73A:
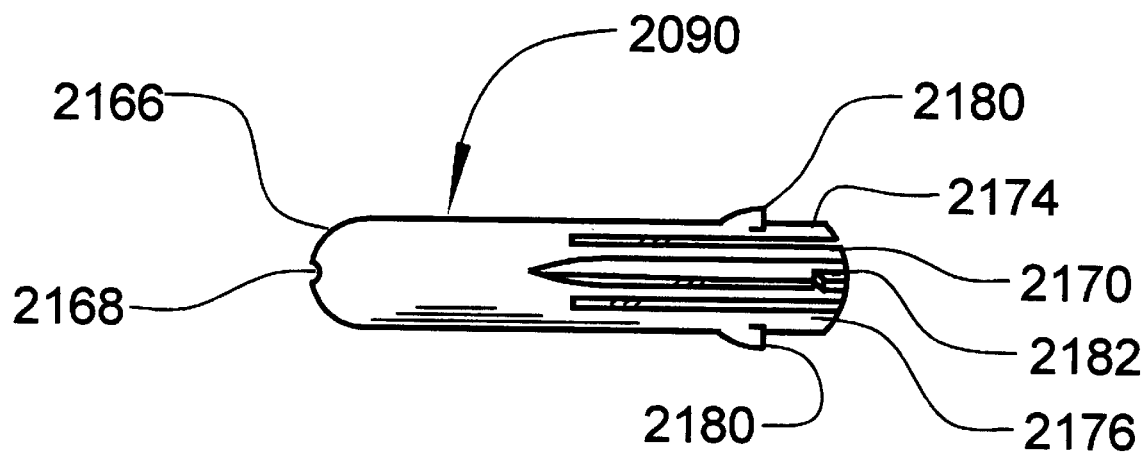
FIG. 73A is a rear perspective of the shield seen in FIG. 73.

As best seen in FIG. 72C, hub 2060 comprises a proximally centrally disposed small hub 2159 which provides a mount for the distally disposed end of tube 2072. Tube 2072 is securely affixed at one end to hub 2159 and at the other end to coupler 2128. Preferably, tube 2072 is so affixed by adhesives which are readily commercially available.

Figure 70:
FIG. 70 is a perspective of an elastic tube seen in FIG. 64.

Reference is now made to FIG. 70, wherein tube 2072 is seen. Tube 2072 is preferably a thin walled, relatively high durometer elastic tube. Though a rather large range of durometers may be used, the preferred range is between 35 and 50 durometer. Though other diameters may be used, the currently preferred diameter is 0.100 inches (2.54 millimeters). The length of tube 2072 should be sufficient to completely encase the portion of needle 2070 which extends proximally from hub 2060. Currently, preferred wall thickness of tube 2072 is 0.020 inches (0.51 millimeters). Tube 2072 may be made from Kraton, a product of Shell Corporation and available through Shell Chemical Company, 4225 Naperville Road, Suite 375, Lisle Ill. 60532-3660.

As tube 2072 is utilized both as an energy storing medium in retracting needle 2070 and as a length limiting structural member after needle 2070 is retracted, a non-elastic member 2160 is applied substantially to the entire length or enough of the length of tube 2072. Member 2160 impedes stretching of tube 2072, especially after needle 2070 retraction. By this means, when needle point 2140 is captured inside hub 2040 after retraction, tube 2072 cannot be further lengthened to permit access to point 2140, which may result in inadvertent injury. Member 2160 may be any foldable material which follows changes in tube 2072 contour as tube 2072 is compressed and which has sufficient tensile strength to retard stretching under manually applied stress. As an example, nylon thread may be used.

Figure 71:
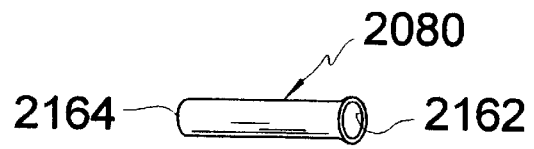
FIG. 71 is a perspective of a snubber of the type generally used in medical phlebotomy needle apparatus and seen in FIG. 64.

An oblique perspective of snubber 2080 is shown in FIG. 71. Snubber 2080 comprises a proximal open end 2162 and a distal end 2164. At end 2162, snubber 2080 is securely affixed to hub 2060 about smaller hub 2156. End 2164 is closed, but is sufficiently thin to permit penetration of tip 2142 therethrough. Generally, tip 2142 is ground to a non-coring configuration to limit sample contamination which might otherwise result from passage of tip 2142 through end 2164. Generally, such snubbers are currently available in the art of vacuum based blood draw systems. It is important that snubber 2080 be made from an elastic material having a durometer which provides sufficient memory upon deformation to substantially recover its original shape after a blood collection tube is removed after having collapsed snubber 2080. As is the case with tube 2072, the preferred durometer range for snubber 2080 is 35 to 50, although other values of durometer can be used.

Sheath 2090 provides an immovable protective cover over snubber 2080 before and after drawing a sample. During the process of drawing a sample, sheath 2090 must freely move to provide access for an interface between needle 2070 and a sample collection tube. Sheath 2090 comprises an elongated hollow cylindrical shape closed on a distal end 2166 except for an orifice 2168 through which tip 2142 traverses to interface with the sample collection tube. At a proximal end, sheath 2090 comprises a blunt end 2170 and a pair of leg parts 2174 and 2176. Leg parts 2174 and 2176 each comprise a stop 2180. Leg part 2176 also comprises a latch 2182. The purpose and function of leg parts 2174 and 2176 and associated stops 2180 are fully disclosed hereafter. Catch 2182 is designed to be forcibly inserted into a slot, such as slot 2152 in hub 2060, to securely, but slidably, affix sheath 2090 to hub 2060. Thereafter, sheath 2090 is prevented from separation from hub 2060 without breaking either sheath 2090 or hub 2060. Such connections of injection molded parts are well known in plastics art. Sheath 2090 is preferably made from polypropylene, although other structurally strong, but pliable materials may be used.

Reference is made to FIG. 74 for disclosure of a preferred assembly 2010 construction sequence. Though not necessary within the scope of the invention, it is recommended that assembly 2010 be put together in the following sequence:

1. Affix tube 2072 to hub 2040 at coupler 2128.
2. Affix tube 2072 to hub 2060 at hub 2159.
3. Insert tip 2142 of needle 2070 through "X" cut 2124 in proximal hub segment 2118 of hub 2040.
4. Cautiously thread needle 2070 through tube 2072 and hub 2060, taking care to safeguard needle tip 2142 from inadvertent contact with portions of either tube 2072 or hub 2060. Caution: Do not permit tip 2140 to pass through "X" cut 2124, as such could impair percutaneous performance of needle 2070 and would likely result in rendering assembly 2010 useless.
5. Securely affix needle 2070 to hub 2060 while maintaining position of needle tip 2140 proximal to "X" cut 2124.
6. Insert leg parts of cover 2050 through slots 2114 and 2116 until disposed relative to hub 2060 as seen in FIG. 64. Apparatus and method for interlocking cover 2050 with hub 2060 to maintain needle point 2140 proximal to hub 2040 is disclosed hereafter.
7. Affix snubber 2080 to hub 2060.
8. Affix sheath 2090 about snubber 2080 to hub 2060.
9. Distally dispose back cover 2020 over the distally disposed parts of assembly 2010 as seen in FIG. 64.
10. Affix a seal 2030 (preferably paper) about interfacing parts of hub 2040 and cover 2020 also as seen in FIG. 64.
11. To preserve intrapackage sterility, it is preferable that a fit between hub segment 2118 and the proximal portion of cover 2050 be sufficiently tight to provide a sterile barrier and hub segment 2118 and cover 2050 be heat staked to assure maintenance of sterility prior to use.

Thus assembly 2010 is complete and ready for transport to a site of use.

Figure 75:
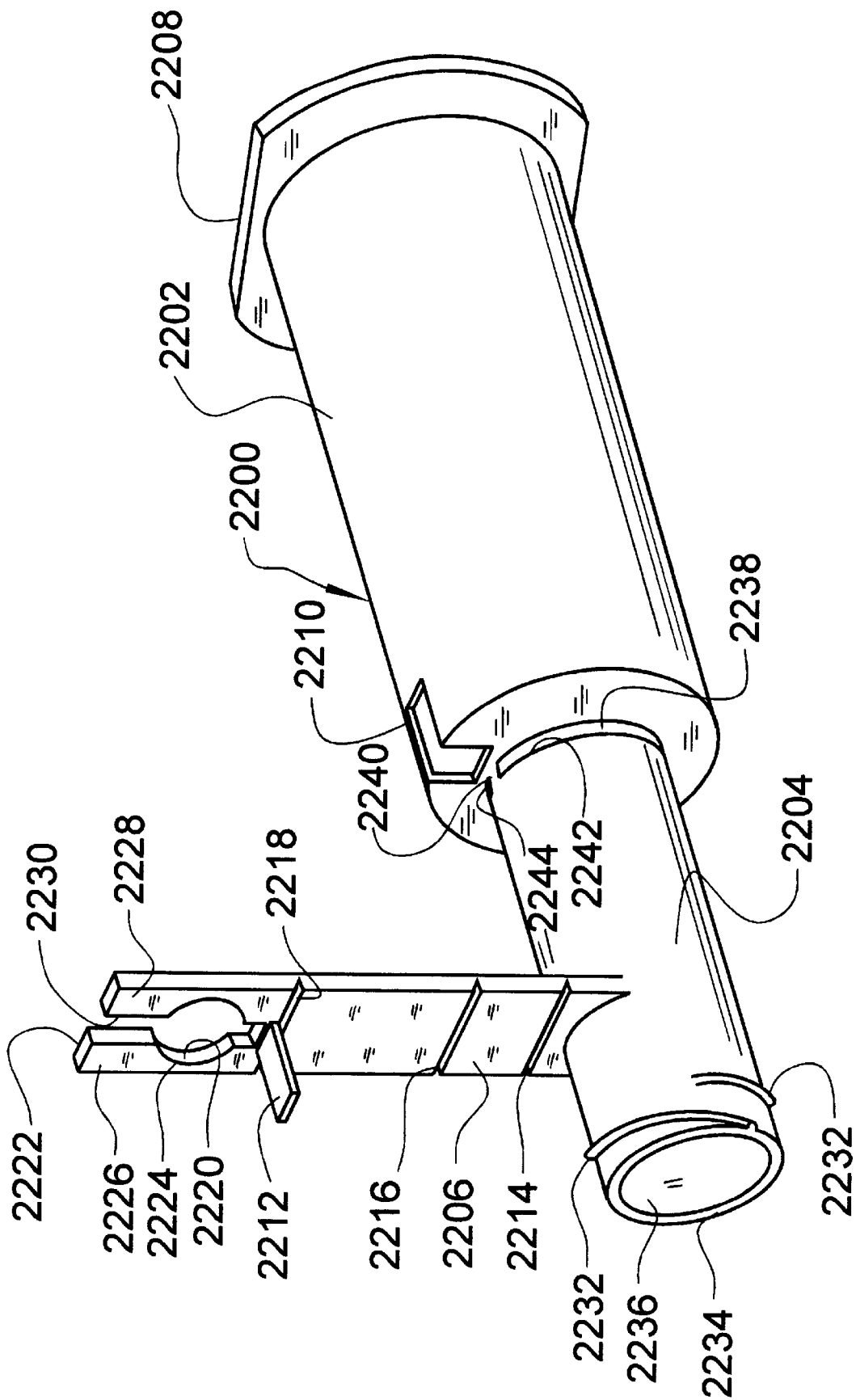
FIG. 75 is a molded perspective of a phlebotomy barrel used with the medical phlebotomy needle apparatus.
Figure 76:
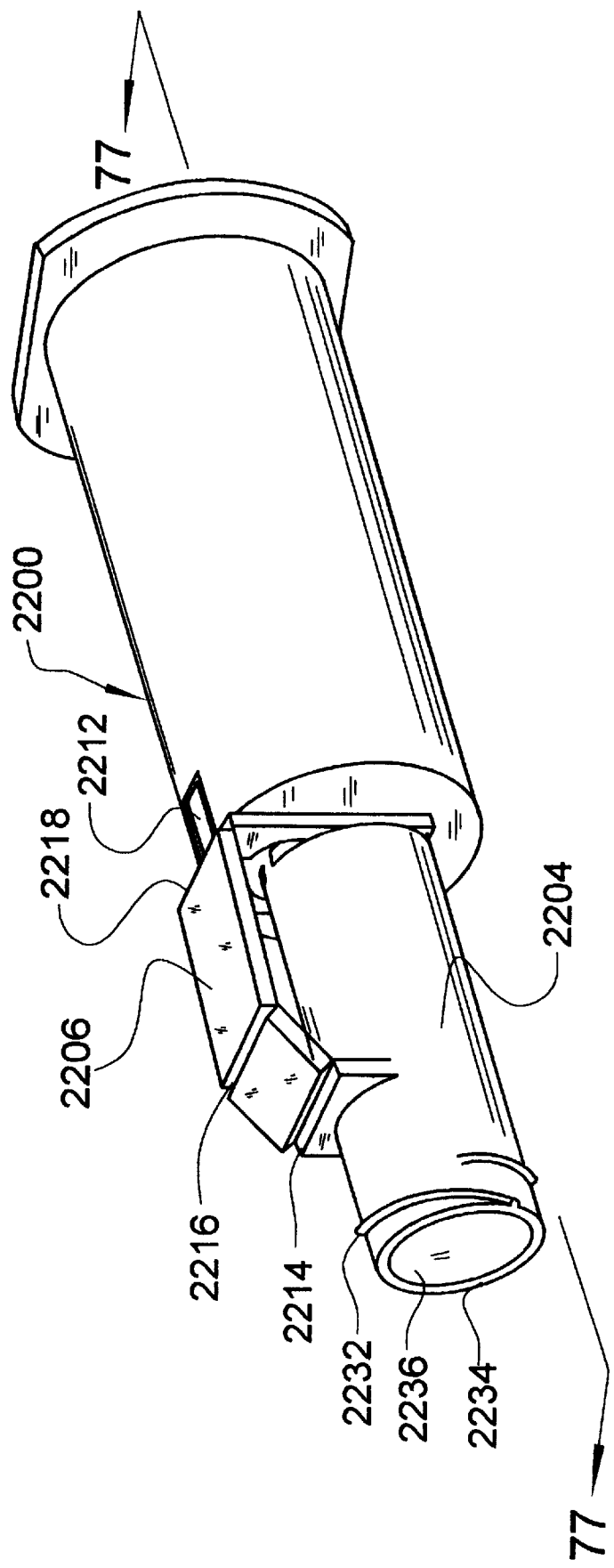
FIG. 76 is a perspective of the phlebotomy barrel seen in FIG. 75 with a portion of the barrel folded into position for use.
Figure 77:
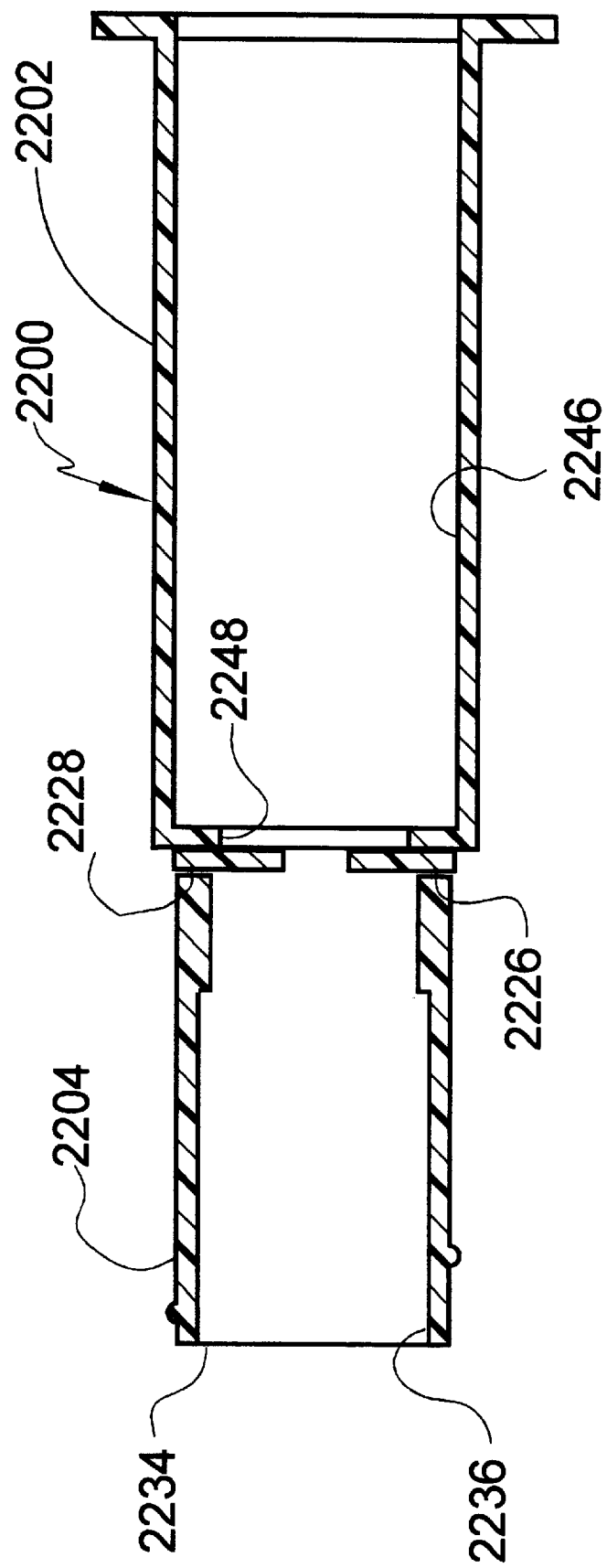
FIG. 77 is a cross section taken along lines 77—77 in FIG. 76.

In blood sampling procedures, assembly 2010 is used with a barrel 2200, seen in FIGS. 75–77. Barrel 2200 is preferably made as a single injection molded part. Barrel 2200 may be made from polypropylene.

As seen in FIG. 75, barrel 2200 comprises a barrel part 2202, an elongated neck segment 2204 and an extended latch and trigger strip 2206. Barrel 2200 is similar in form and function to barrels used with Vacutainers® blood collection tubes (blood sampling tubes from Becton, Dickinson and Company of Franklin Lakes, N.J.). Barrel 2200 further comprises a distal sampling tube access end 2208 and a slot 2210 used in combination with a tab 2212, which is an integral part of strip 2206 to detect the presence of a sampling tube in part 2202 and thereby impede triggering retraction of needle 2070, as is more completely disclosed hereafter. Slot 2210 and tab 2212 are optional as such an impedance is not specifically required within the scope of the invention.

Strip 206 may be molded as seen in FIG. 75 or in other modes as determined by molding constraints. Strip 2206 may also be molded as a separate part and attached during barrel 2200 assembly; however, it is presently preferred to mold barrel 2200 in total as a unit. Strip 2206 comprises a plurality of living hinges (of which hinges 2214, 2216 and 2218 are examples). Strip 2206 also comprises an opening 2220 (seen as an upside down keyhole in FIG. 75) inferiorly disposed to a superiorly blunt extremity 2222. Opening 2220 comprises a substantially circular portion 2224 which is of sufficient diameter to pass rear hub 2060 and tube 2072. Superior to opening 2220, strip 2206 comprises a pair of legs 2226 and 2228 to define a rectangular opening 2230 through which hub 2060 cannot pass.

Segment 2204 comprises a proximally disposed thread 2232, which is used in combination with thread pattern 2138 to form a secure, but releasable connection between segment 2204 and hub 2040. Segment 2204 also comprises a proximal orifice 2234 which provides access to an elongated cylindrical internal surface 2236. Further, segment 2204 is integrally connected to barrel part 2202 at an interface 2238 by a pair of indicated by bridges 2240. (A lower bridge 2240 is not shown in FIG. 75.) Juxtaposed bridges 2240 are a pair of slots 2242 and 2244, each slot having a width adequate for passage of a portion of strip 2206.

As a final step in assembly of barrel 2200, hinges 2214, 2216 and 2218 of strip 2206 are folded and extremity 2222 and legs 2226 and 2228 are inserted into respective slots 2244 and 2242. As seen in FIG. 76, strip 2206, as folded and inserted into slots 2242 and 2244, is spring biased such that circular portion 2224, which can pass hub 2060, is superiorly disposed to a passageway defined by cylindrical surface 2236.

Reference is made to FIG. 77 where, in cross section, blocking of the passageway between cylindrical surface 2236 and an internal cavity 2246 of barrel part 2202 is accomplished by legs 2226 and 2228. Barrel part 2202 comprises an access orifice 2248 distal to a plane defined by legs 2226 and 2228.

Figure 78:
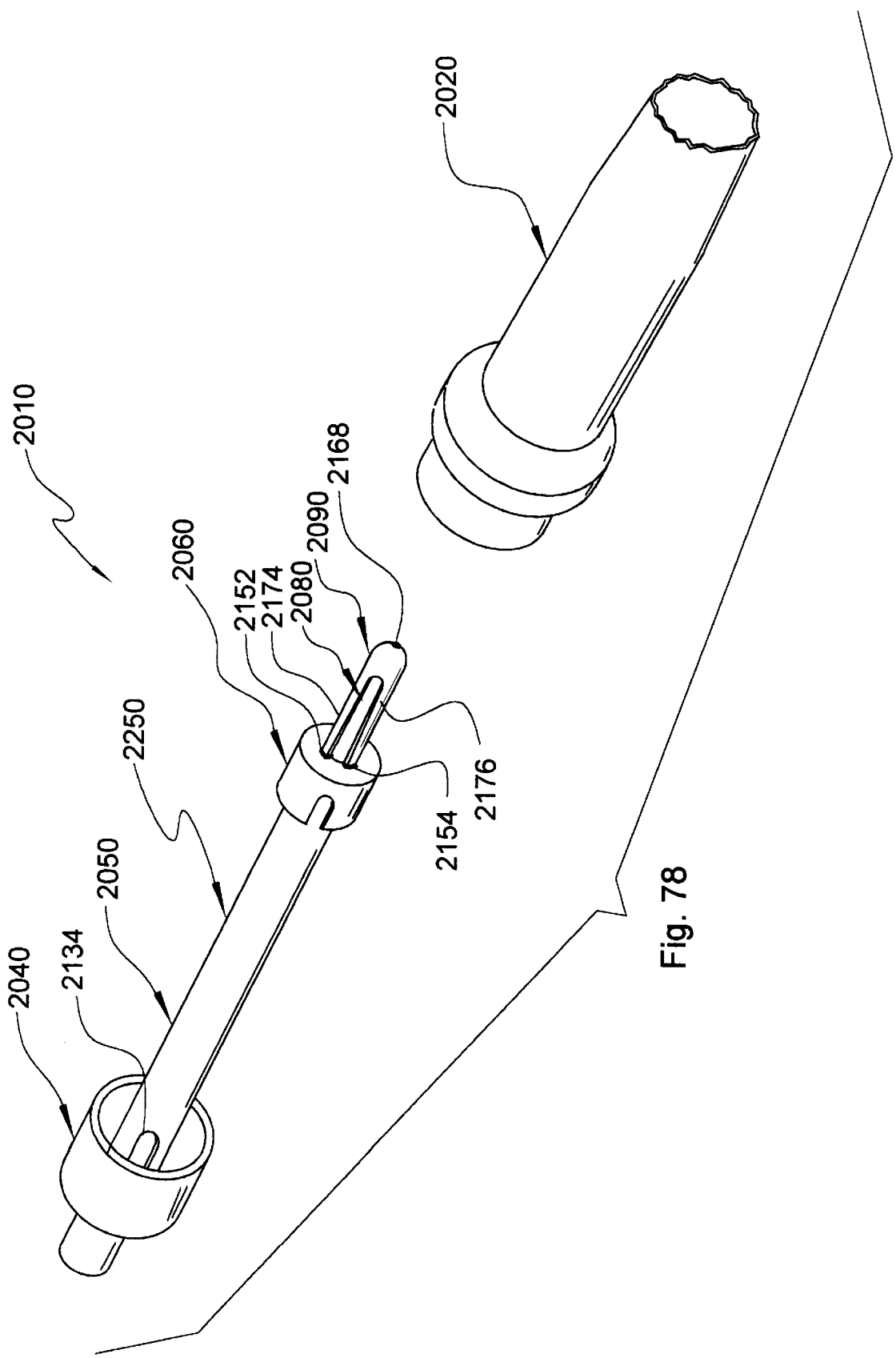
FIG. 78 is a perspective of the apparatus of FIG. 63 with the back cap seen in FIG. 65 removed to ready an insertable portion of the safety needle apparatus for insertion into a barrel for subsequent use.
Figure 79:
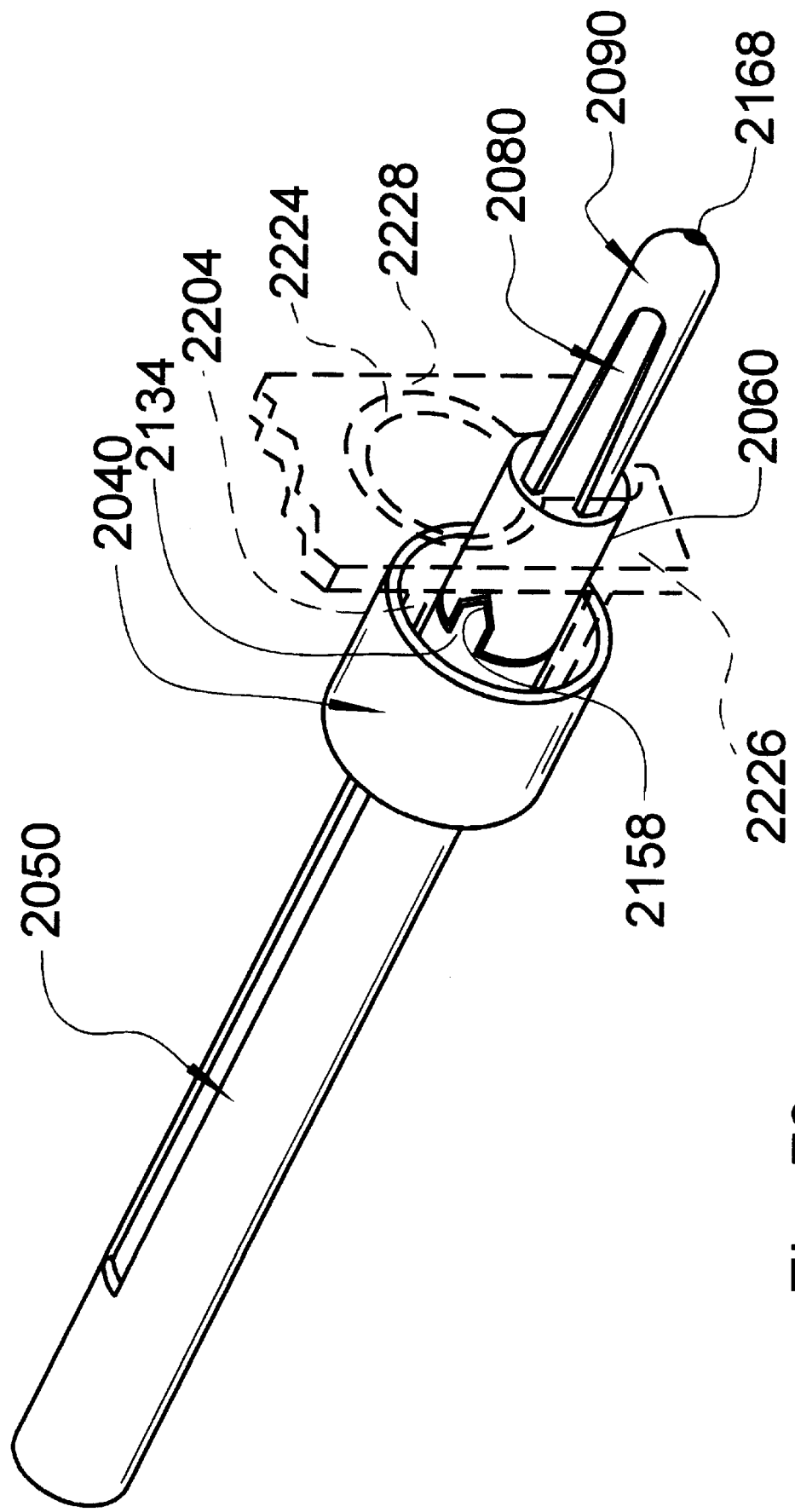
FIG. 79 is a perspective of the insertable portion of the safety needle apparatus in a state after insertion into the barrel.

To prepare assembly 2010 for use with barrel 2200, rear cover 2020 is removed from a remaining portion 2250 of assembly 2010, as seen in FIG. 78, after breaking seal 2030 which is not shown for clarity of presentation. Next portion 2250 is inserted through orifice 2234 into barrel segment 2204, sheath 2090 being inserted first. As illustrated in FIG. 79, legs 2226 and 2228 (shown by dashed lines) block further insertion causing hub 2040 to be pushed into contact with hub 2060 and tab 2134 to be engaged in slot 2158. This engagement is important for a number of reasons, but primary among them is to assure that the angular disposition of hub 2060 relative to hub 2040 is controlled and known. It is considered critical by most medical technicians that needle tip 2140 be in a predetermined orientation for use.

Figure 80:
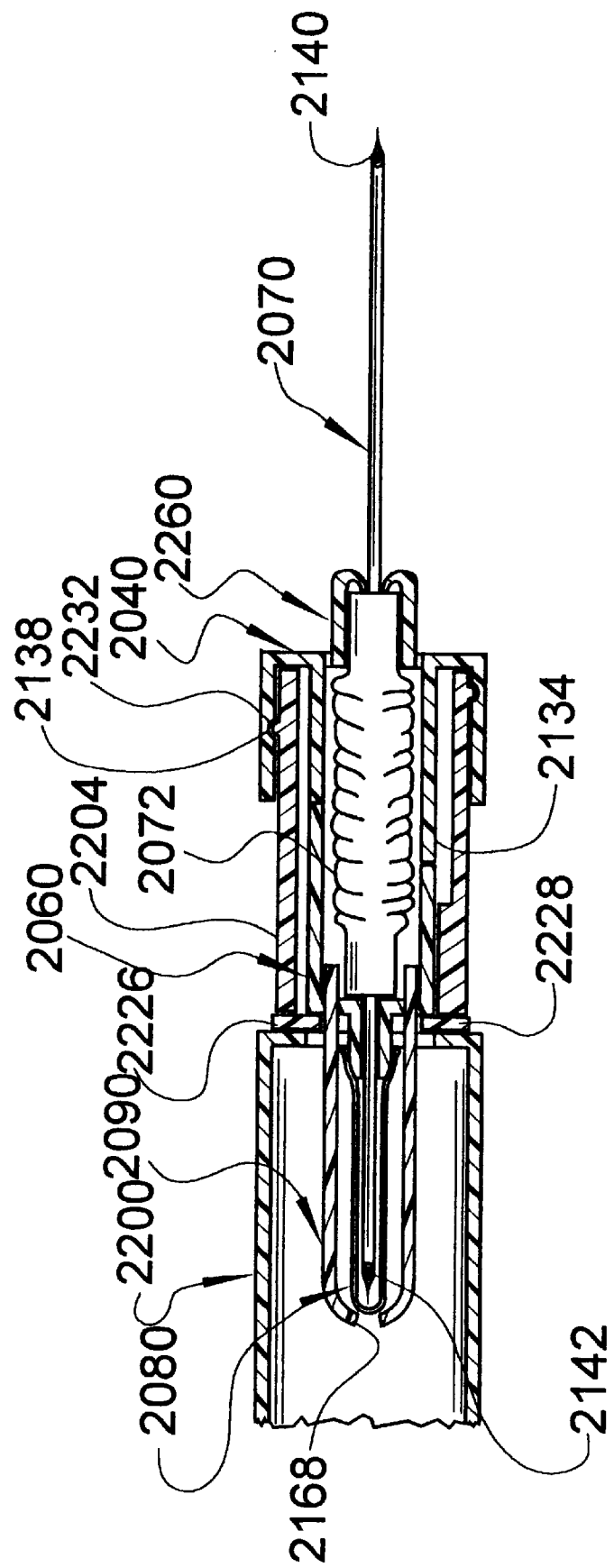
FIG. 80 is cross section of safety needle apparatus disposed in the barrel.

Pushing hub 2040 into contact with hub 2060 results in compression of tube 2072 as is illustrated in FIG. 80. Hub 2040 is securely, but releasibly, affixed to barrel segment 2204 by threaded members 2138 and 2232. Since it is important that the axial orientation of needle tip 2140 be known and controlled, care must be taken to assure proper orientation of hub 2040 relative to barrel 2200 when hub 2040 is finally affixed to segment 2204. For this reason, bayonet or slide-in catching joints may be preferred to connect hub 2040 to segment 2204.

When hub 2060 is pressed hard against legs 2226 and 2228, stops 2180 are depressed inward by legs 2226 and 2228 permitting leg parts 2174 and 2176 of sheath 2090 to slide freely through slots 2152 and 2154, respectively, of hub 2060. In this manner, sheath 2090 is freely displaced by a sample collection tube and needle tip 2142 finds passage through orifice 2168, while sheath 2090 is engaged between legs 2226 and 2228. However, sheath 2090 is locked in place providing safe protection for needle tip 2142 when the sheath is not so engaged.

Figure 81:
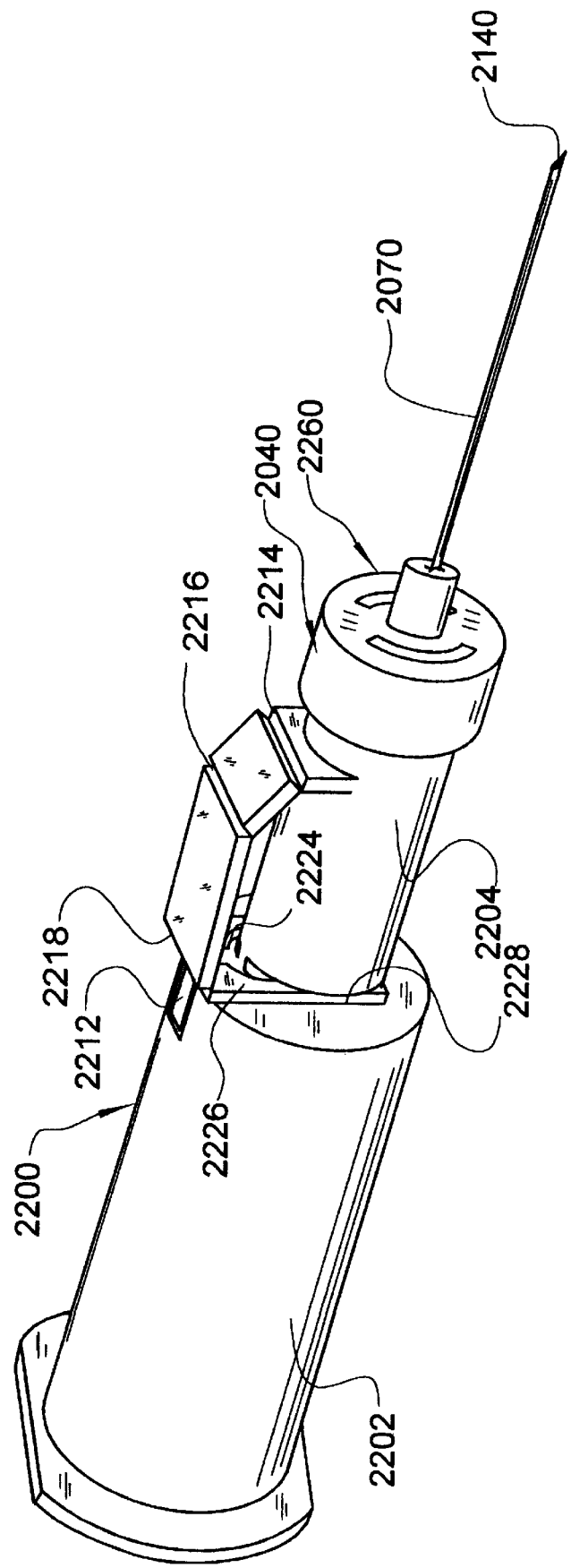
FIG. 81 is a perspective of safety needle apparatus disposed in the barrel with the phlebotomy needle bared and ready for use.

After connecting hub 2040 to segment 2204, cover 2050 is removed to bare needle tip 2140 as seen in FIG. 80. With cover 2050 removed from portion 2250, a residual disposable 2260 is mounted securely, but releasibly affixed to barrel 2200. A perspective of barrel 2200 with disposable 2260 affixed with needle tip 2140 bared is seen in FIG. 81.

Figure 82:
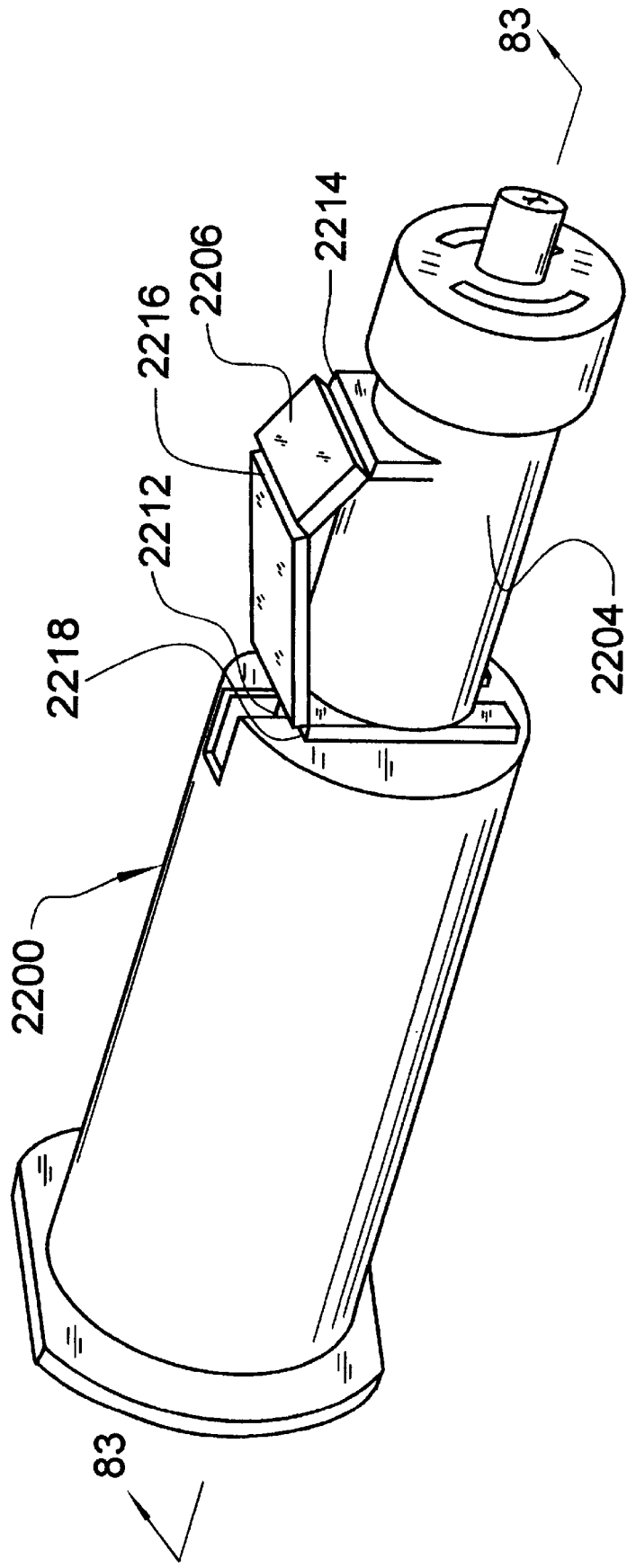
FIG. 82 is a perspective of the barrel and safety needle apparatus after the needle has been retracted into safe containment within the barrel.
Figure 83:
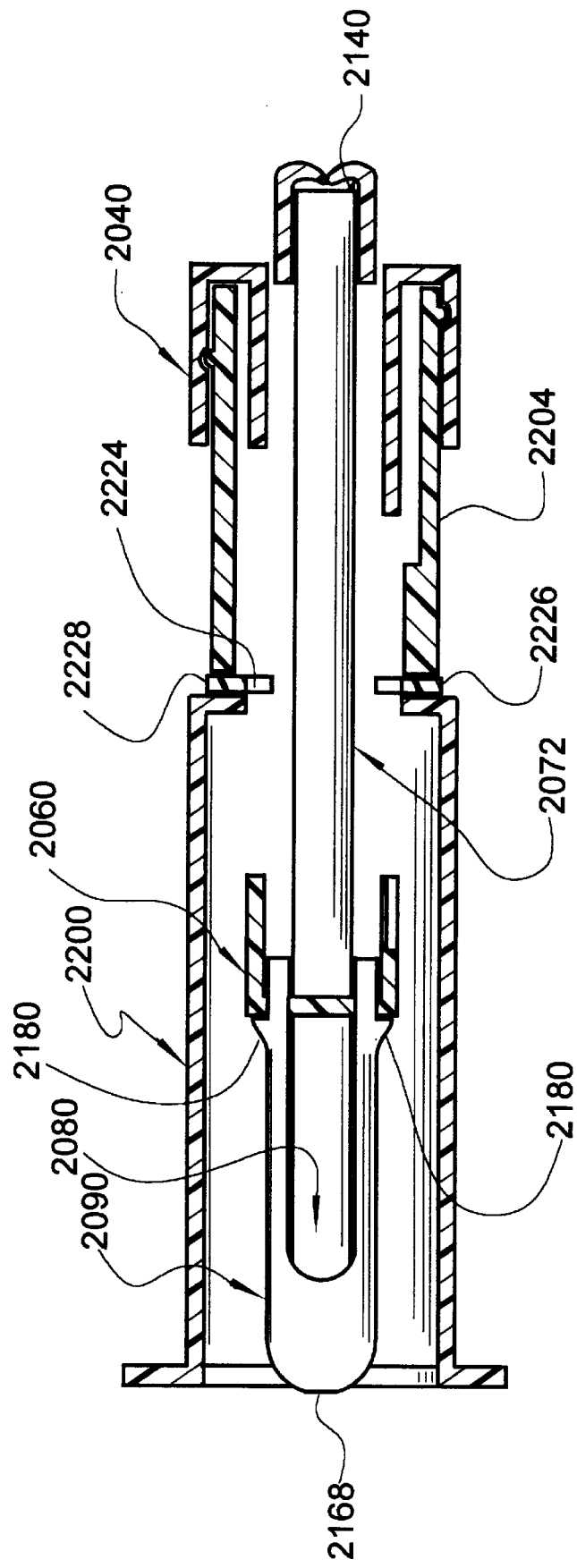
FIG. 83 is a cross section taken along lines 83—83 of FIG. 82.

At the end of a medical procedure, a portion of strip 2206 is depressed to align circular portion 2224 with hub 2060, thereby releasing hub 2060 from containment by legs 2226 and 2228. Resultingly, the energy stored in compressed tube 2072 causes hub 2060 and associated parts of disposable 2260 to be displaced distally into barrel 2200. When hub 2060 is so displaced, needle tip 2140 is retracted into safe containment within the confines of hub 2040. This state of disposable 2260 is best seen in FIGS. 82 and 83. Stops 2180 are engaged against hub 2060 to prevent proximal travel of sheath 2090 and thereby protecting needle tip 2142 from exposure through orifice 2168. Tube 2072 acts to fully cover and enclose a proximal portion of needle 2070 and needle tip 2142. Needle tip 2142 also is captured within hub 2040. Disposable 2260 is converted to a relatively rigid structure by engagement of stops 2180 and needle 2070 being trapped inside hub 2040. The integrity of disposable 2260 is further enhanced by the non-elasticity of member 2160 which restricts further lengthening of tube 2072.

Figure 84:
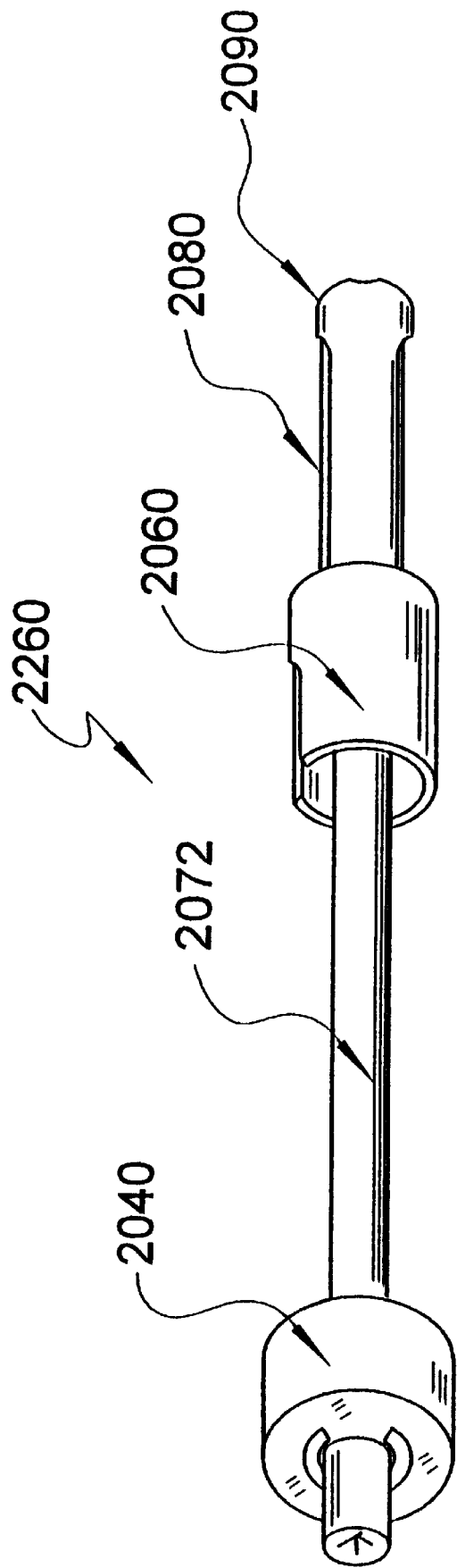
FIG. 84 is a perspective of the safety needle apparatus with both ends of the needle contained and protected for safe disposal.

As hinges 2214, 2216 and 2218 may spring load strip 2206 to return to a pre-trigger state after retraction of needle 2070, it is necessary to depress strip 2206 one more time to remove disposable 2260 from barrel 2200. Disposable 2260 is removed from barrel 2200 by unscrewing hub 2040 (when a screw attachment is used) from segment 2204, depressing strip 2206, if necessary, and pulling disposable 2260 proximally through orifice 2234. The form of disposable 2260, removed from barrel 2200, is seen in FIG. 84. Both needle points are protectively and securely covered for safe disposal.

An example of an alternate embodiment of a back hub 2060' comprising another method of impeding free movement of sheath 2090, when tube 2072 is not compressed (and needle 2070 is not disposed for use in a medical procedure), is illustrated in FIGS. 85 and 86. Hub 2060 and 2060' are substantially the same in form and function with the exception that hub 2060' comprises an inwardly displaced tab 2270, which is hingeably connected to a distal portion 2272 of hub 2060'. A proximal end 2274 of tab 2270 is biased to be medially disposed against tube 2072 when tube 2072 is not compressed such that, when tube 2072 is compressed as disclosed above, proximal end 2274 is displaced outwardly, away from needle 2070. While so displaced, proximal end 2274 is engaged against hub 2040 and captured thereat.

Tab 2270 comprises an interior side 2276 and a catch 2278 disposed thereon. This catch is disposed to act against proximal end edge 2170 and to stop sheath 2090 from traveling proximally. Only when tube 2072 is compressed and end 2274 is engaged against hub 2040, is sheath 2090 free to travel proximally. This is the condition when medical needle 2070 is disposed for use and when a sampling tube is disposed for use in barrel 2200.

Reference is now made to FIGS. 87 and 88 where an alternate hub form 2040' of hub 2040 is shown. Hub form 2040' is similar in form and function to hub 2040, except that when using hub 2040, needle tip 2140 is needfully constrained from distally passing through any front barrier of hub 2040 by a connection between cover 2050 and hub 2060 and another connection between cover 2050 and hub 2040. These two constraints permit tube 2072 to be compressed slightly until both connections are broken as a result of inserting assembly 2010 portion 2250 into barrel 2200, thereby biasing needle tip 2140 proximally and keeping tip 2140 from retracting into hub 2040. To eliminate the need for so slightly compressing tube 2072, hub 2040' comprises a proximal face 2280, which has two stable positions. A first position comprising a proximally concave state of face 2280 as seen in FIG. 87. A second position comprising a proximally convex state of face 2280 as seen in FIG. 88. When not attached to barrel 2200, convex face 2280 is distally depressed toward hub 2060, thereby shortening the effective distance between face 2280 and hub 2060 and causing needle tip 2140 to be proximally disposed relative to face 2280.

When hub 2040' is connected to segment 2204 as earlier disclosed for connecting hub 2040 to segment 2204, face 2280 is forced into the convex state. The change of state does not occur until hub 2040' is moved into contact with segment 2204 and, therefore, needle tip 2140 is already extended proximally well beyond face 2280. However, when needle 2070 is retracted into barrel 2200, such as through orifice 2282, the needle tip is captured within hub 2040' as seen in FIG. 88. Use of hub 2040' eliminates any need for even slightly compressing tube 2072 prior to insertion of portion 2250 into barrel 2200.

Entrapment of needle tip 2140 may be accomplished by many different ways within the scope of the invention. As examples, by retracting needle tip 2140 through a self closing element (such as the previously disclosed "X" cut 2124) or by creating a curved resting tube 2072 through a shortening bias by non-elastic member 2160 or by an internal component housed within segment 2204 which biases needle 2070 and, therefore, needle tip 2140 toward an inside wall of hub 2040. One mechanism for positively impeding the escape of needle tip 2140 from a front hub (such as hub 2040), after needle 2070 retraction, is by interposing a part between needle tip 2140 and an exit orifice 2290 as seen in FIG. 90. A front hub 2040'', which is similar in form and function to hub 2040, except for replacing "X" cut 2124 with a selectively plugging element, such as element 2292, is seen in FIGS. 89 and 90. In this case, element 2292 is formed by franging most of an initial portion of a plug molded into hub 2040'' covering a hole space which is to be opened to provide the needle 2070 access of orifice 2290. As best seen in FIG. 89, sufficient material is left after the frange to permit element 2292 to remain hingeably affixed to hub 2040'' at orifice 2290 and to remain biased against needle 2070 as long as a portion of needle 2070 is disposed proximal to orifice 2290. However, after needle 2070 retraction, element 2292 responds to inherent prefrange memory to hingeable displacement to at least partially plug orifice 2290 and impede further proximal travel of needle 2070, such that needle tip 2140 is safely retained distal to orifice 2290.

Another Catheter Embodiment

Attention is now directed to FIGS. 91–96 wherein an embodiment of an extendable and retractable IV catheter device is seen. The IV catheter device derives energy for retraction by a vacuum pulled as a catheter needle is extended for use. This embodiment comprises a quick release cover which is used to extend the needle and for a cantilevered trigger release button which is activated to retract the catheter needle.

Figure 91:
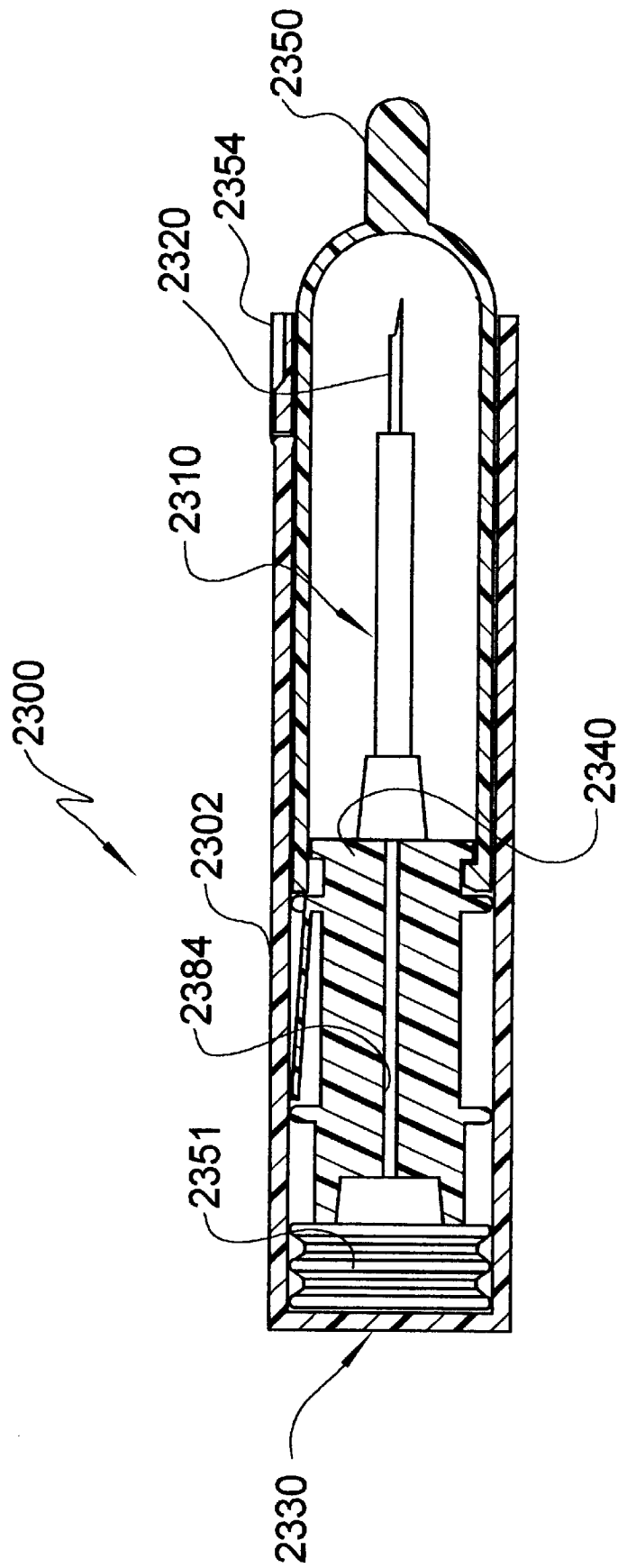
FIG. 91 is a cross section of an extendable medical catheter apparatus.

As seen in FIG. 91, a catheter device 2300 requires but four injection molded parts. The parts comprise an elongated barrel 2302 from which a catheter 2310 and catheter needle 2320 are extended for us and into which the catheter needle 2320 is retracted for safe disposal, a back disk 2330 which closes a rear portion of barrel 2302 such that a vacuum can be created therein when a plunger traverses barrel 2302, a releasible latch and needle hub 2340, and a cover 2350 which is used to extend catheter 2310 and needle 2320 from barrel 2302 preparatory to using catheter device 2300. Device 2300 also comprises a plunger 2351, which is similar to a plunger for a disposable syringe and which is securely affixed to needle hub 2340.

Figure 92:
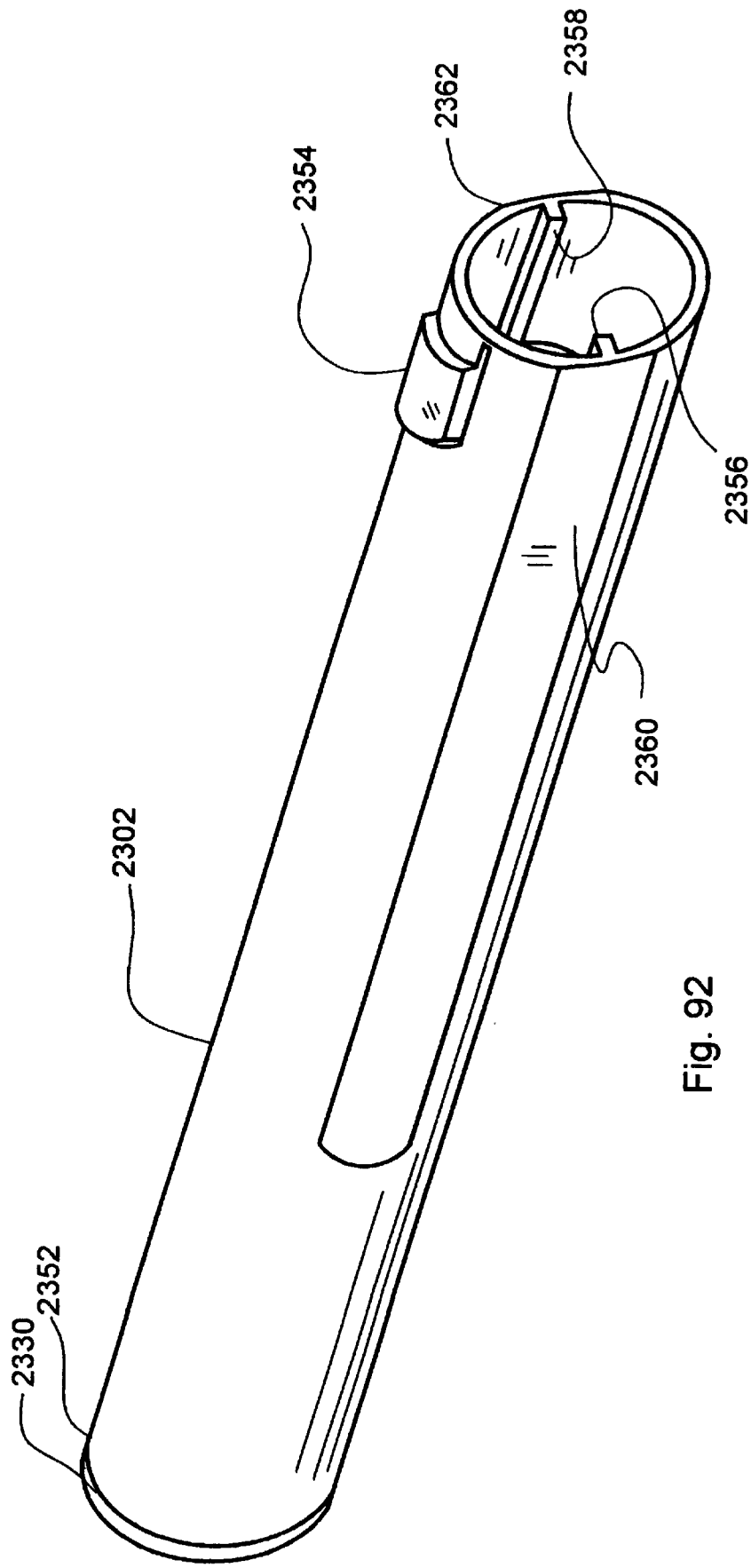
FIG. 92 is a perspective of an elongated cylinder which forms a rearward portion of the catheter apparatus of FIG. 91.

Barrel 2302, closed at a distal end 2352 by disk 2330, is seen in FIG. 92. Both barrel 2302 and disk 2330 may be made from polycarbonate, although other materials may also be used, which have sufficient structural integrity to combine with plunger 2351 to produce a vacuum within barrel 2302, as the plunger is pulled within the barrel 2302, and to withstand ambient forces associated with the vacuum. Disk 2330 is preferably adhesively affixed to barrel 2302. Adhesives for such purposes are well known in the art. Also, as seen in FIG. 92, barrel 2302 comprises a cantilevered trigger release button 2354, the purpose and function of which is disclosed hereafter. Button 2354 is molded as an integral part of barrel 2302. Barrel 2302 also comprises various rails 2356 and 2358 and side indentations 2360 and 2362, which support reliable operation of device 2300.

Figure 93:
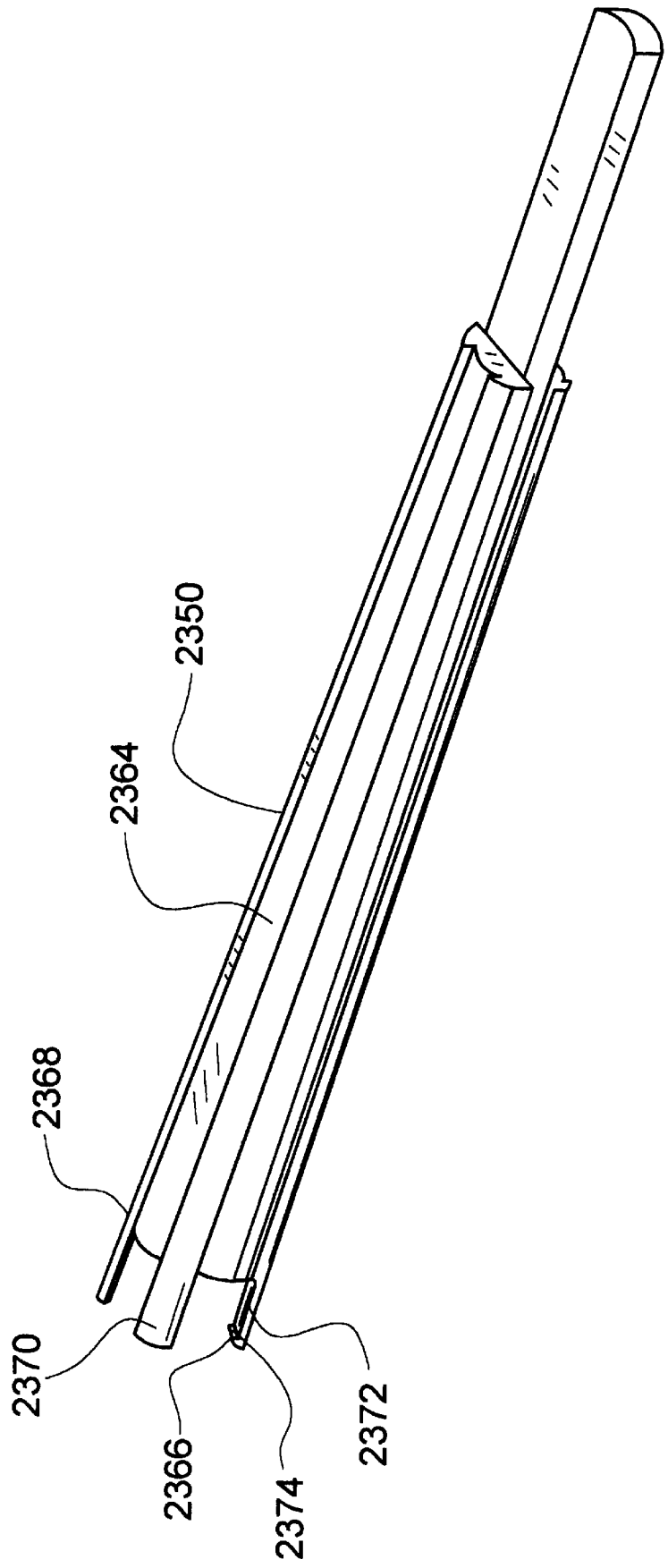
FIG. 93 is a perspective of a forwardly disposed needle cover of the extendable medical catheter apparatus of FIG. 91.

A perspective of cover 2350 is seen in FIG. 93. Cover 2350 comprises an elongated hollow cylinder 2364, which covers and protects prior to and during elongation of device 2300 preparatory for use. At a distal end 2366, cover 2350 comprises three legs, denoted as 2368, 2370 and 2372. Legs 2368 and 2370 are simple extensions which provide axial support until cover 2350 is removed after extension of device 2300. However, leg 2373 comprises a raised latch element 2374, the purpose and function of which is disclosed hereafter. Cover 2350 may be made from polypropylene.

Figure 94:
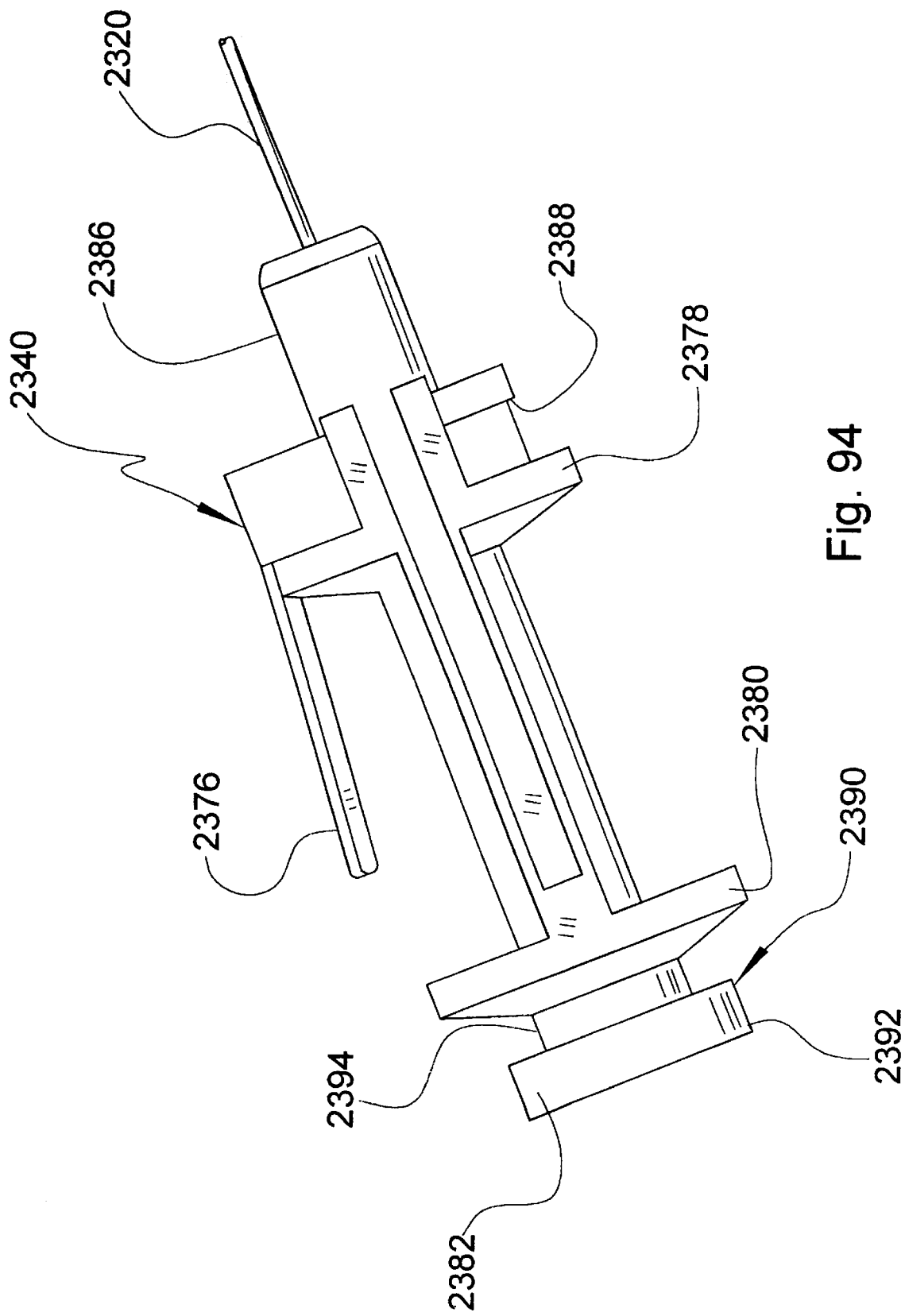
FIG. 94 is a perspective of a needle hub of the catheter apparatus seen in FIG. 91.

As seen in FIG. 94, hub 2340 comprises a latch part 2376, stabilizing disks 2378 and 2380 for lateral support of hub 2340 within barrel 2302 and a plunger attachment hub 2382. Also, hub 2340 comprises a cylindrical hole 2384 (see FIG. 91) sized to accept catheter needle 2320 and a proximal hub 2386 upon which IV catheter 2310 is releasibly connected for transport and prior to separation from hub 2386 after needle 2320 retraction. Disposed immediately distal and inferiorly of hub 2386 is an axially protruding catch 2388, the purpose and function of which is disclosed hereafter.

Hub 2382 also comprises a filter (not shown) which selectively passes gas, but which is impervious to liquids, and a pathway from needle 2320 to the filter. Such filters are available from Paras Corporation. Additionally, another pathway (also not shown) is provided from the filter to the atmosphere such that the air resident in needle 2320 at the beginning of a procedure escapes through the filter and fluid is thereby permitted to flow to the filter through needle 2320. Such fluid, when the catheter is placed into a patient's vessel, provides a red "flash" signaling needle 2320 entry into the vessel.

Hub 2382 comprises an outer surface contour 2390 comprising a raised plunger connecting part 2392 and a depressed plunger anchoring part 2394 for mooring plunger 2351. Such connecting parts are well known in the art of manufacturing disposable syringes.

Figure 95:
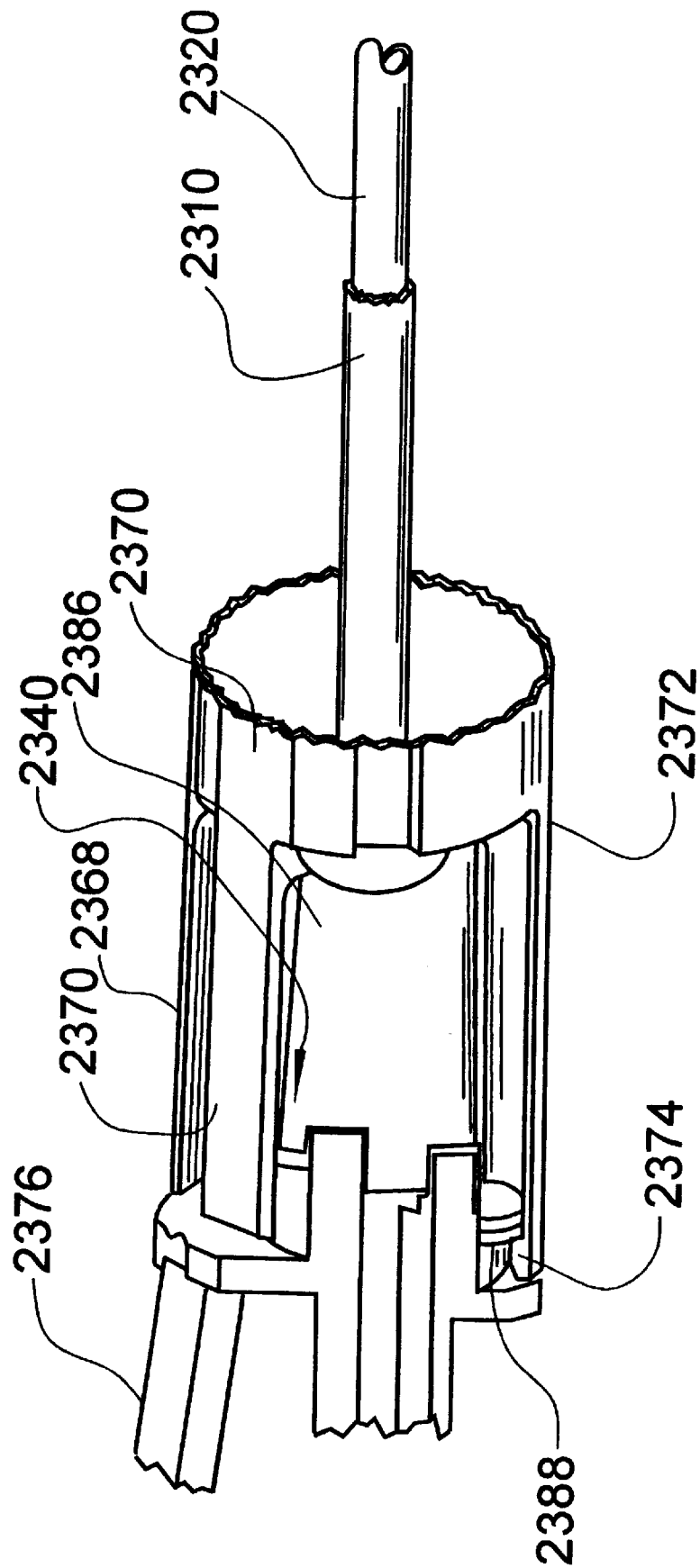
FIG. 95 is a perspective of a combination of sections of the cover of FIG. 93 and the hub of FIG. 94.

Reference is now made to FIG. 95 wherein an attachment is seen between hub 2340 and a portion of cover 2350. Legs 2368, 2370 and 2372 are engaged about hub 2386 and other portions of hub 2340. Latch element 2374 is selectively caught upon protruding catch 2388 which causes cover 2350 to be firmly affixed to hub 2340 as long as latch element 2374 and associated leg 2372 are confined within a catheter barrel 2302. However, after latch element 2374 is free of barrel 2302, rotation of cover 2350 frees latch element 2374 from catch 2388, permitting cover 2350 to be removed from hub 2340 and, therefore, from device 2300.

Figure 96:
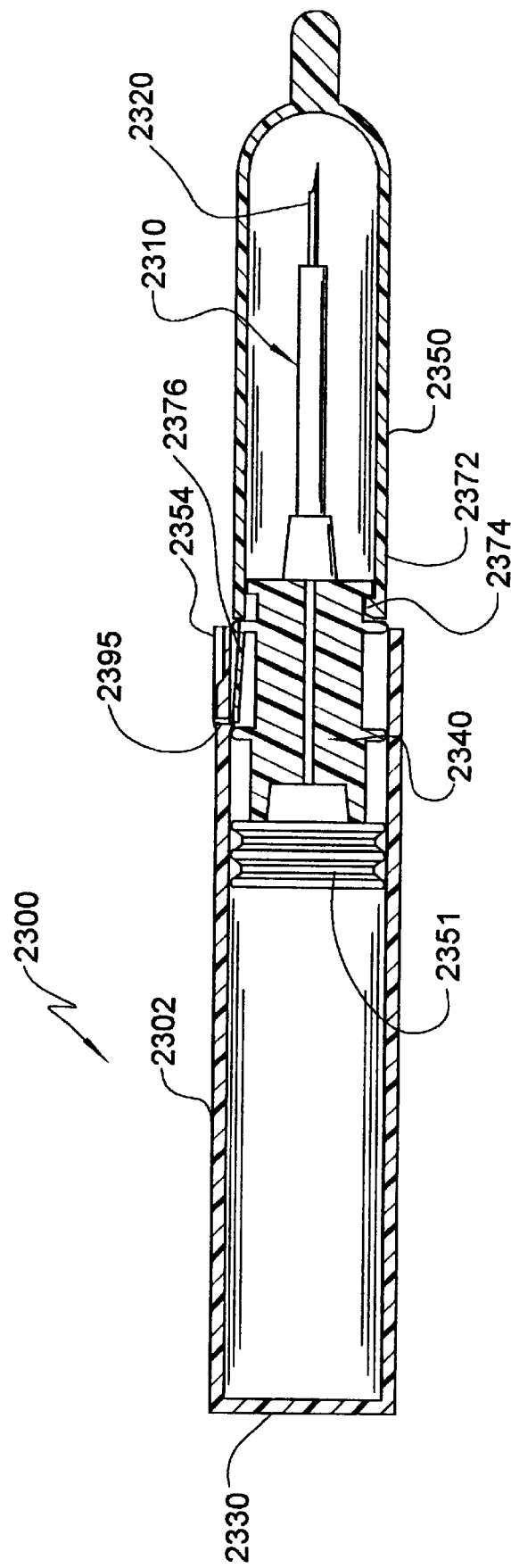
FIG. 96 is a cross section of the catheter apparatus of FIG. 91 comprising a needle, catheter and needle cover extended for use.

In FIG. 96, device 300 is shown with needle 320 and the catheter extended. As cover 2350 is used to pull hub 2340 outward from barrel 2302 to extend needle 2320 and catheter 2310 for use in a medical procedure, a vacuum is pulled within barrel 2302 by interaction of plunger 2351, barrel 2302 and barrel-end closing disk 2330. When needle 2320 and catheter 2310 are adequately extended and before cover 2350 is released latch 2376 is caught upon a catch 2395 disposed distal to button 2354. To retract needle 2320, cantilevered button 2354 is depressed against latch 2376 to free hub 2350. Energy stored by the vacuum then resident in the volume defined by barrel 2302, disk 2330 and plunger 2351 causes needle 2320 to be moved distally from enclosure by catheter 2310 and into safe containment of barrel 2302.

Figure 97:
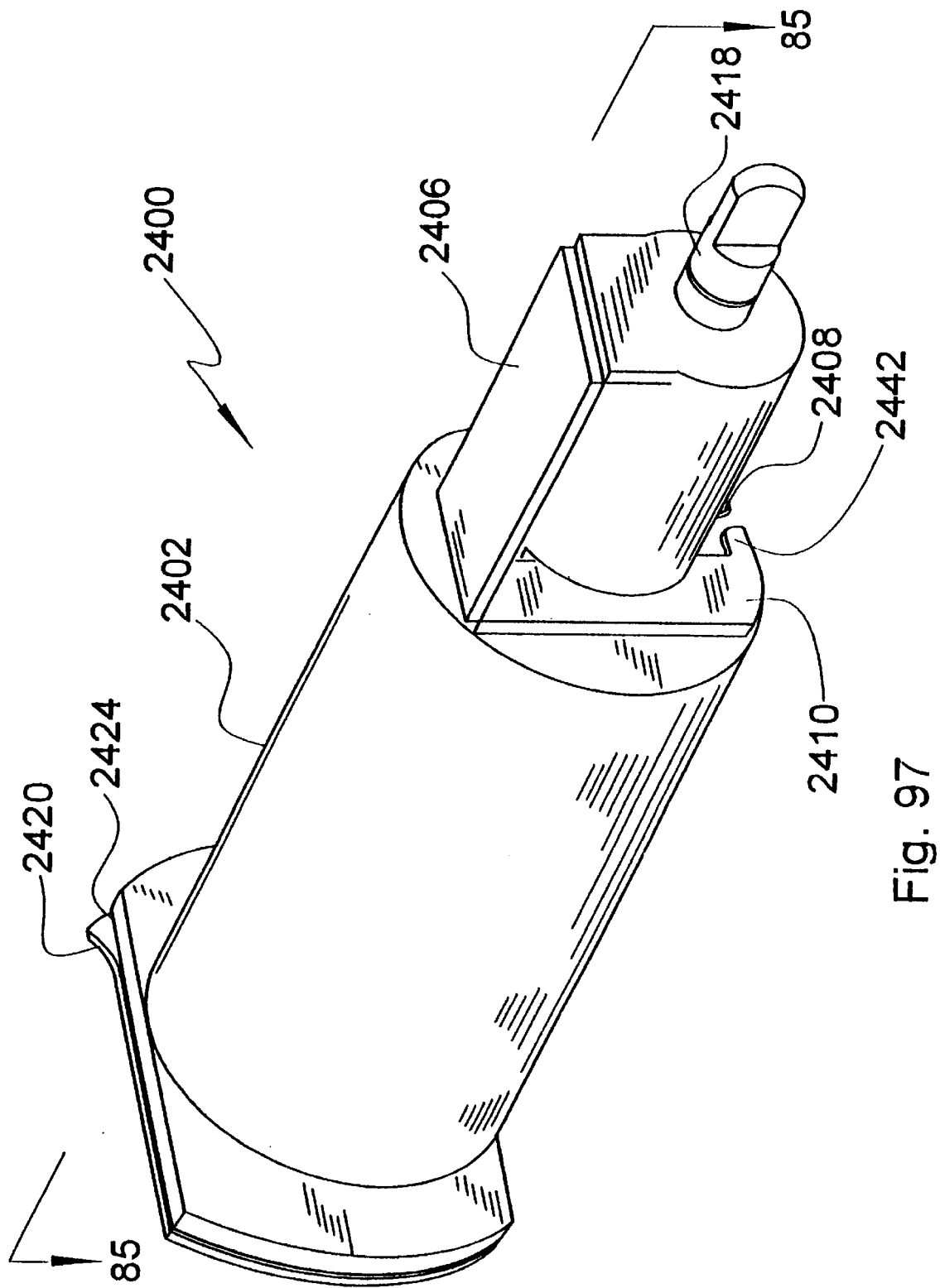
FIG. 97 is a perspective of a self contained medical phlebotomy needle device comprising a barrel and safety medical needle apparatus as an integral unit.
Figure 98:
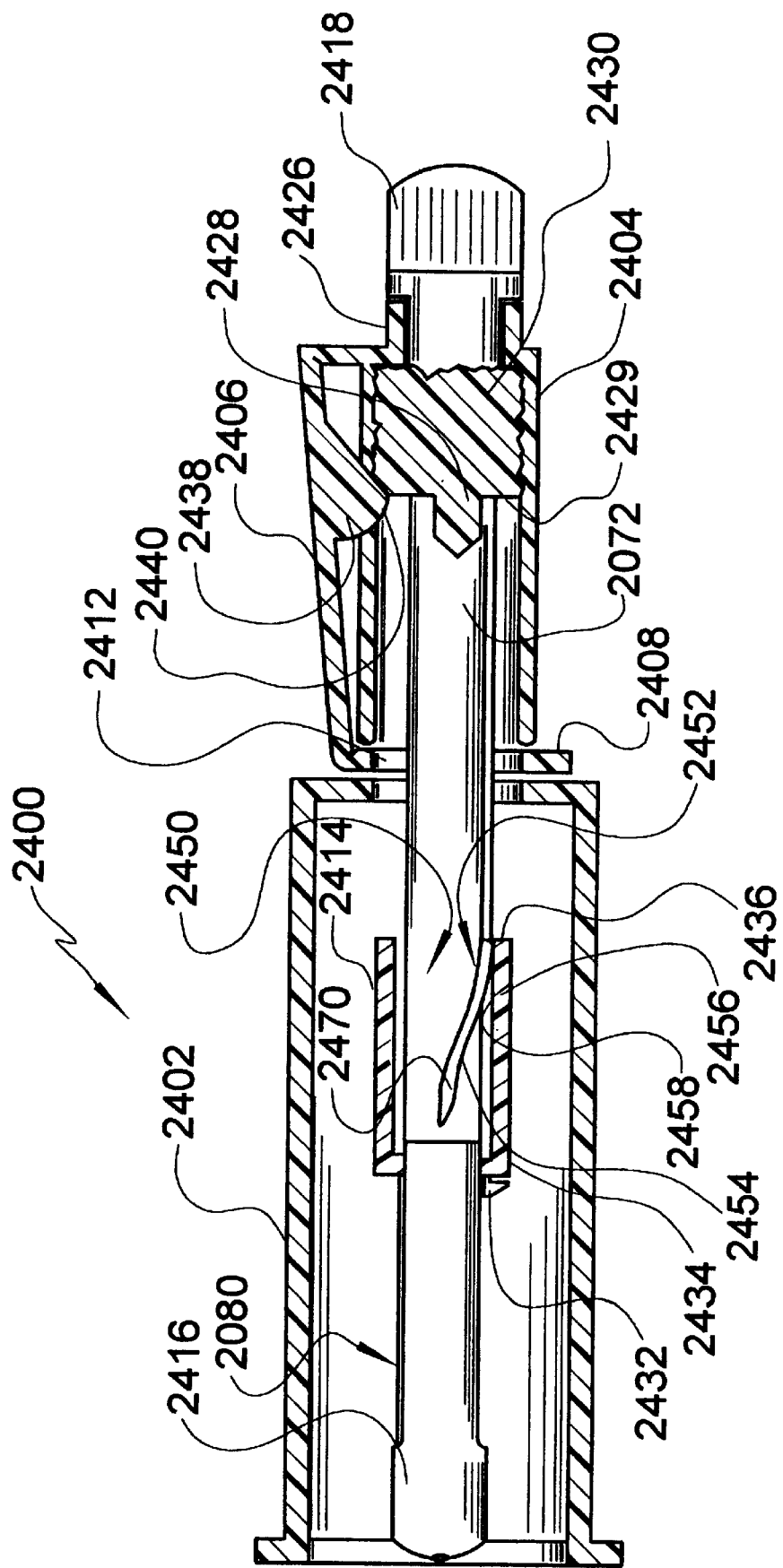
FIG. 98 is a cross section of the device of FIG. 97.

Another embodiment of a needle extension and retraction device 2400 is illustrated in FIGS. 97 and 98. Device 2400 comprises a barrel part 2402, which is similar to barrel 2202 (but does not contain optional slot 2210), and a segment 2404 which is similar to segment 2204. Segment 2402 also comprises a trigger strip 2406, which is similar in function to strip 2206, having a pair of legs 2408 and 2410 which are comparable to legs 2226 and 2228. Strip 2206 also comprises a circular opening 2412, similar to circular portion 2224, which permits passage of a rear hub 2414, in a manner in which rear hub 2060 is permitted to pass through portion 2224. However, in operation rear hub 2414 traverses through opening 2412 as a needle 2070 is extended for use and then once more as needle 2070 is retracted to safe containment. In FIGS. 97 and 98 device 2400 is in a pre-use state. In FIG. 98, device 2400 is shown to further comprise a sheath 2416 (which is similar in form and function to sheath 2090), a snubber 2080, a tube 2072, and a front cover 2418 (which is similar in form and function to 2050). When design considerations for combined barrel 2200 and assembly 2010 and device 2400 are appropriately met, three injection molded parts comprising the sheaths, the rear hubs, and the covers of combined barrel 2200 and assembly 2010 and device 2400 may be the same parts. The only other injection molded part of device 2400 is barrel 2402. A spring may be used in either assembly 2010 or device 2400 as the energy storing element. However, a spring is better used in device 2400 because a retracted needle is fully covered by barrel parts 2402 and 2404.

The major differences between parts of assembly 2010 and device 2400 are found in the barrel design. Barrel part 2402 is designed to be an integral part and a part which is deposed with other parts of device 2400. For that reason, it is desirable to add a removable label, such as label 2420 seen in FIG. 97, to cover and protect distal opening 2424 of barrel part 2402 prior to use. Device 2400 does not comprise a front hub. In place of the front hub is an integrally molded front or proximal part 2426. Integrally molded hub 2426 comprises an orifice for passage of needle 2070, an insertion tab 2428, seen as an internal section 2430 of a segment 2404, seen in FIGS. 98 and 99, because an outer portion of segment 2404 is removed for clarity of presentation and an annular stop 2429.

To prepare device 2400 for use in a medical procedure, cover 2418 is pulled proximally. As seen in FIG. 98, cover 2418 comprises a distally disposed release tab 2432 which is inserted through a slot (not shown) in rear hub 2414 and caught upon a distal face 2434 of hub 2414. Release tab 2432 is designed to be released by upward movement relative to hub 2414. Thus, when cover 2418 is pulled proximally, tube 2072 is compressed, hub 2414 is pulled by tab 2432 and sheath 2416, and snubber 2080 are likewise brought forward within barrel part 2402 and segment 2404.

Three things occur as needle 2070 and hub 2414 are moved into position for use of device 2400. In sequence, the following events prepare device 2400 for use:

1. An annular, proximally facing surface 2436 of hub 2414 is drawn into contact with a tab 2438. Tab 2438 comprises a cam-shaped surface 2440 which, in combination with a proximally moving hub 2414, forces trigger strip 2406 upward as hub 2414 nears stop 2429.
2. Once hub 2414 has passed through opening 2412, a lower segment of strip 2406 comprising opening 2412 and leg 2410 is free to move upward. Leg 2410 comprises an inwardly extending foot 2442 (see FIG. 97) which is disposed to come into contact with tab 2432 when hub 2414 is disposed.
3. Continued upward movement of tab 2432 discharges tab 2432 from being latched upon surface 2434 and cover 2418 is thereby released to be withdrawn from device 2400 to bare needle 2070 for use.

Downward compression of strip 2406 again places opening 2412 in the pathway of hub 2414 and results in retraction of needle 2070 into safe containment. Needle tip 2140 should be retained in secure disposition proximal to a proximal face of molded hub 2426 before use.

A marked difference between rear hub 2414 of device 2400 and rear hub 2060 of assembly 2400 is a combination of a slot 2450 and a latch arm 2452, which are partially illustrated in FIGS. 98 and 99. Latch arm 2452 comprises an elongated arcuate extension 2454 hinged to a side member 2456 of hub 2414 by a living hinge 2458. Extension 2454 comprises an outer surface 2470 which has a contour essentially the same as the outer surface of the rest of hub 2414. As seen in FIG. 100, extension 2454 comprises an inferiorly disposed bump 2472. When extension 2454 and therefore bump 2472 are disposed medially as seen in FIG. 98, bump 2472 acts as a stop or catch which impedes proximal movement of sheath 2416 much as stop 2180 impedes sheath 2090. However, bump 2472 is removed by causing extension 2454 to swing laterally out of the way of sheath 2416 when tab 2428 is engaged with hub 2414 as needle 2070 is moved proximally by cover 2418. As seen in FIG. 99, engagement of tab 2428 with hub 2414 (and extension 2454) causes extension 2454 to swing laterally about hinge 2458. The lateral swing removes bump 2472 from the path of sheath 2416, permitting sheath 2416 to move freely until hub 2414 is disengaged from segment 2404. Disengagement of hub 2414 is actuated by depressing strip 2406 against segment 2404 which, in turn, moves opening 2412 into alignment with hub 2414 releasing energy stored in tub 2072 to force hub 2414 and associated parts distally toward and into barrel part 2402.

A concern which must be addressed in any embodiment is that of assurance of true capture of needle 2070 upon retraction. Examples of apparatus for impeding outward passage of needle tip 2140 have been disclosed previously. Another example, seen in FIG. 101, is a section of a central portion of a forward hub (designated 2500) showing an asymmetric tubing connection 2502 embodiment which retards a retracted needle 2070 from reentering a needle pathway orifice 2504 in forward hub 2500. In combination tube 2072 and tubing connection 2502 act to permit needle 2070 to be retracted through orifice 2504, but bias needle tip 2140 into contact with an internal face 2506 of hub 2500 after needle tip 2140 is fully retracted into hub 2500. This is accomplished by providing a discontinuity 2508 in the wall of tubing connection 2502. Discontinuity 2508 permits a section 2510 of tube 2072 to be distorted by needle 2070 until needle 2070 is retracted. However, after retraction, section 2510 of tube 2072 relaxes to a position indicated by dashed lines 2512 and partially closes the needle reentry orifice. In this manner, needle tip 2140 and needle 2070 are securely trapped inside front hub 2500. The front plate which comprises internal face 2506 must be puncture proof or at least puncture resistant to reasonable lateral forces placed upon needle 2070 in the direction of face 2506.

Figure 102:
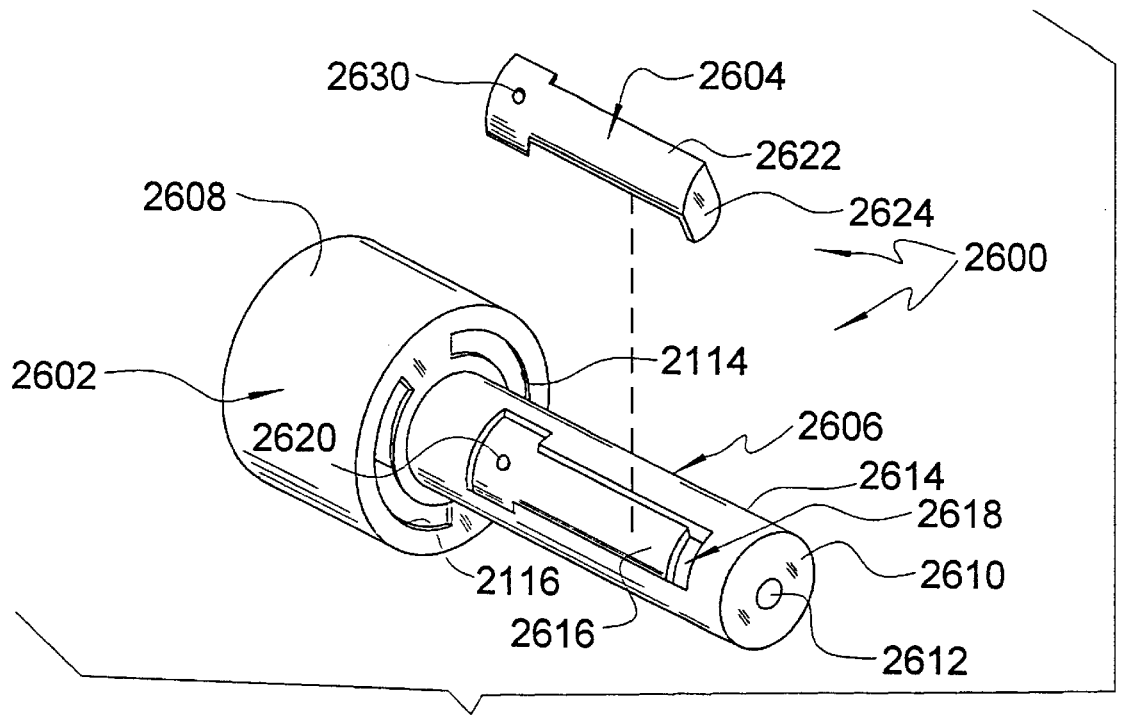
FIG. 102 is an exploded perspective of a forward needle hub assembly comprising a metal needle stop.
Figure 103:
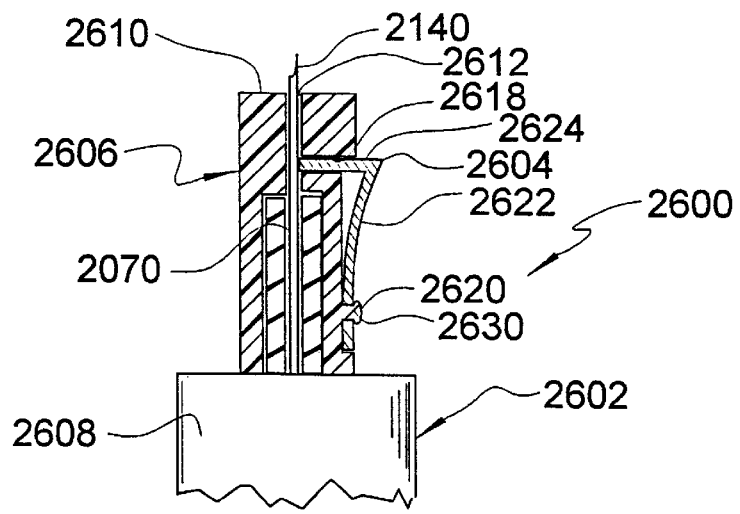
FIG. 103 is a side elevation of a portion of the forward needle hub assembly of FIG. 102 with an inserted needle, the stop assembled to the rest of the hub and proximal portions of the hub seen in cross section for better presentation of those parts of this forward needle hub compared to the hub seen in earlier figures.

In those cases where a front plate or other needle tip 2140 containing parts are made from material which is not puncture proof or even sufficiently puncture resistant, a needle impervious material should be used to effectively capture and hold needle tip 2140 from exiting a forward hub, thereby creating an unsafe condition. Reference is made to FIGS. 102 and 103 wherein a forward hub assembly 2600 is seen. Hub assembly 2600 comprises a moldable part 2602 (which may be made from a synthetic resinous material such as polypropylene) and a spring part 2604. Other than structural differences which permit assembling part 2604 to part 2602, Forward hub assembly 2600 is similar in form and function to forward hub 2040 and other similar hubs disclosed previously.

Moldable hub part 2602 comprises an elongated proximal cylindrical housing segment 2606 and a pair of slots 2114 and 2116, disposed in a cylindrical connector segment 2608. Segment 2606 comprises a forward blunt end 2610 and an internal cylindrical needle passage 2612. Inset within an external surface 2614 is a depression 2616. Depression 2616 comprises a form and shape which comfortably accepts insertion of spring part 2604. Disposed within depression 2616 is a locking slot 2618 and a raised mounting tab 2620.

Spring part 2604 is preferably made from spring steel, although any material, which provides a safe barrier that prevents escape of needle tip 2142 after needle 2070 is retracted, may be used. Spring part 2604 comprises an elongated strip 2622 and a stopping segment 2624, which is essentially at a right angle to strip 2622 to permit insertion of segment 2624 through slot 2618 and further insertion of segment 2624 through slot 2618 into a needle tip 2140 obstructing position after needle 2070 is retracted. In addition, an attachable support mount should be used to provide a secure attachment of spring part 2604 to segment 2606. As seen in FIGS. 102 and 103, spring part 2604 comprises a mounting hole 2630 which is securely affixed to tab 2620, preferably by a press fit Such connections are common in the assembly of plastic parts to other parts such as parts made from metal. Once spring part 2604 is affixed to hub part 2602, a combination of locking attachment of tab 2620 about hole 2630 and geometry of inset 2616 relative to spring part 2604 maintains structural integrity of assembly 2600.

As seen in FIG. 103, when needle 2170 is in a pre-use state with needle tip 2140 disposed proximal to end 2610, segment 2624 rests upon needle 2170 through slot 2618. When needle tip 2140 is retracted past slot 2618 and segment 2624 (not shown), the spring tension retained in strip 2622 discharges segment 2624 fuirther into needle passage 2612 to from an effective and safe stop.

In summary, the apparatus and method disclosed herein is a significant improvement from the present state of the art of self-retracting medical needle devices.

The inventions disclosed herein may be embodied in other specific forms without departing from its spirit or essential characteristics. The described embodiments are to be considered in all respects only as illustrative and not restrictive. The scope of the invention is, therefore, indicated by the appended rather than by the foregoing description. All S changes which come within the meaning and range of equivalency of the claims are to be embraced within their scope.

What is claimed and desired to be secured by united states letters patent is:

1. A medical needle extending and retracting blood sampling device by which a double ended medical needle is transported within a protective housing, extended to a stable position for use in a medical procedure and fully, automatically retracted into safe containment after use such that both ends of the needle are protected before and after use, said device comprising:

the medical needle comprising an elongated cannula having a first sharpened needle point disposed upon a proximal end of the needle and a second sharpened needle point disposed upon a distal end of the needle;

a removable cover which is disposed about and protects the first sharpened end prior to use;

a sheath which is disposed to protectively cover the second needle point prior to initiation and after completion of a medical procedure, but which is disposed to be freely moved to permit access by a blood sampling tube to the second needle point during the medical procedure;

a housing in which at least the first sharpened needle point is safely disposed at the end of the medical procedure;

an energy storing member which stores energy as the needle is extended proximally relative to a portion of the housing to prepare the device for use in the medical procedure; and a needle retraction apparatus which is cocked when the needle is extended and which is manually actuated to cause the energy storing member to retract the needle into safe containment thereby providing safe protection for the first and second needle points.

2. A medical needle extending and retracting blood sampling device according to claim 1, wherein said housing comprises a barrel used with blood sampling tubes.

3. A medical needle extending and retracting blood sampling device according to claim 1, wherein said energy storing member is an elastic tube.

4. A medical needle extending and retracting blood sampling device according to claim 3, wherein said elastic tube comprises material having a durometer in the range of thirty-five to fifty.

5. A medical needle extending and retraction blood sampling device according to claim 1, wherein said elastic tube comprises a restraint which strictly restrains said tube from stretching.

6. A safety phlebotomy needle extending and powered retraction device comprising:

an elongated cylindrical tubing module comprising a fore part and a rear part, said rear part comprising a barrel which receives a blood sampling vacuum tube;

a needle containment housing which is disposed and releasibly, but securely affixed into the fore part as a separable component of said device, said housing comprising:

a medical needle having a first sharpened tip on a forwardly disposed end and a second sharpened tip on a rearwardly disposed end of an elongated cannula;

a hub disposed about and securely affixed to the medical needle;

a front cap comprising an orifice through which, during a medical procedure, said first tip travels only upon rearward retraction of said needle and a protective shield for a retracted needle;

an energy storing member which stores energy as the medical needle is extended for use;

a sheath which protects the rearwardly disposed end and second sharpened tip at least when the needle containment housing is removed from the fore part of the module; and said tubing module further comprising an actuator for releasing the medical needle hub thereby activating the energy storing member to effectively retract the medical needle into safe containment within said housing.

7. A medical phlebotomy needle extending and powered retraction device according to claim 6, wherein the housing further comprises a snubber which covers the rearwardly disposed end and second sharpened end and thereby restricts blood flow whenever a blood sampling tube is removed from the barrel.

8. A medical phlebotomy needle extending and powered retraction device according to claim 7, wherein said snubber comprises an elongated elastic cap.

9. A medical phlebotomy needle extending and powered retraction device according to claim 8, wherein, in combination, said snubber and said sheath in combination comprise means for extending said sheath rearwardly to cover said second tip whenever a vacuum tube is removed from attachment to the phlebotomy needle.

10. A medical phlebotomy needle extending and powered retraction device according to claim 6, wherein said sheath comprises a latch which securely affixes the sheath relative to the second sharpened tip to provide protection from inadvertent sticks thereby.

11. A medical needle subsystem used in a medical needle extending and powered needle retraction device, said subsystem being a disposable part and comprising:

a medical needle comprising at least one sharpened point;

a needle containment housing and covering apparatus comprising:

before extending said needle and using said device, at least one cover which is disposed to cover a portion of said needle during transport, storage and during extension of said needle, but which is removed prior to use of the needle;

a cap disposed to releasibly affix the cover to the rest of said housing, said cap comprising an orifice through which the needle is disposed during transport, storage and use and through which the needle is totally retracted for safe containment within said containment housing;

a catch securely affixed to said housing apparatus to which a latch is releasibly affixed when the needle is extended for use; and a compressible energy storing member which is compressed during needle extension to accrue energy for needle retraction, said energy storing member providing a needle covering portion of said housing and powered retraction of said medical needle into the needle containment housing when the releasable latch is disengaged from said catch.

12. A method for transporting, preparing and safely retracting, at the end of a medical procedure, a retractable medical phlebotomy needle comprising the steps of:

provixing an extendable and retractable medical phlebotomy needle assembly comprising a medical phlebotomy needle having a first sharpened point on a patient related end of the needle and a second sharpened point on the other end of the needle, a needle hub which is securely affixed to the needle, a snubber which provides a displaceable, pierceable cover for the second sharpened point, a sheath which, when the assembly is prepared for use, is displaced by a blood sampling tube but at other times is securely affixed to the needle hub to provide a protective cover about the second point, a connector part by which the assembly is affixed to a barrel component for use and an energy storage member disposed to be compressed and thereby store energy as the hub and connector part are moved one toward the other to effectively extend the needle for use, the connector part comprising an orifice through which the needle is displaced during transport and through which the first needle point is retracted into safe containment within the assembly upon needle retraction;

providing a front cap for covering a portion of the medical needle assembly associated with the first sharpened point and a back cap associated with another portion of the medical needle assembly associated with the second sharpened end;

providing the barrel component for blood sampling and acquisition, said barrel component comprising an elongated barrel portion for receiving vacuum actuated blood sampling tubes, an elongated cylindrical housing integral with said barrel portion and a releasible catch;

removing the back cap;

inserting the assembly, beginning with the end of the assembly associated with the second sharpened point, into the cylindrical housing;

displacing the assembly into the cylindrical housing until contact is made with the releasible catch;

continuing to displace the assembly into the cylindrical housing thereby compressing the storage member to store energy therein and extending the medical needle outward through the orifice;

securely but releasibly affixing the front cap to the cylindrical housing; and removing the front cap, exposing the medical needle for use;

performing a medical procedure; and retracting said medical needle into said assembly with accompanying results of safely enclosing each sharpened point.

13. An extendable and retractable phlebotomy needle apparatus comprising:

a phlebotomy needle comprising two sharpened ends;

needle extender apparatus for extending one sharpened end of said needle outward from the apparatus for use;

an energy storing part which stores needle retracting energy as the needle is extended;

a releasible latch which securely, but releasibly affixes said needle in place while a medical procedure is performed;

a release by which said latch is disengaged which resultingly enables said energy storage means to power retraction of said needle into safe containment within the apparatus; and at least one shield to protectively cover each sharpened end of said needle when retracted.

14. An extendable and retractable phlebotomy needle apparatus comprising:

a housing comprising an orifice through which a phlebotomy needle is retracted into safe containment;

a phlebotomy needle comprising a sharpened transcutaneous end and a blood sampling tube piercing end, said transcutaneous end being disposed through the orifice from a point of manufacture until and while the needle is extended for use;

a needle advance mechanism by which the needle is outwardly extended through the orifice of the housing in preparation for use;

an energy storing part for accruing needle retracting energy as the needle is outwardly extended;

a releasible latch for securing the needle, when extended, in place while a medical procedure is performed;

a release mechanism whereby the latch is released thereby permitting the energy storing part to power retraction of said needle into safe containment within the apparatus; and at least one shield which provides a protective guard for each needle end to assure against inadvertent contact with a sharp end after the needle is retracted.

15. An extendable and retractable phlebotomy needle apparatus comprising:

a housing;

a phlebotomy needle assembly disposed within said housing, said assembly comprising:

a phlebotomy needle at least partially disposed within said assembly;

a needle extender by which said needle is moved to be outwardly disposed from said housing without degrading medical efficacy of said needle; and a compressively storing energy part which stores energy as the needle is outwardly extended for use in a medical procedure, said energy storing part being available for use to power needle retraction into the housing.

16. A phlebotomy needle apparatus according to claim 15 further comprising a barrel component which provides an interface between a blood sampling vacuum tube and the phlebotomy needle.

17. A phlebotomy needle apparatus according to claim 16, wherein said barrel component comprises a trigger device which permits a user to selectively actuate the energy storing part to retract the needle into the housing.

18. A phlebotomy needle apparatus according to claim 15, wherein said energy storing part comprises an elastic tube.

19. A phlebotomy needle apparatus according to claim 15, wherein said needle comprises a sharpened tip for accessing a blood vessel.

20. A phlebotomy needle apparatus according to claim 19, wherein said extender comprises a cap having an orifice through which said sharpened tip travels only when said needle is retracted.

21. A phlebotomy needle apparatus according to claim 20, wherein said cap comprises a section disposed about said orifice which is flexible permitting said orifice to be moved relative to said needle tip to assure the needle tip retracts but once through said orifice.

22. A phlebotomy needle apparatus according to claim 21, wherein said section comprises a portion which "oil cans."

23. A phlebotomy needle apparatus according to claim 21, wherein said assembly comprises a hub disposed about said needle.

24. A phlebotomy needle apparatus according to claim 21, wherein said extender comprises means for transferring said hub from a first position where the hub is disposed for travel and the associated medical needle is disposed through said orifice for safe transport to a second position where hub is securely affixed for the medical procedure and the medical needle tip does not pass through the orifice.

25. A phlebotomy needle apparatus according to claim 21 further comprising a release which actuates the compressively storing energy part to retract the medical and needle tip through the orifice into safe containment within said housing.

* * * * *